(12) United States Patent
Blecka et al.

(10) Patent No.: US 8,992,833 B2
(45) Date of Patent: Mar. 31, 2015

(54) SYSTEM AND METHOD FOR MULTI-ANALYTE DETECTION

(71) Applicant: Bio-Rad Laboratories, Inc., Hercules, CA (US)

(72) Inventors: Lawrence Blecka, Walnut Creek, CA (US); Larry Seamer, Vallejo, CA (US); Sachi Rastogi, Pleasant Hill, CA (US); Chris Tsai, San Ramon, CA (US); Nasser Jafari, American Canyon, CA (US); Ken J. Lafredo, Walnut Creek, CA (US)

(73) Assignee: Bio Rad-Laboratories, Inc., Hercules, CA (US)

( * ) Notice: Subject to any disclaimer, the term of this patent is extended or adjusted under 35 U.S.C. 154(b) by 0 days.

(21) Appl. No.: 13/717,425

(22) Filed: Dec. 17, 2012

(65) Prior Publication Data

US 2013/0216454 A1     Aug. 22, 2013

Related U.S. Application Data

(60) Division of application No. 13/094,743, filed on Apr. 26, 2011, now Pat. No. 8,357,537, which is a division of application No. 11/784,596, filed on Apr. 6, 2007, now Pat. No. 7,955,555, which is a continuation of (Continued)

(51) Int. Cl.
*G01N 33/48* (2006.01)
*B01L 9/00* (2006.01)
(Continued)

(52) U.S. Cl.
CPC .......... *B01L 9/00* (2013.01); *Y10T 436/143333* (2013.01); *Y10T 436/2575* (2013.01);
(Continued)

(58) Field of Classification Search
CPC .......................... G01N 35/025; G01N 35/026
USPC .............. 422/64, 63, 67, 68.1, 512, 531–532
See application file for complete search history.

(56) References Cited

U.S. PATENT DOCUMENTS 4,284,412 A    8/1981   Hansen et al.
4,345,843 A    8/1982   Berglund et al.
(Continued)

FOREIGN PATENT DOCUMENTS

WO      93/20440       10/1993
WO      03/012454 A1   2/2003

OTHER PUBLICATIONS

EPO, Communication—extended European search report dated Jan. 4, 2012 for application No. EP 11179195.0.

(Continued)

*Primary Examiner* — Brian R Gordon
(74) *Attorney, Agent, or Firm* — Jones Day

(57) ABSTRACT

The present invention provides a system and method for the simultaneous detection of multiple analytes in a sample. The detection system includes a housing that holds a reagent carousel rotatably coupled thereto. Further included in the housing is an incubator carousel rotatably coupled thereto. The housing also includes magnetic material that is associated with the incubation carousel for assisting in separation beads from reagent and wash solution. A robot, associated with the housing is configured to manipulate at least either the reagent carousel or the incubator carousel and transfer materials therebetween. Reaction vessels hold samples and reaction vessels handlers move the reaction vessels. Sample analysis is determined by at least one laser based detector.

4 Claims, 45 Drawing Sheets

Related U.S. Application Data application No. 10/894,824, filed on Jul. 19, 2004, now Pat. No. 7,220,385.

(60) Provisional application No. 60/489,001, filed on Jul. 21, 2003, provisional application No. 60/488,572, filed on Jul. 18, 2003.

(51) Int. Cl.
*G01N 35/00* (2006.01)
*G01N 35/02* (2006.01)
*G01N 15/14* (2006.01)

(52) U.S. Cl.
CPC ...... *Y10T436/11* (2013.01); *Y10T 436/113332* (2013.01); *Y10T 436/25* (2013.01); *G01N 35/0099* (2013.01); *G01N 35/025* (2013.01); *G01N 2035/00356* (2013.01); *G01N 15/14* (2013.01); *G01N 35/0098* (2013.01)
USPC ............... 422/64; 422/63; 422/67; 422/68.1; 422/512

(56) References Cited

U.S. PATENT DOCUMENTS

| | | | |
|---|---|---|---|
| 5,133,373 | A | 7/1992 | Hoffman et al. |
| 5,186,194 | A | 2/1993 | Kitajima |
| 5,541,064 | A | 7/1996 | Bacus et al. |
| 5,580,524 | A | 12/1996 | Forrest et al. |
| 5,610,069 | A * | 3/1997 | Clark et al. .................... 436/49 |
| 5,620,898 | A | 4/1997 | Yaremko et al. |
| 5,736,330 | A | 4/1998 | Fulton |
| 5,772,693 | A | 6/1998 | Brownlee |
| 5,802,327 | A | 9/1998 | Hawley et al. |
| 5,827,660 | A | 10/1998 | Singer et al. |
| 5,827,744 | A | 10/1998 | Fose et al. |
| 5,846,491 | A | 12/1998 | Choperena et al. |
| 5,882,594 | A | 3/1999 | Kawaguchi et al. |
| 5,908,599 | A | 6/1999 | Behringer et al. |
| 5,981,180 | A | 11/1999 | Chandler et al. |
| 5,985,672 | A | 11/1999 | Kegelman et al. |
| 6,015,532 | A | 1/2000 | Clements et al. |
| 6,046,807 | A | 4/2000 | Chandler |
| 6,057,107 | A | 5/2000 | Fulton |
| 6,066,298 | A | 5/2000 | Fukunaga |
| 6,096,561 | A | 8/2000 | Tayi |
| 6,139,800 | A | 10/2000 | Chandler |
| 6,190,617 | B1 | 2/2001 | Clark et al. |
| 6,268,222 | B1 | 7/2001 | Chandler et al. |
| 6,366,354 | B1 | 4/2002 | Chandler |
| 6,411,904 | B1 | 6/2002 | Chandler |
| 6,449,562 | B1 | 9/2002 | Chandler |
| 6,514,295 | B1 | 2/2003 | Chandler et al. |
| 6,524,793 | B1 | 2/2003 | Chandler et al. |
| 6,528,165 | B2 | 3/2003 | Chandler |
| 6,592,822 | B1 | 7/2003 | Chandler |
| 6,827,904 | B2 * | 12/2004 | Kitagawa ...................... 422/509 |
| 7,141,416 | B2 | 11/2006 | Krutzik |
| 7,220,385 | B2 | 5/2007 | Blecka et al. |
| 7,731,899 | B2 | 6/2010 | Talmer et al. |
| 8,318,500 | B2 * | 11/2012 | Ammann et al. ............... 436/54 |
| 2001/0046452 | A1 | 11/2001 | Roback et al. |
| 2002/0064884 | A1 | 5/2002 | Devlin et al. |
| 2002/0182609 | A1 | 12/2002 | Arcot |
| 2003/0087443 | A1 | 5/2003 | Pressman et al. |
| 2003/0132538 | A1 | 7/2003 | Chandler |
| 2005/0123445 | A1 | 6/2005 | Blecka et al. |
| 2005/0279387 | A1 | 12/2005 | Blackwell et al. |

OTHER PUBLICATIONS

EPO, Supplementary European Search Report dated Nov. 20, 2009 for application No. 04786083.8.
USPTO, Final Office Action dated Oct. 26, 2006 in U.S. Appl. No. 10/894,824, now patent No. 7,220,385.

\* cited by examiner

SYSTEM AND METHOD FOR MULTI-ANALYTE DETECTION

1. RELATED APPLICATIONS

This application is a divisional of application Ser. No. 13/094,743, filed Apr. 26, 2011, now U.S. Pat. No. 8,357,537, which is a divisional of application Ser. No. 11/784,596, filed Apr. 6, 2007, now U.S. Pat. No. 7,955,555, which is a continuation of application Ser. No. 10/894,824, filed Jul. 19, 2004, now U.S. Pat. No. 7,220,385, which claims the benefit of U.S. provisional patent application No. 60/489,001, filed Jul. 21, 2003, and 60/488,572, filed Jul. 18, 2003, all of which are incorporated herein by reference in their entireties.

2. BACKGROUND OF THE INVENTION

2.1 Field of the Invention

Generally, the present invention relates to a system and method for multiple analyte detection. More particularly, multiple analytes are contained within a single sample and analyzed simultaneously using high-speed digital signal processing.

2.2 Description of Related Art

Disease analysis, research, and drug development depend heavily on laboratory assay analysis. An example of an assay that has become commonplace in today's laboratory is the immunoassay. Many other types of laboratory analyses are also conducted in today's laboratories, such as analysis on blood, urine, serum, blood plasma, and other body fluids for proteins, viruses, bacteria, and other conditions.

Traditionally, laboratory assay analyses were very time consuming processes, requiring lab personnel to perform precise measurements of reagents and samples, mixtures, centrifuging, etc. Each step of these analyses typically needs to be repeated multiple times to acquire statistically significant data. Furthermore, the processes are often wasteful of costly solvents, solutions, reagents, require numerous man-hours, and are generally slow.

Accordingly, automated devices were envisioned and developed to quicken the process, generate more accurate results and make the process more economical and efficient. However, a drawback of these devices is that a limited number of analyses can be run on any given sample at any time. Therefore, much time is still required to analyze a sample for multiple analytes.

Accordingly, a system and method for testing multiple analytes, with little or no human intervention, from a single test sample would be highly desirable.

3. BRIEF SUMMARY OF THE INVENTION

According to one embodiment, a system and method is provided for the simultaneous detection of multiple analytes. The system comprises a housing and a reagent carousel rotatably coupled to the housing. Also rotatably coupled with the housing is an incubator carousel. Magnetic material is associated with the incubation carousel for assisting in washing samples held by the incubator carousel. Furthermore, at least one robot is coupled to the housing. The robot is configured to manipulate the reagent carousel and/or the incubator carousel. Reaction vessel handlers are responsible for moving reaction vessels between locations, such as a pre-testing location, testing location, and post-testing location. There is also at least one laser based detector for analyzing samples following mixing the sample with reagents.

In a preferred embodiment, there is a flow cytometer for conducting the analysis of the samples. It is also preferred that washers are included for washing the robots and robot probes.

According to another embodiment the incubator carousel further includes a plurality of rings. Each ring is rotatable with respect to the other rings such that high throughput is achieved from the system.

According to yet another embodiment, the reagent carousel is configured to contain reagent kits. The reagent kits are accessible by at least one robot. The kits and reagent carousel are designed to be utilized during use of the system and without interruption of overall system processes.

4. BRIEF DESCRIPTION OF THE DRAWINGS

For a better understanding of the nature and objects of the invention, reference should be made to the following detailed description, taken in conjunction with the accompanying drawings, in which.

Figure 12:
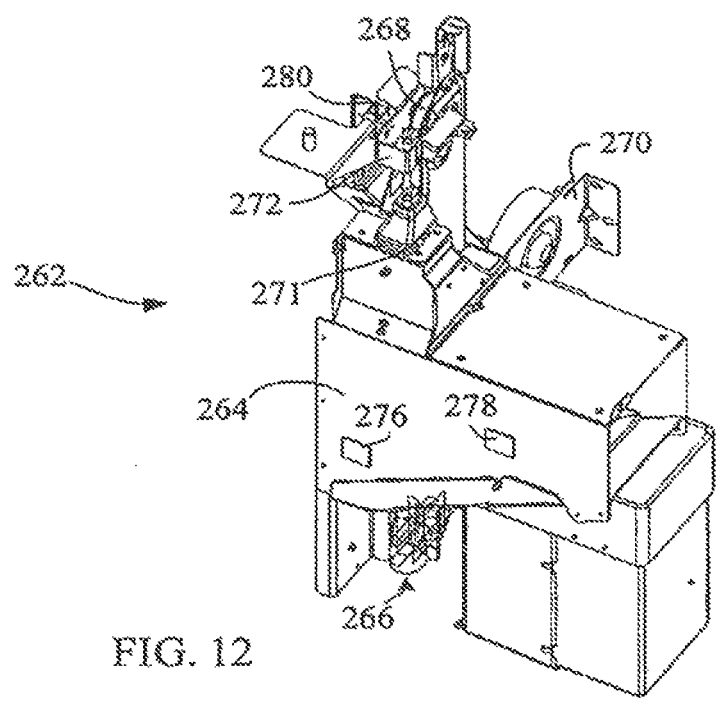
FIG. 12 is a perspective view of a reaction vessel supply sub-assembly of FIG. 11.
Figure 13A:
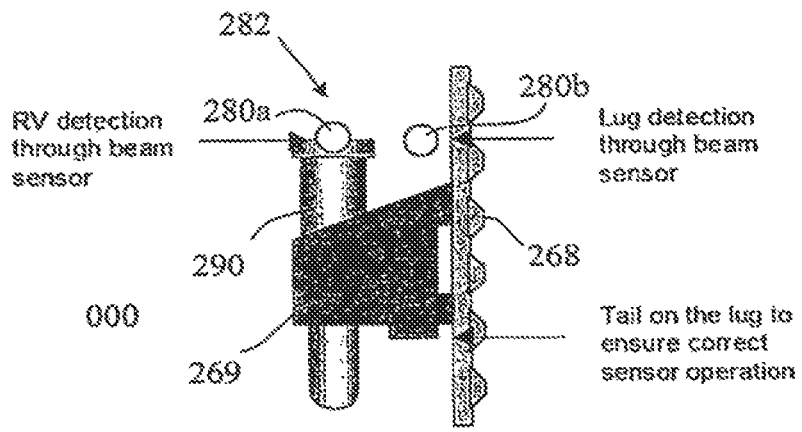
Figure 13B:
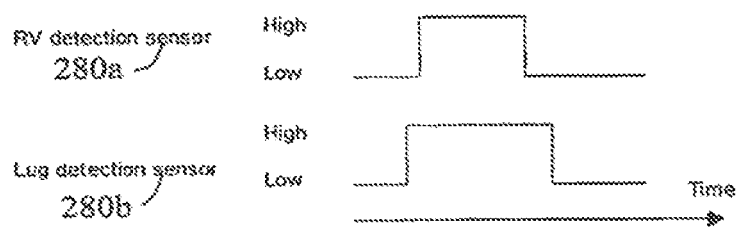
Figure 13C:
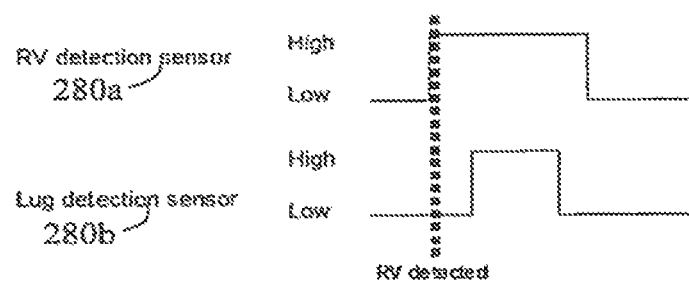
Figure 14:
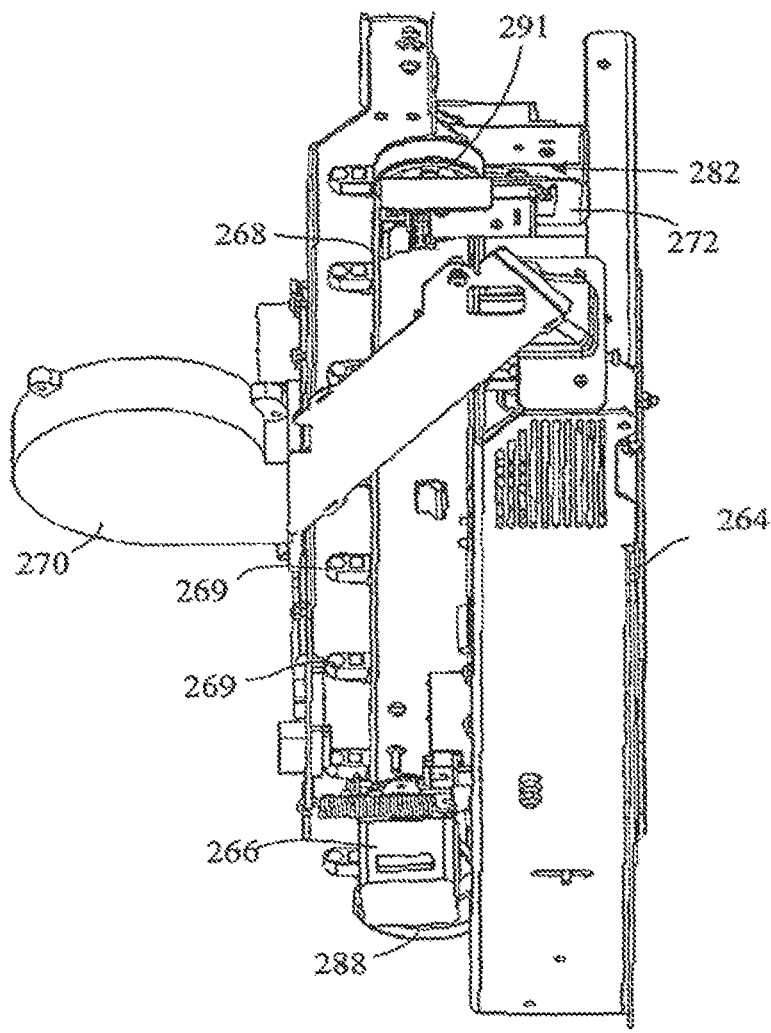
Figure 15:
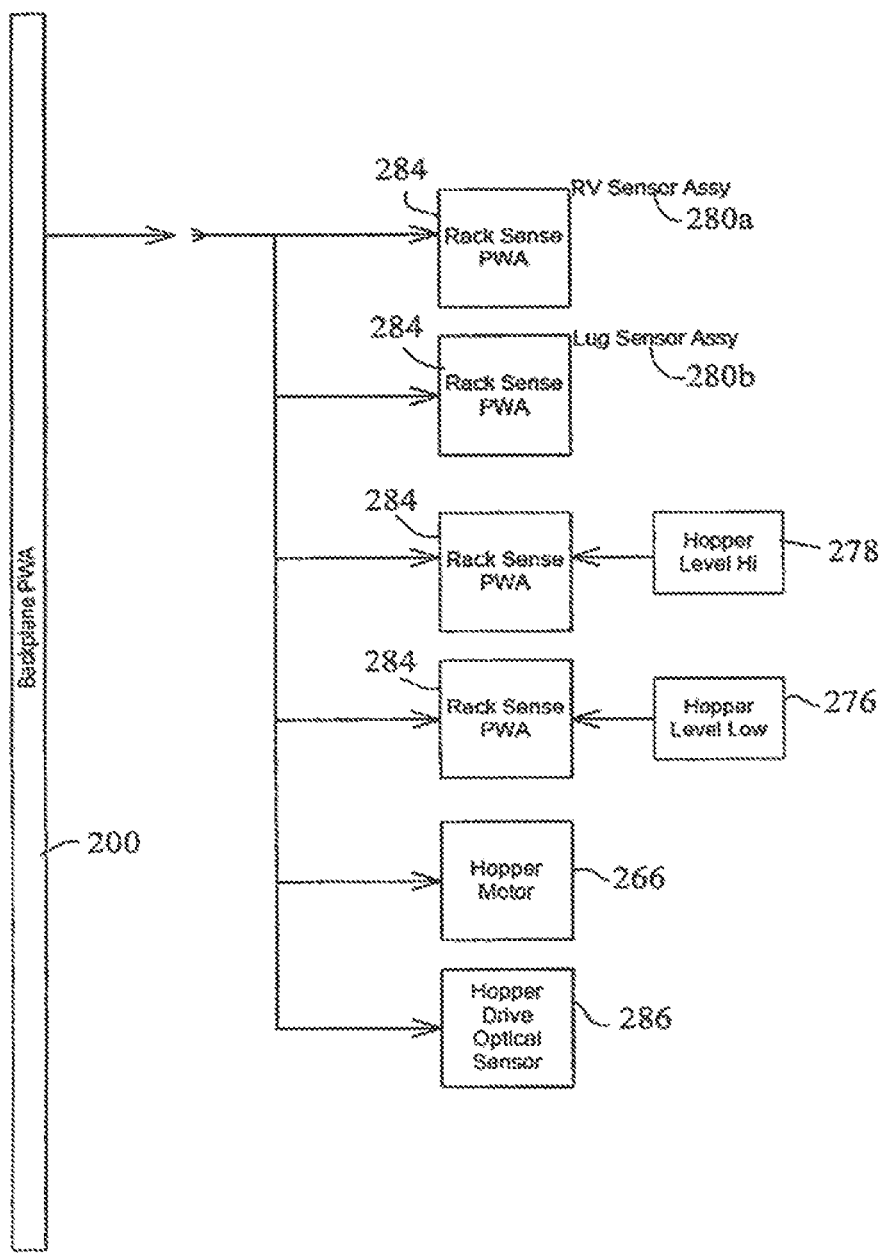
Figure 16:
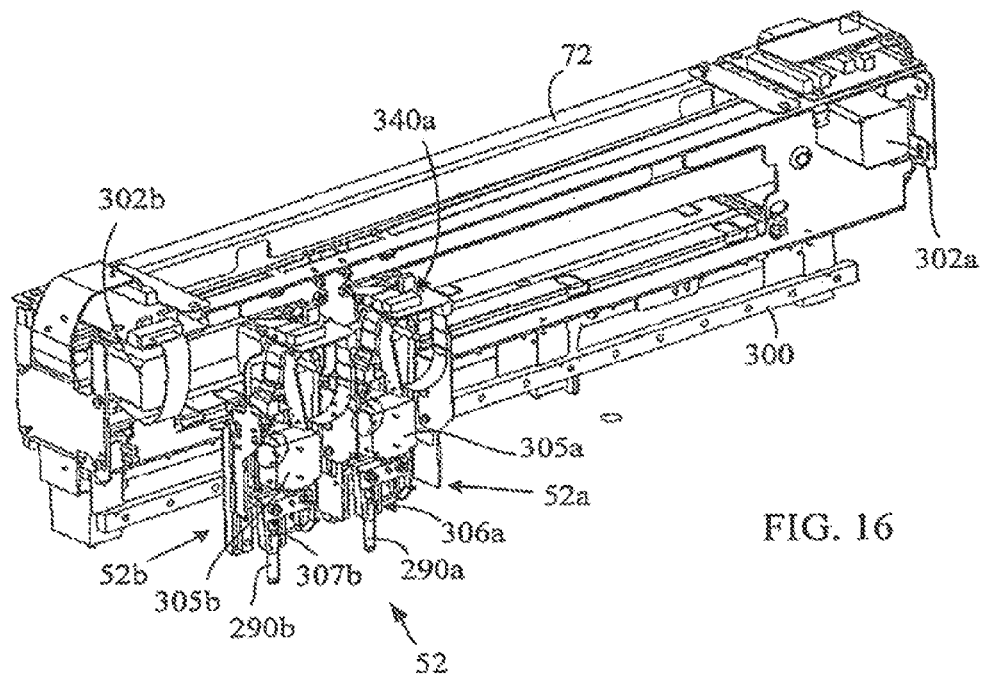
Figure 20:
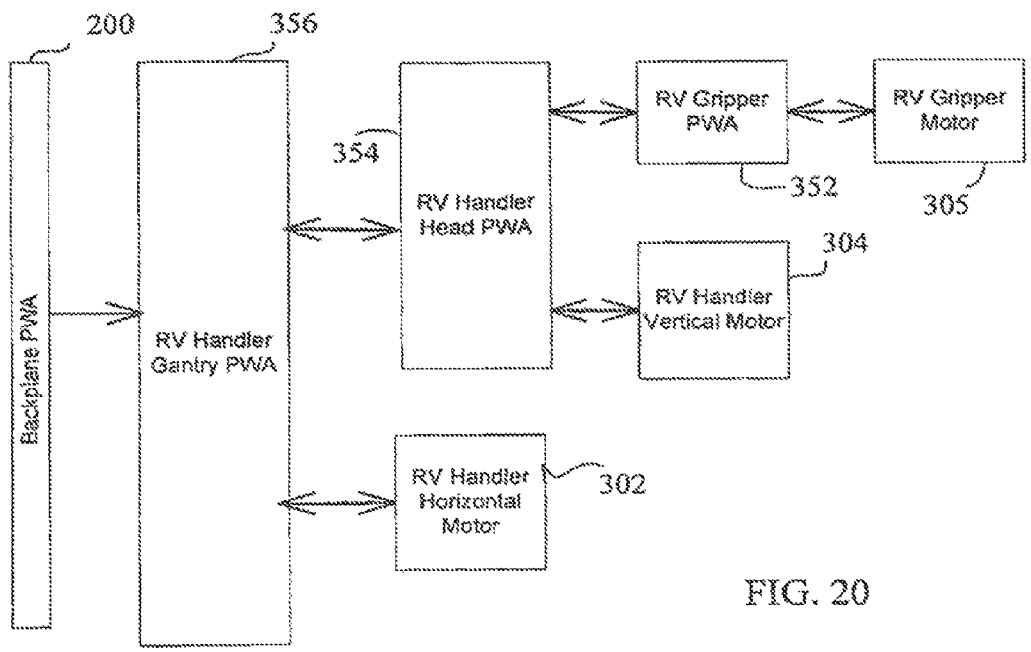
Figure 21:
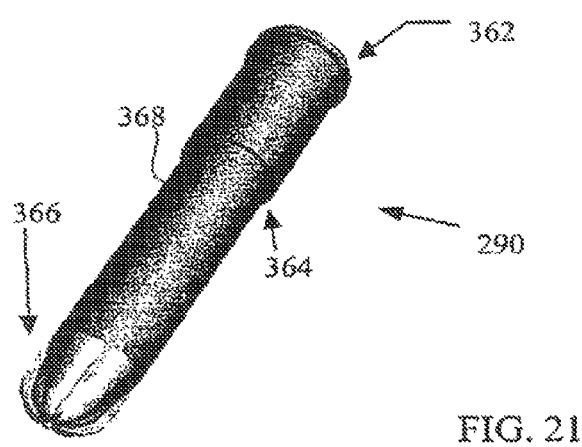
Figure 22:
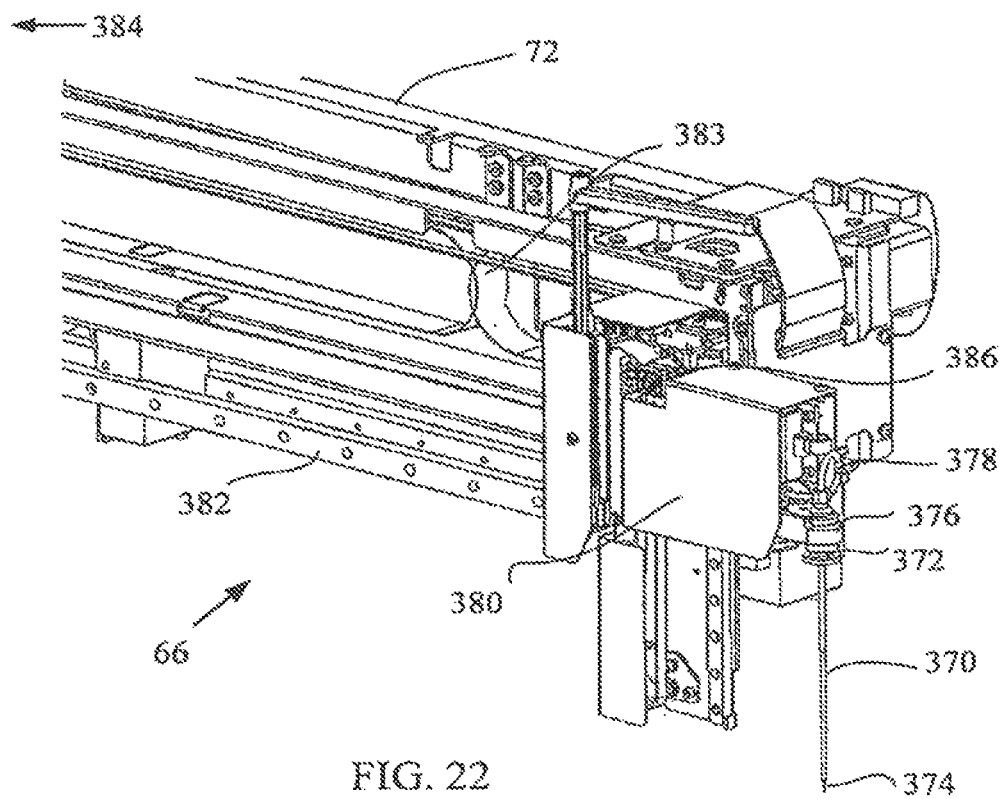
Figure 23:
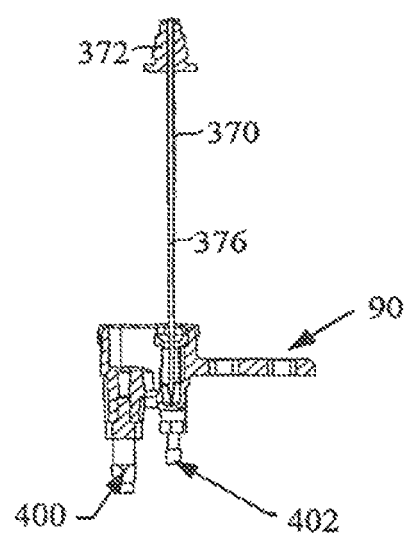
Figure 24:
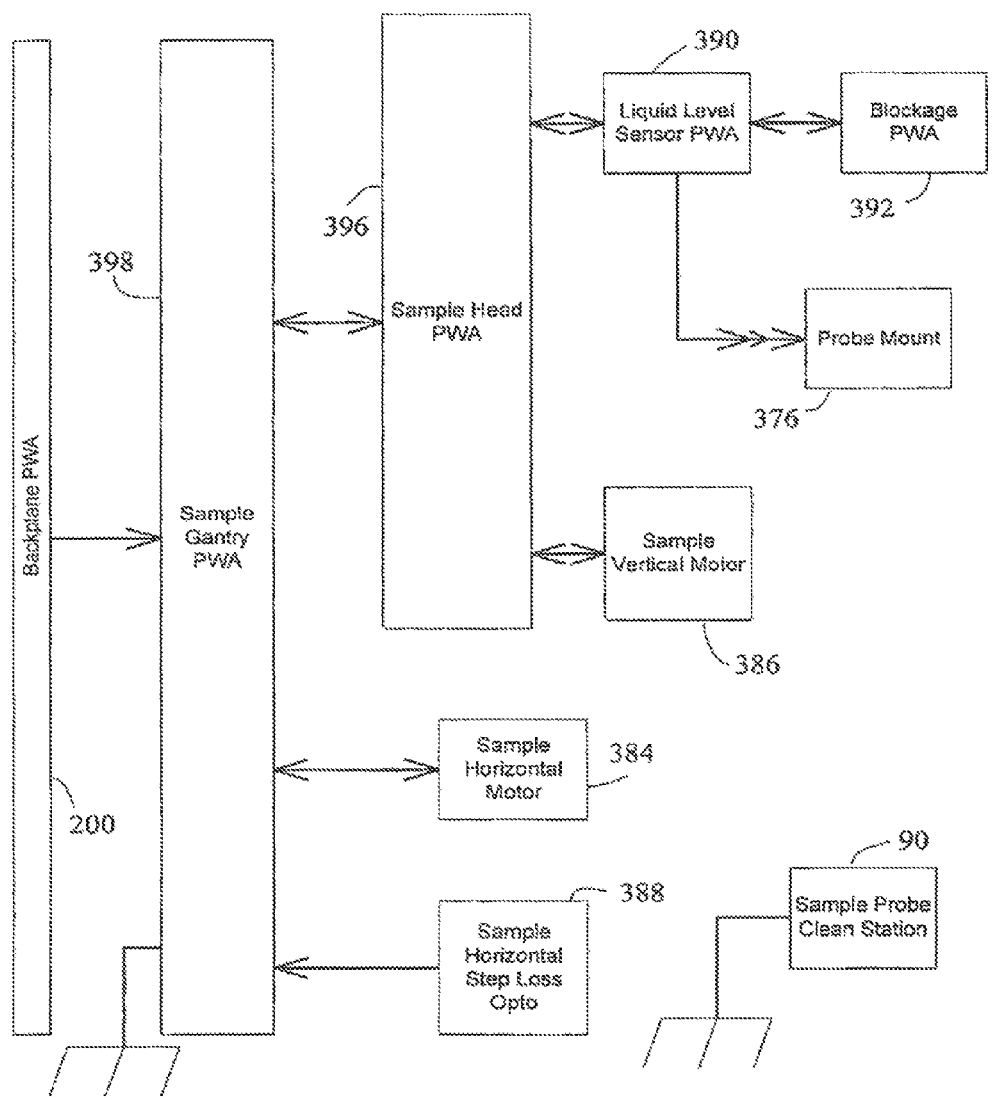
Figure 25:
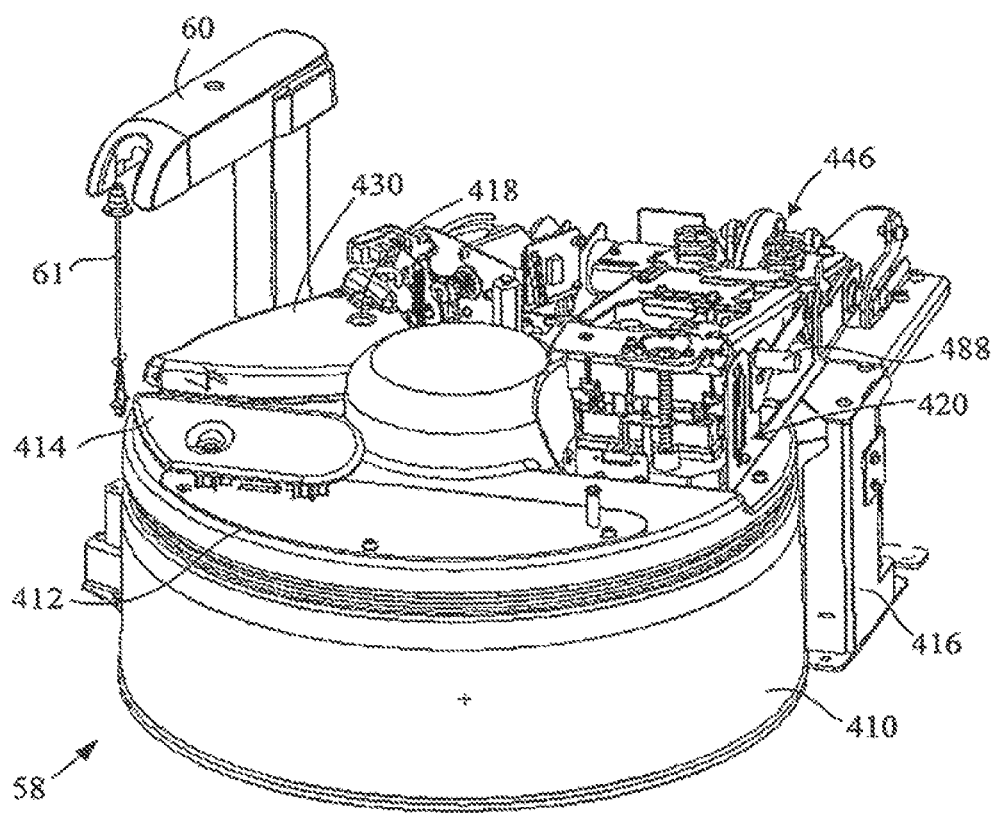
Figure 26:
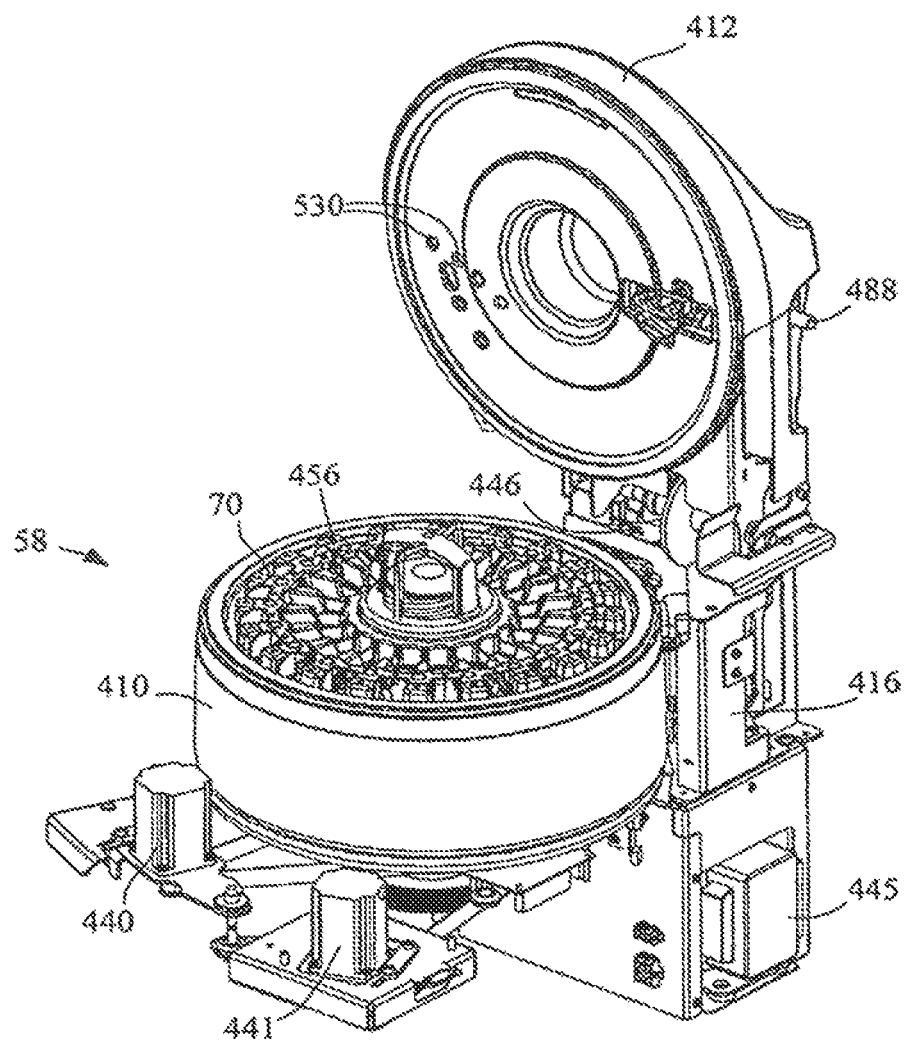

FIGS. 13A-C depict a RV detection mechanism for use in the RV supply assembly of FIG. 12;

FIG. 14 is an illustration of operation of RV the supply assembly of FIG. 12;

FIG. 15 is a block diagram of an RV supply assembly according to the present invention;

FIG. 16 is an illustration of a reaction vessel handler assembly according to an embodiment of the present invention;

FIGS. 17, 18, 19A and 19B are detailed illustrations of a reaction vessel handler and related components;

FIG. 20 is a block diagram depicting an RV handler assembly;

FIG. 21 shows a reaction vessel according to an embodiment of the present invention;

FIG. 22 is a perspective view of a sample handler assembly according to an embodiment of the present invention;

FIG. 23 is a cross-sectional view of a sample aspiration probe and clean station according to an embodiment of the present invention;

FIG. 24 is a block diagram depicting a sample handler robot;

FIGS. 25 and 26 are perspective view of a reagent storage assembly according to an embodiment of the present invention.

Figure 2:
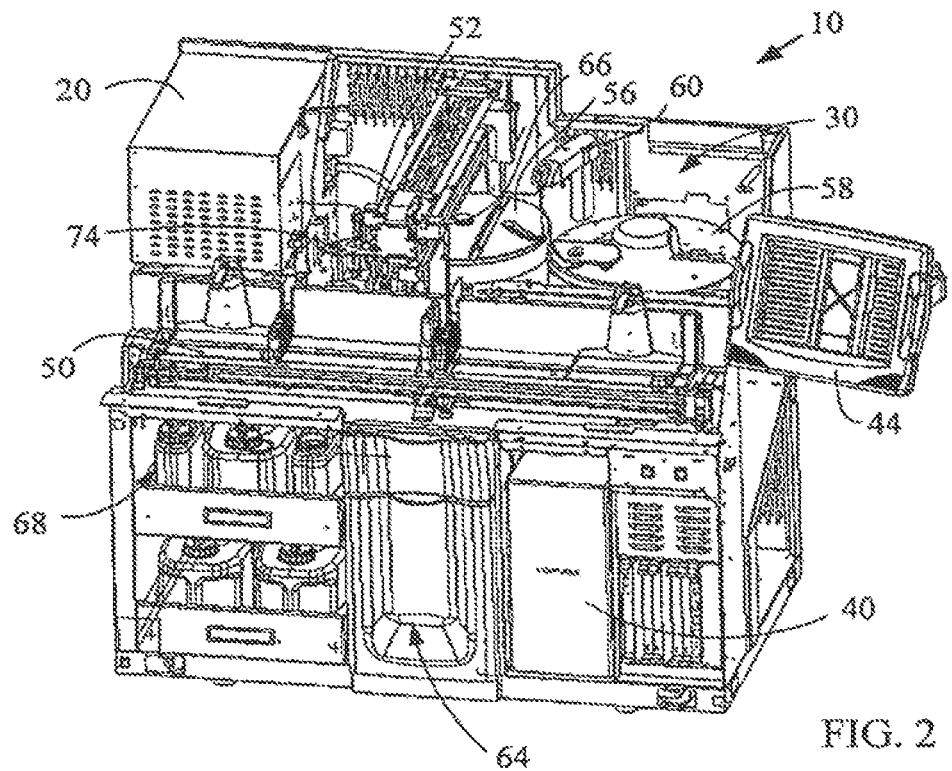
FIG. 2 is an perspective view of a MAD system according to an embodiment of the present invention, partially disassembled to show component modules and subsystems.
Figure 27A:
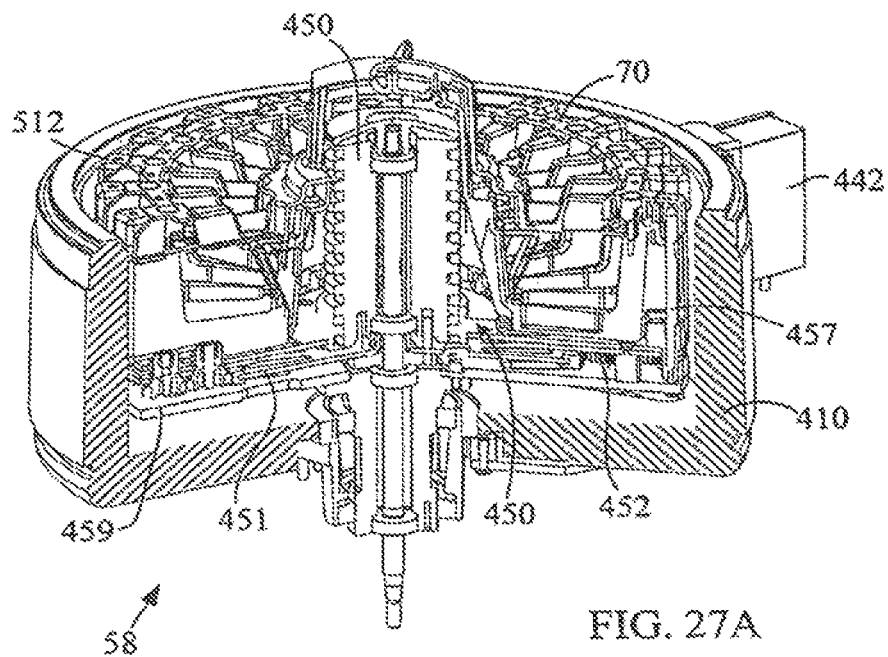
Figure 27B:
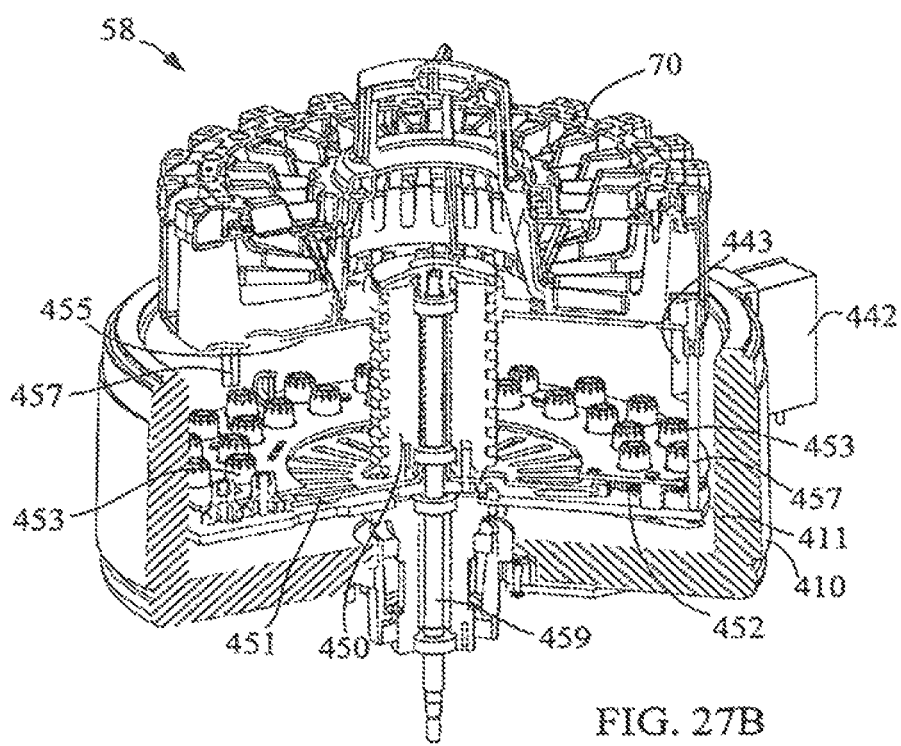
Figure 28A:
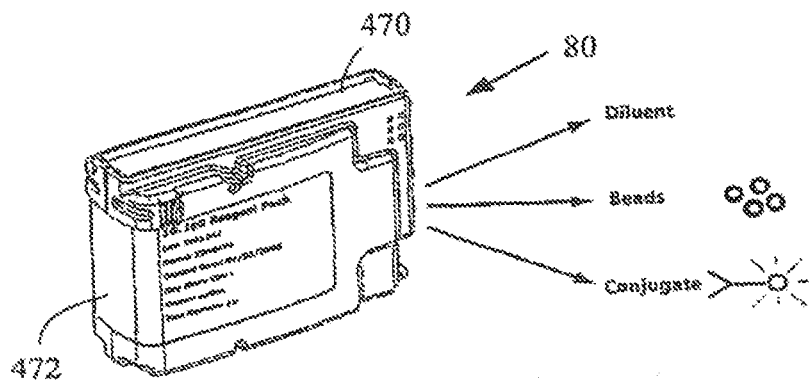
Figure 28B:
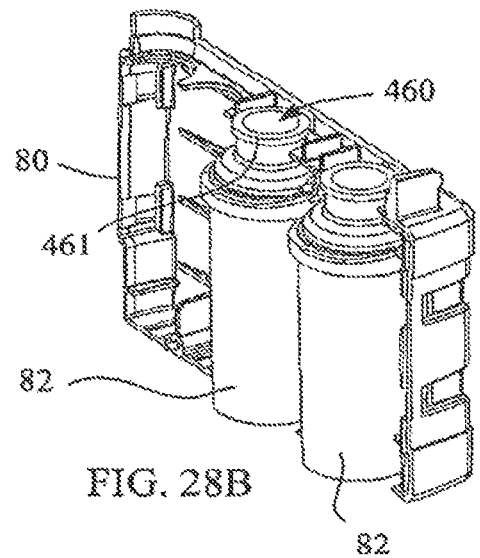
Figure 28C:
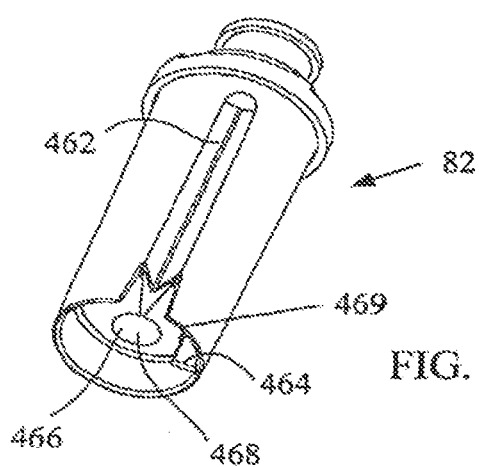
Figure 29A:
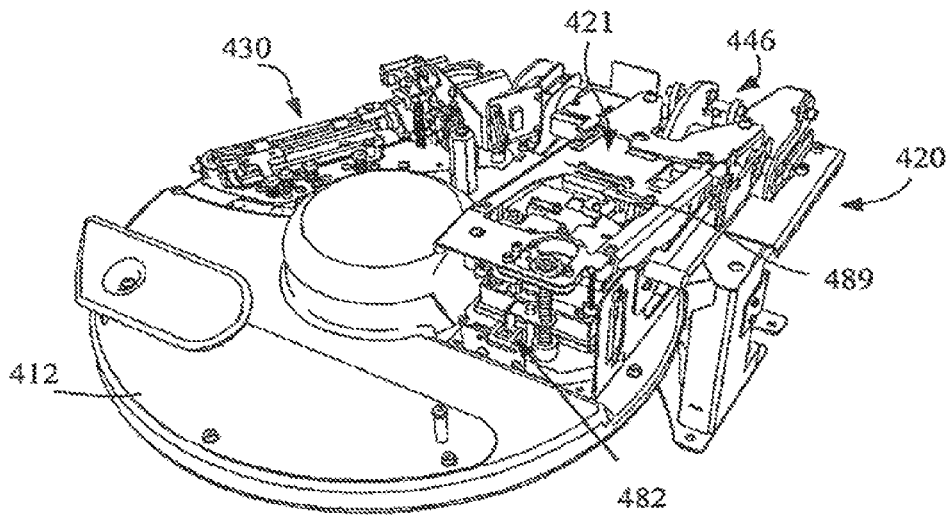
Figure 29B:
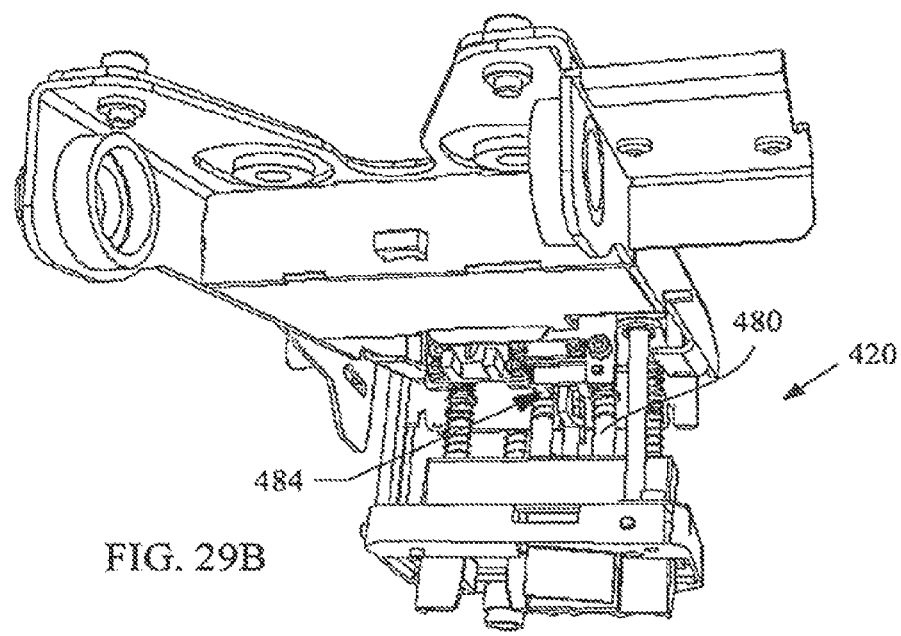
Figure 29C:
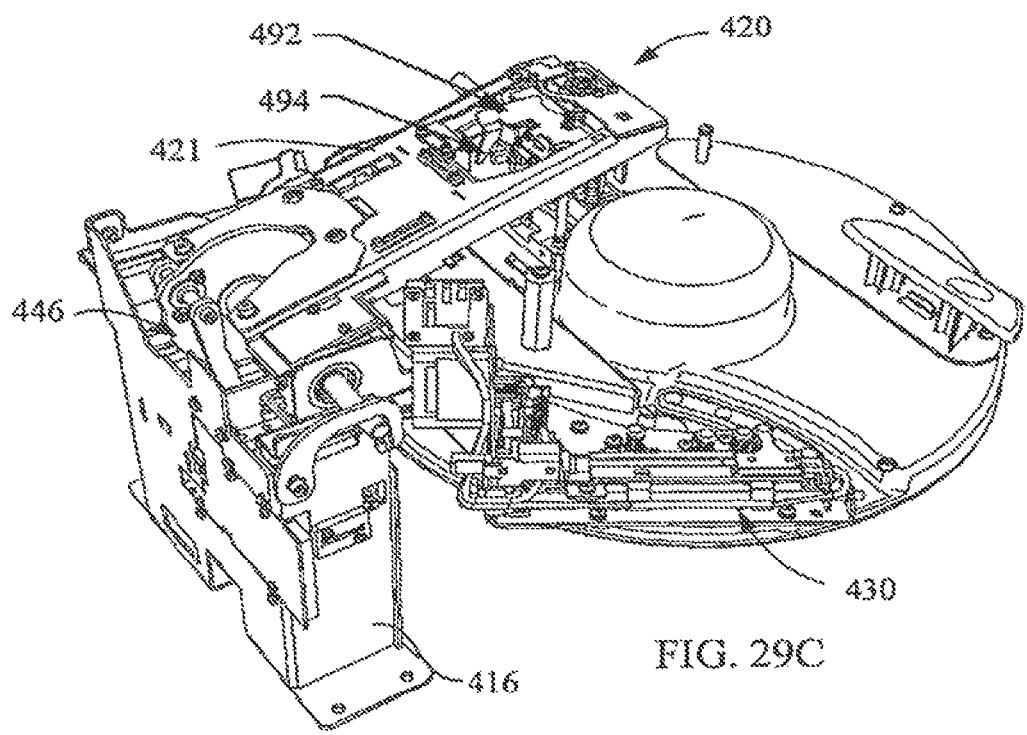
Figure 30:
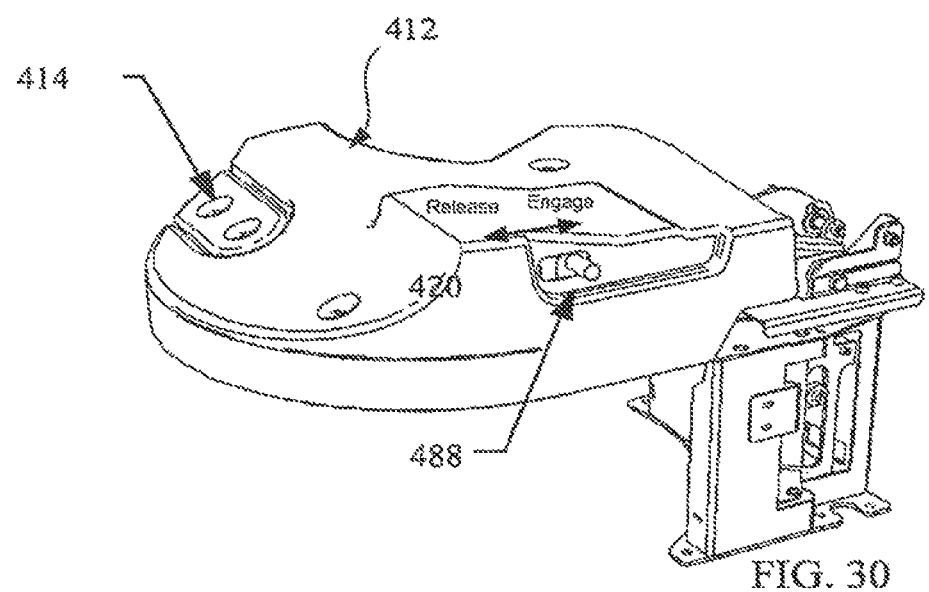
Figure 31A:
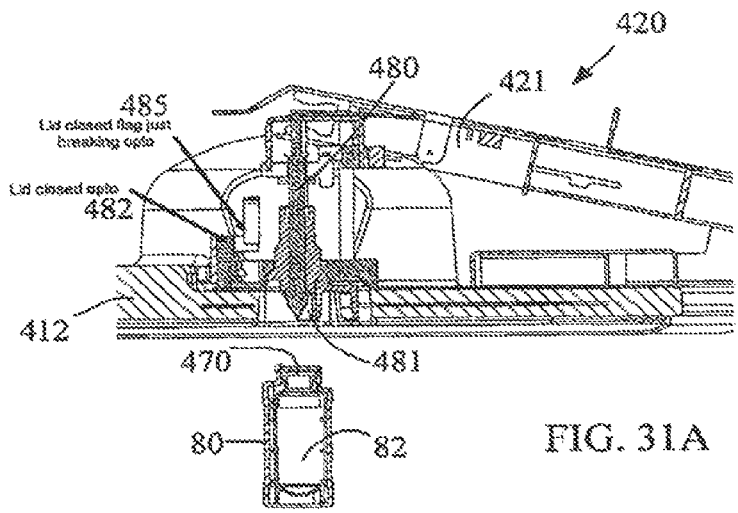
Figure 31B:
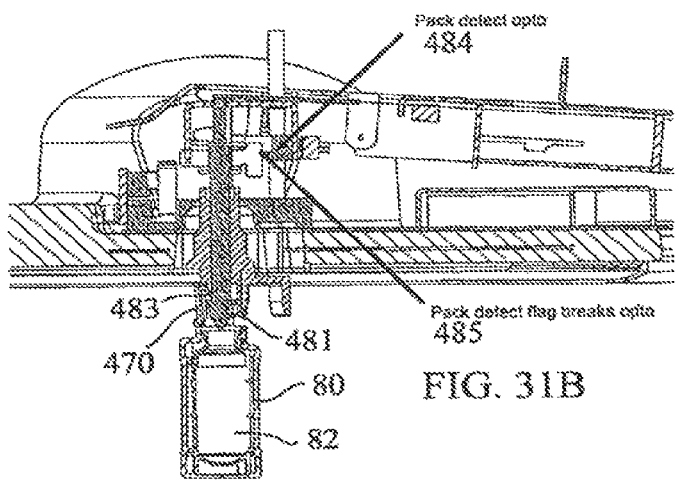
Figure 31C:
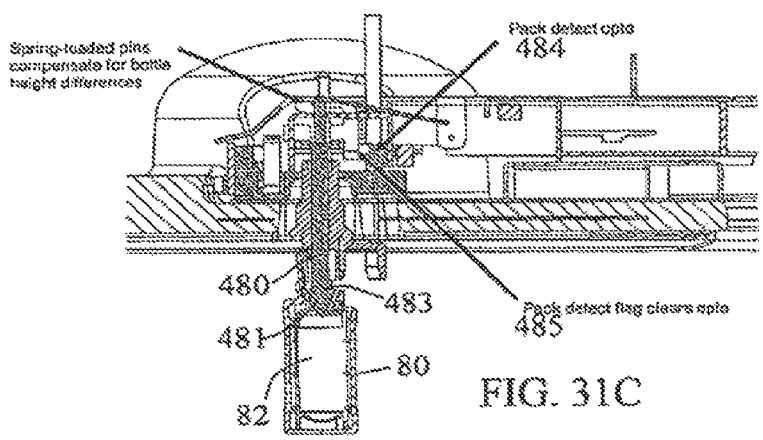
Figure 32:
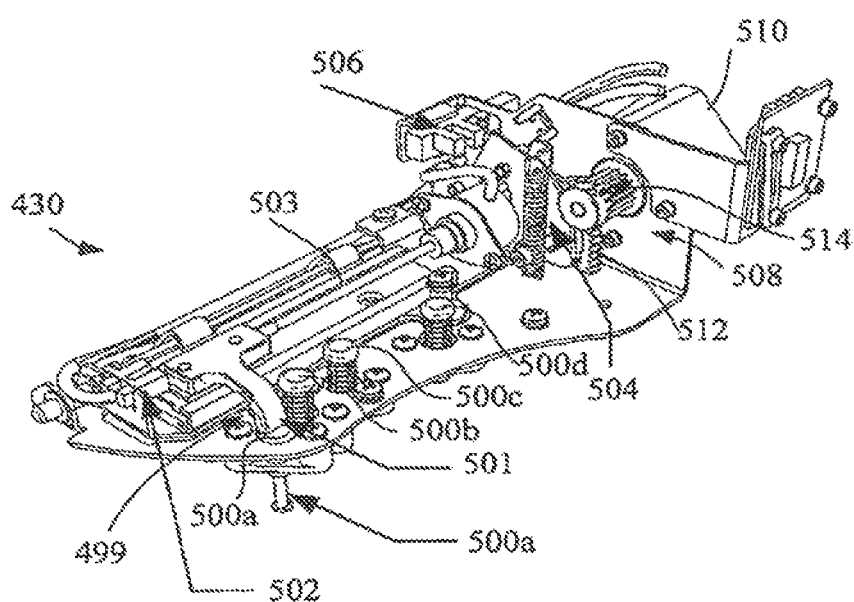
Figure 33:
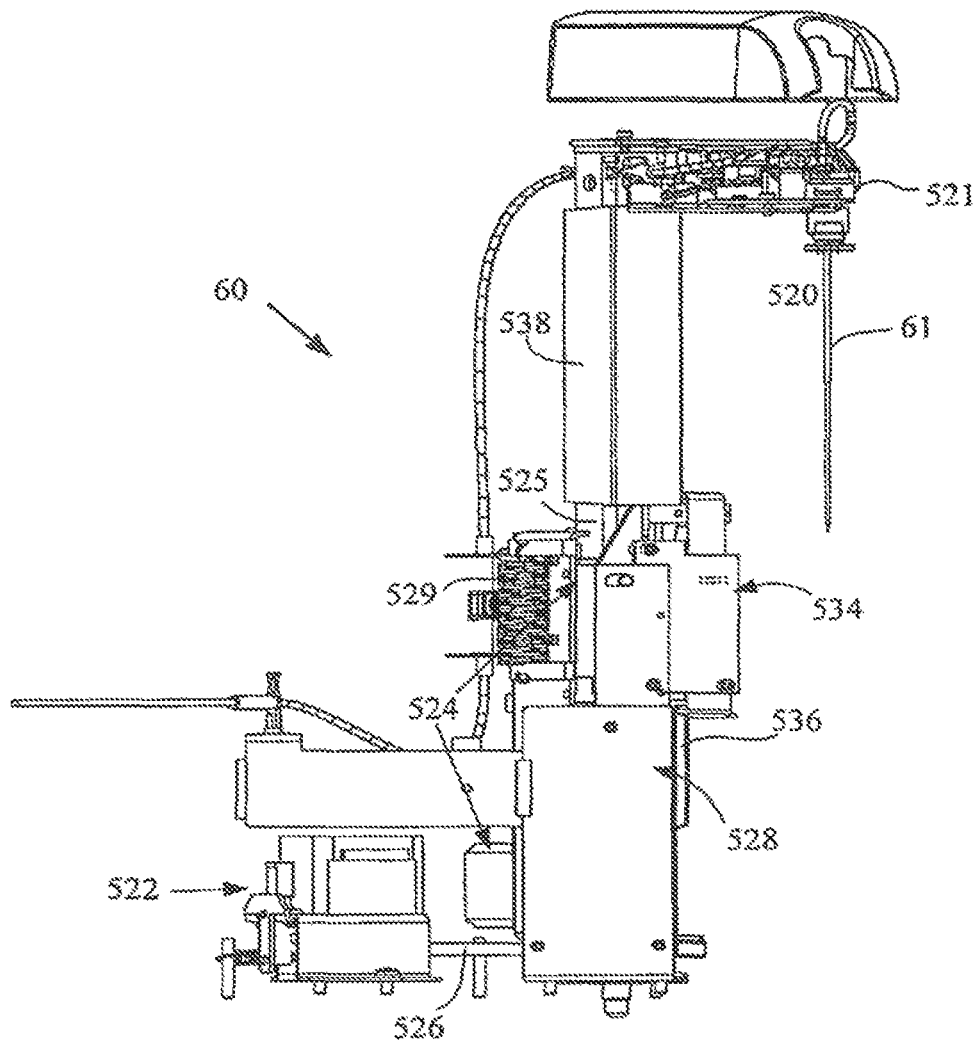
Figure 34:
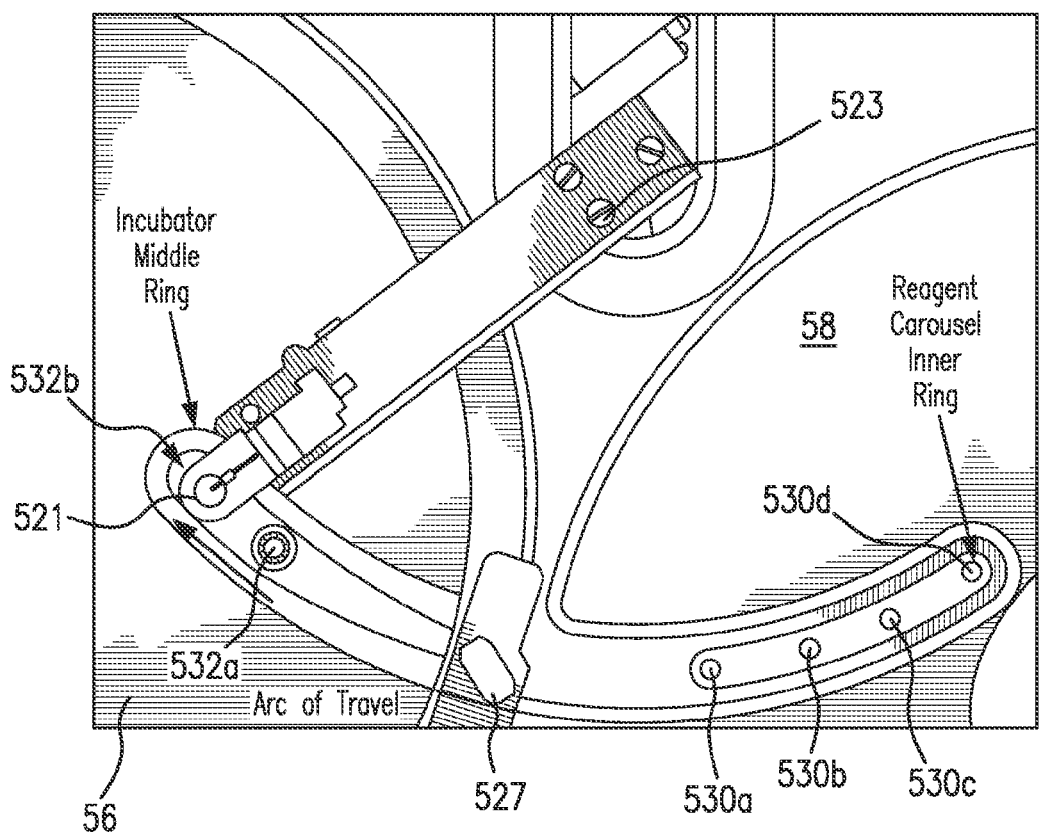
Figure 35:
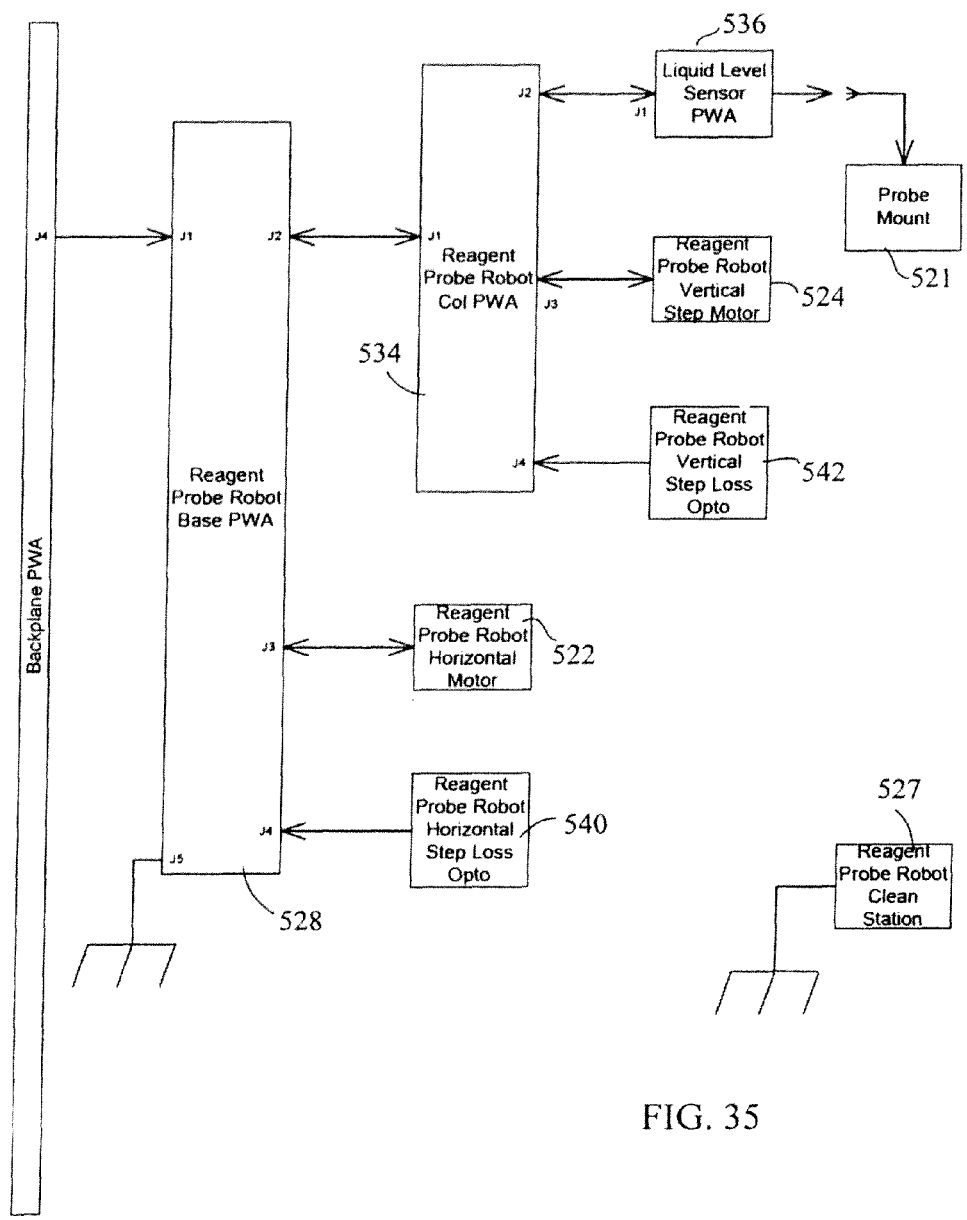
Figure 36:
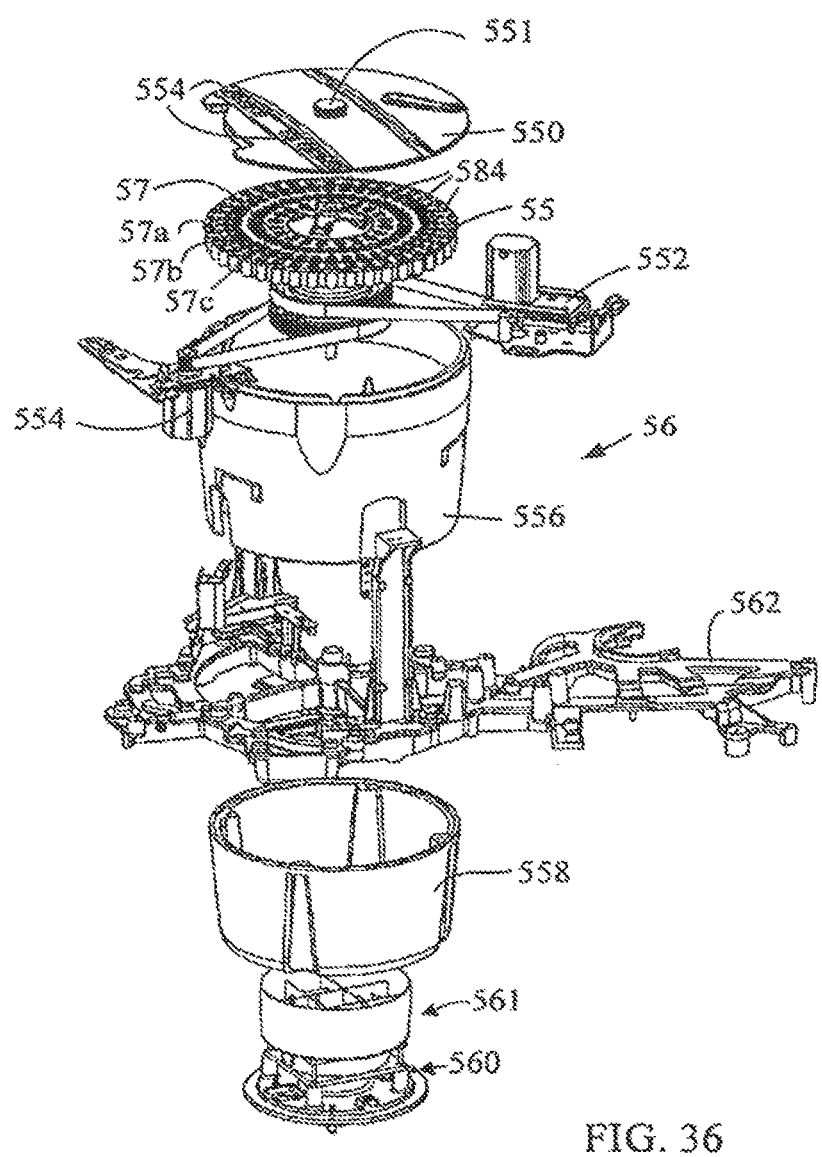
Figure 37:
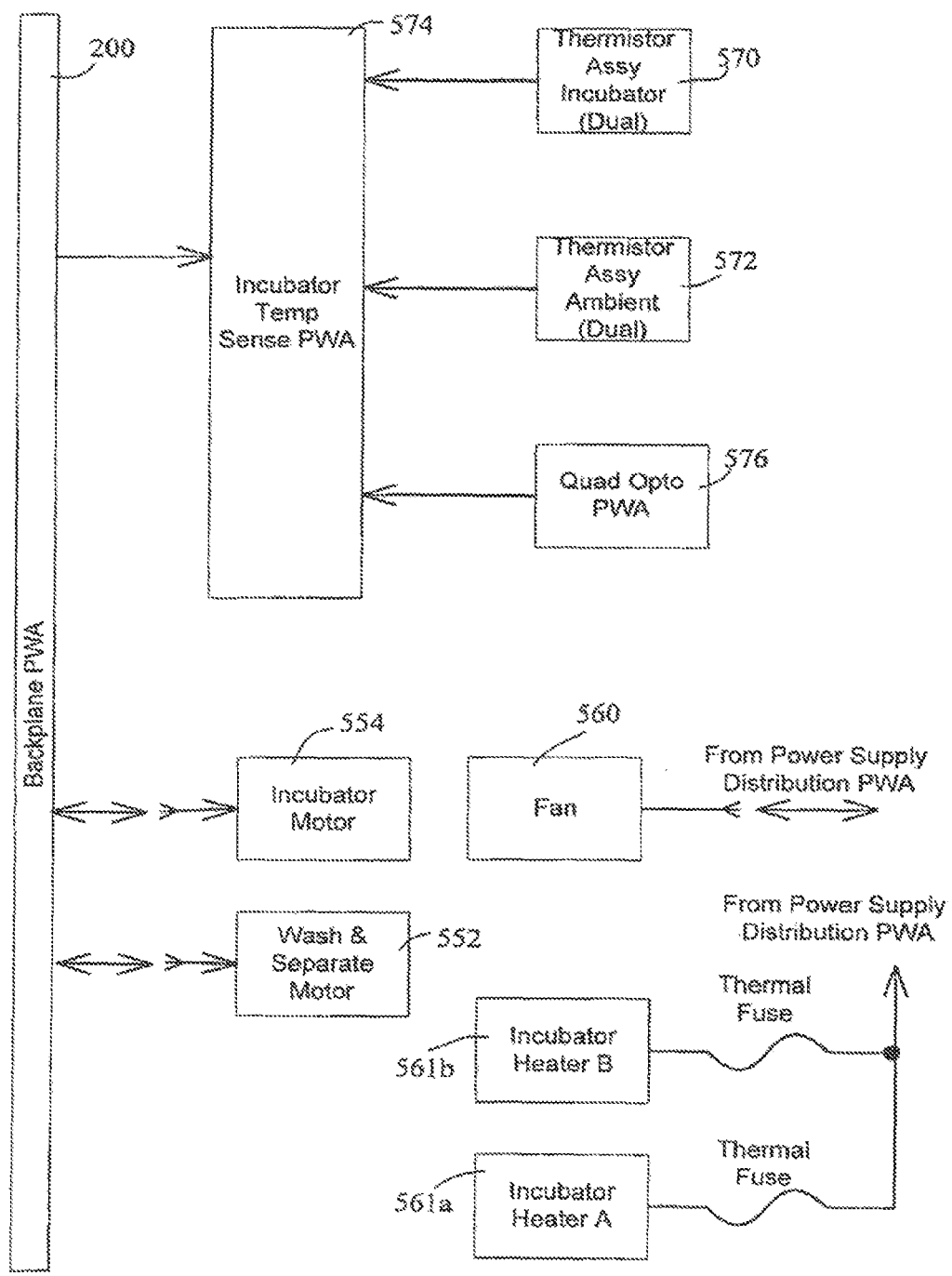
Figure 38:
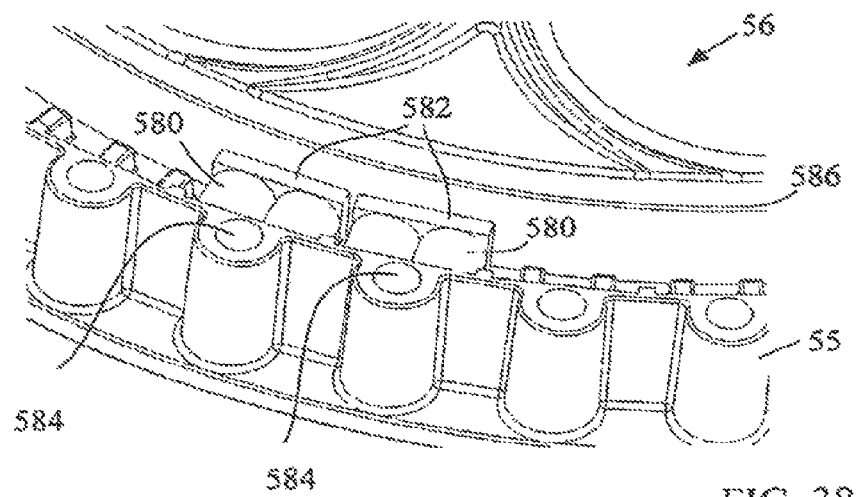
Figure 39:
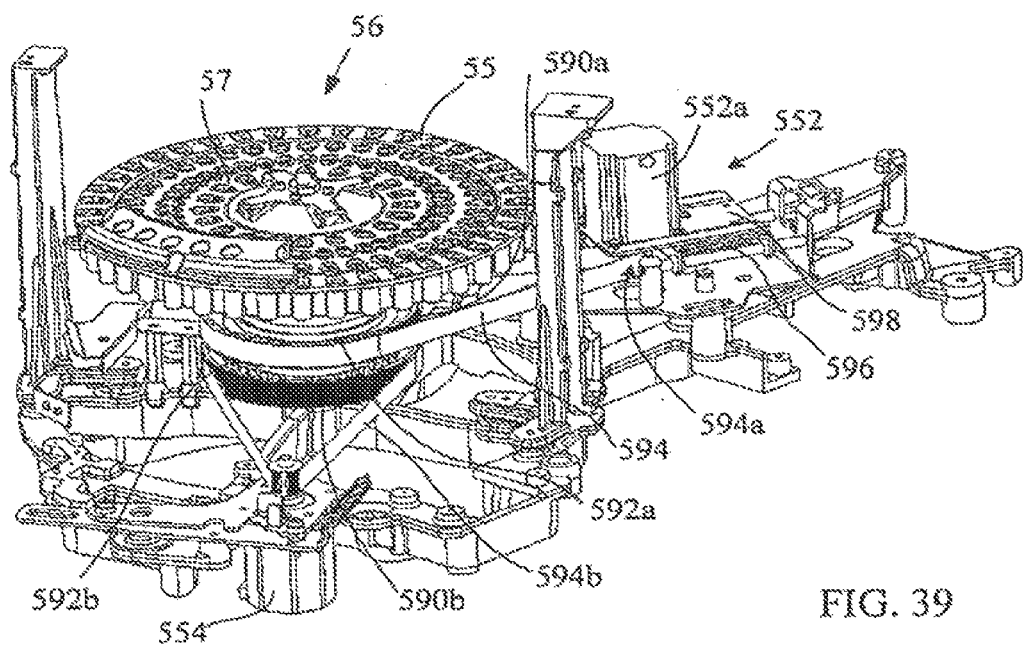
Figure 40:
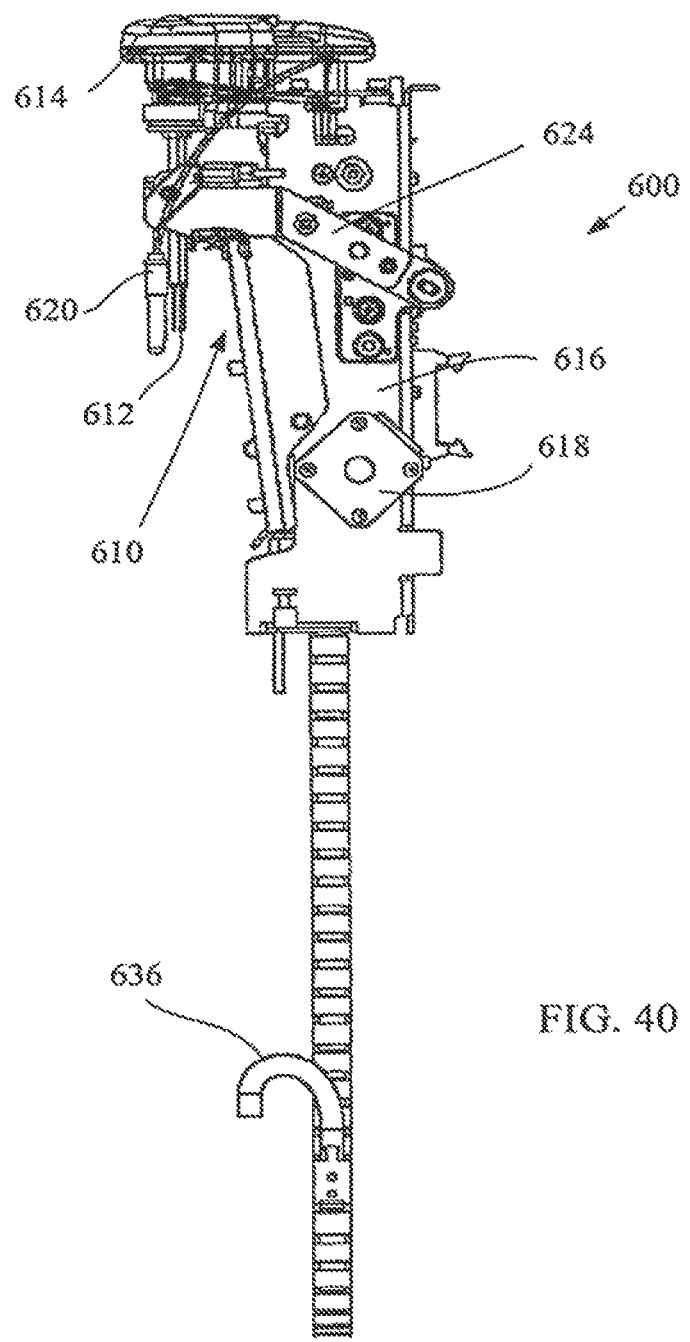
Figure 41:
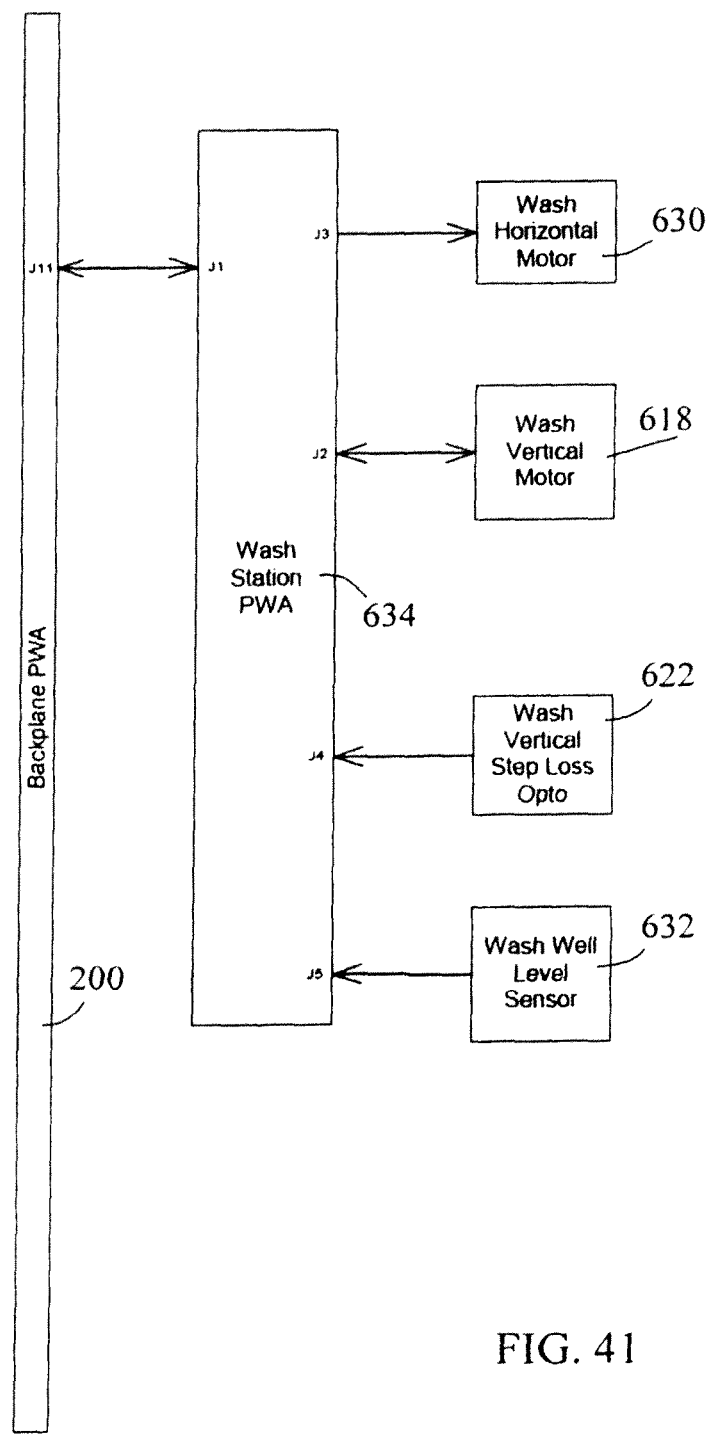
Figure 42:
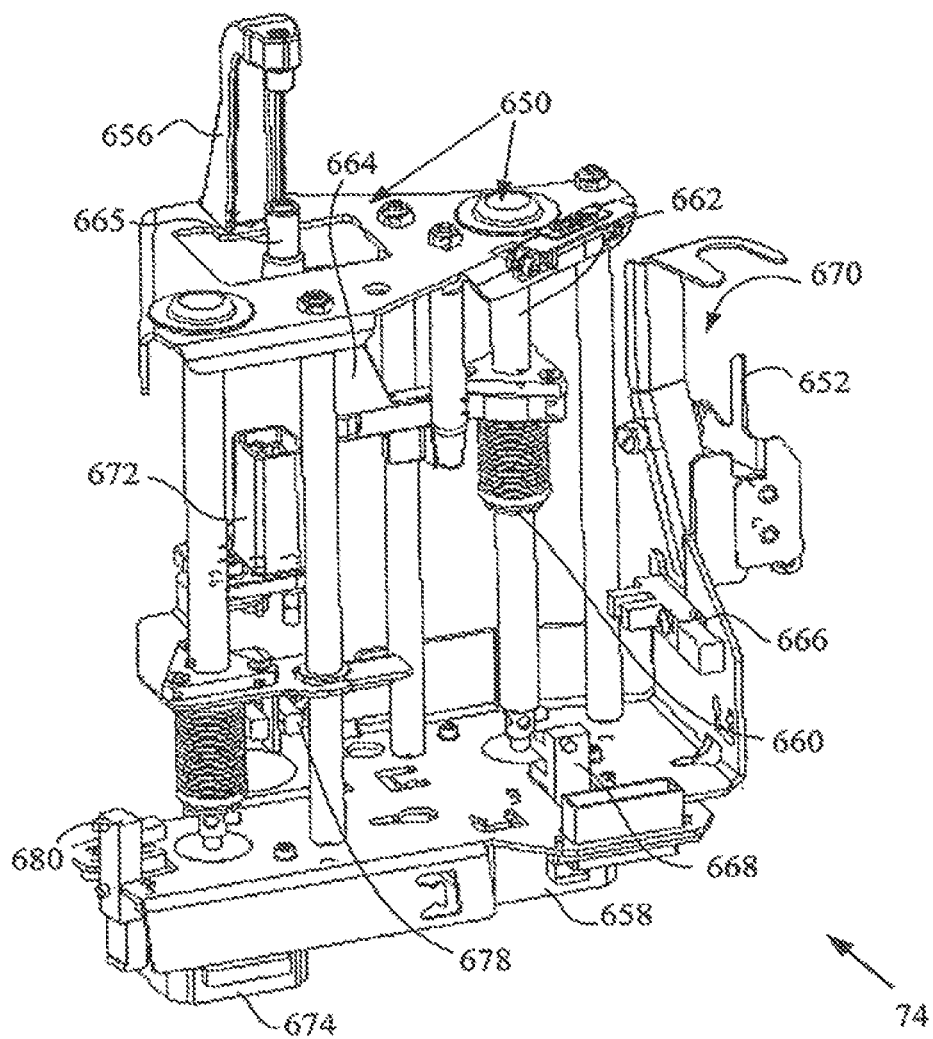
Figure 43:
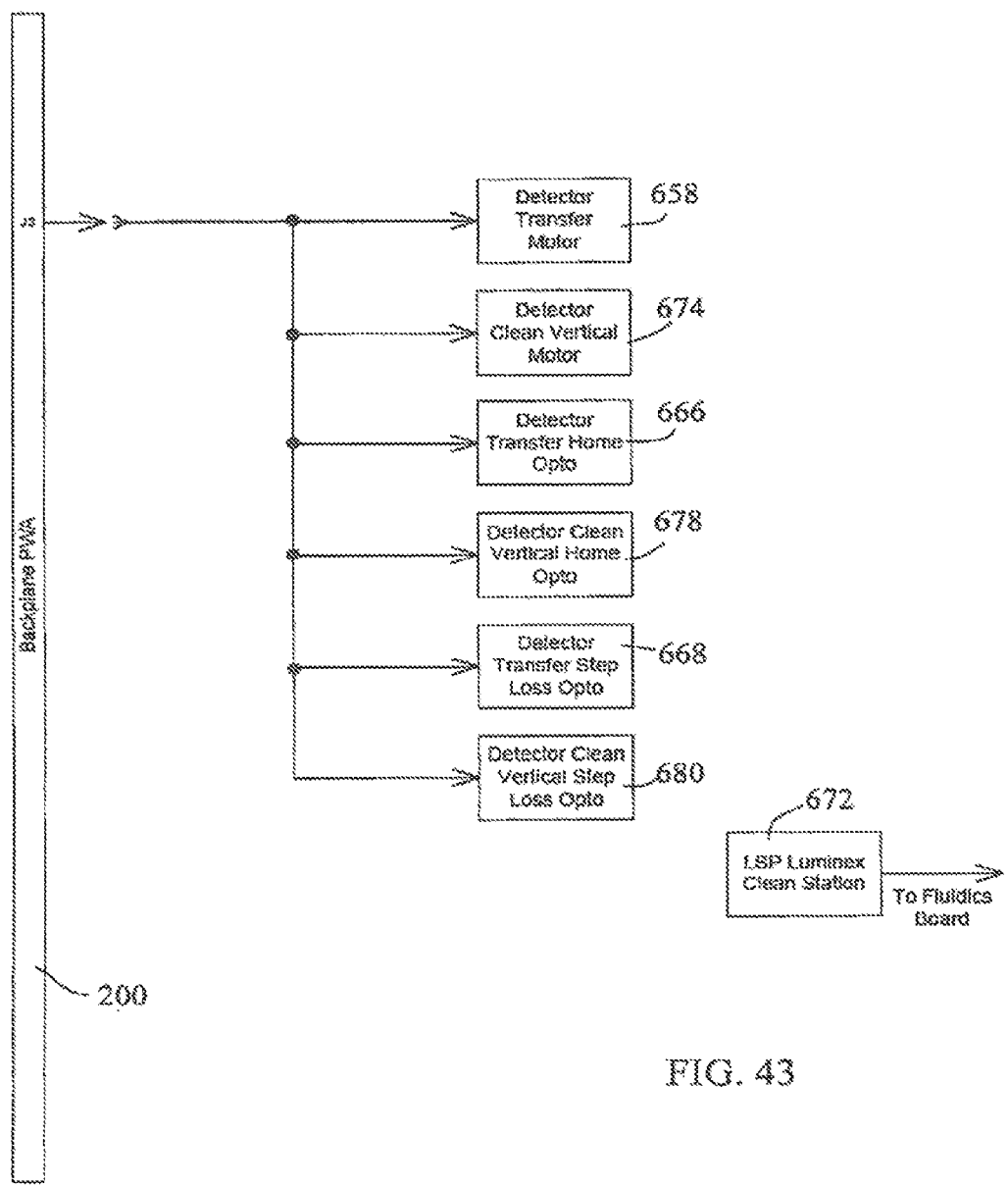
Figure 44A:
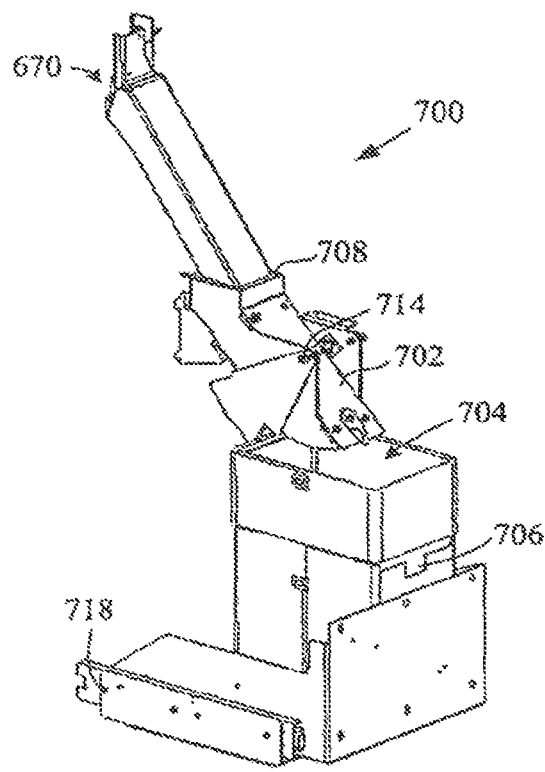
Figure 44B:
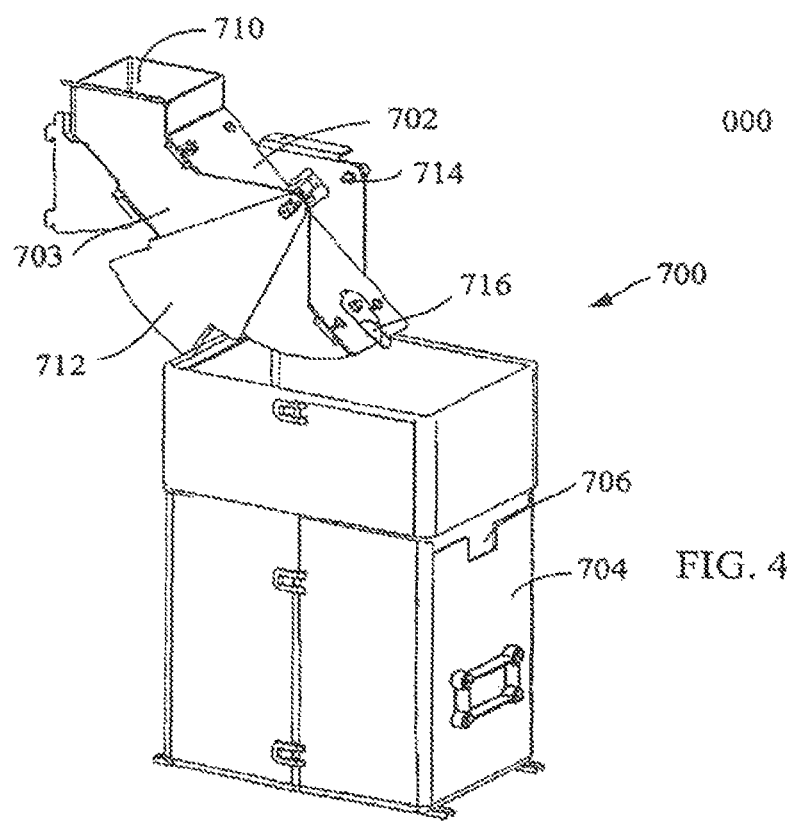
Figure 45:
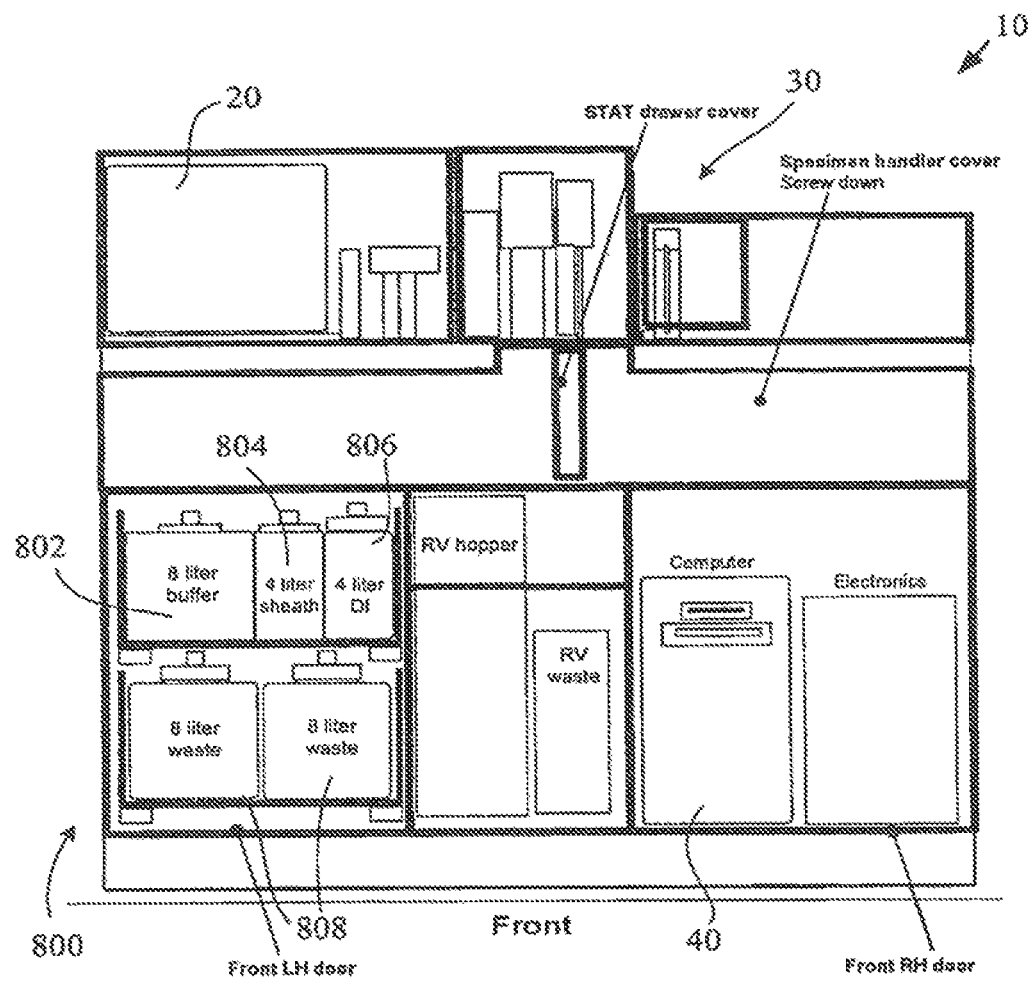
Figure 46A:
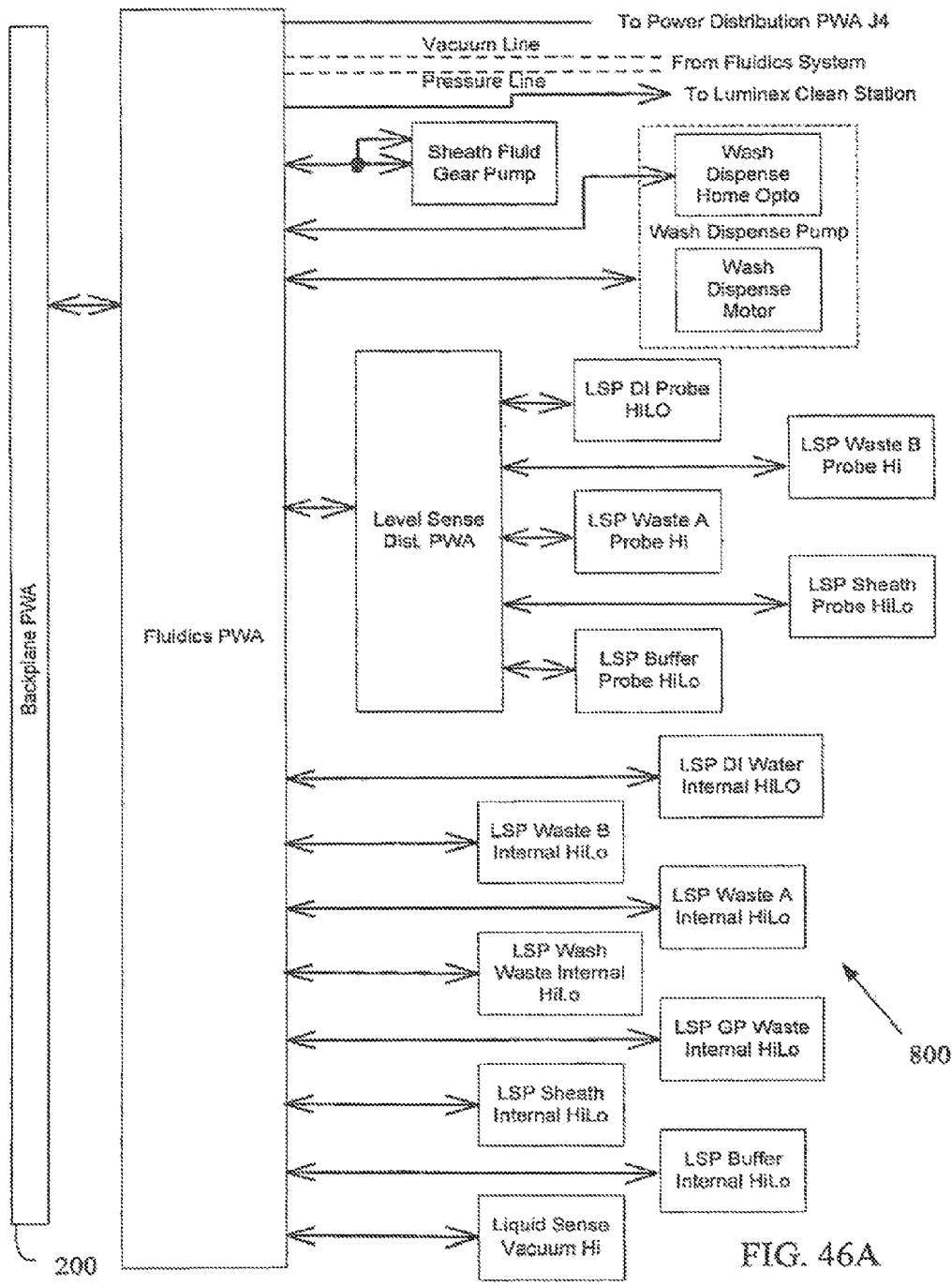
Figure 46B:
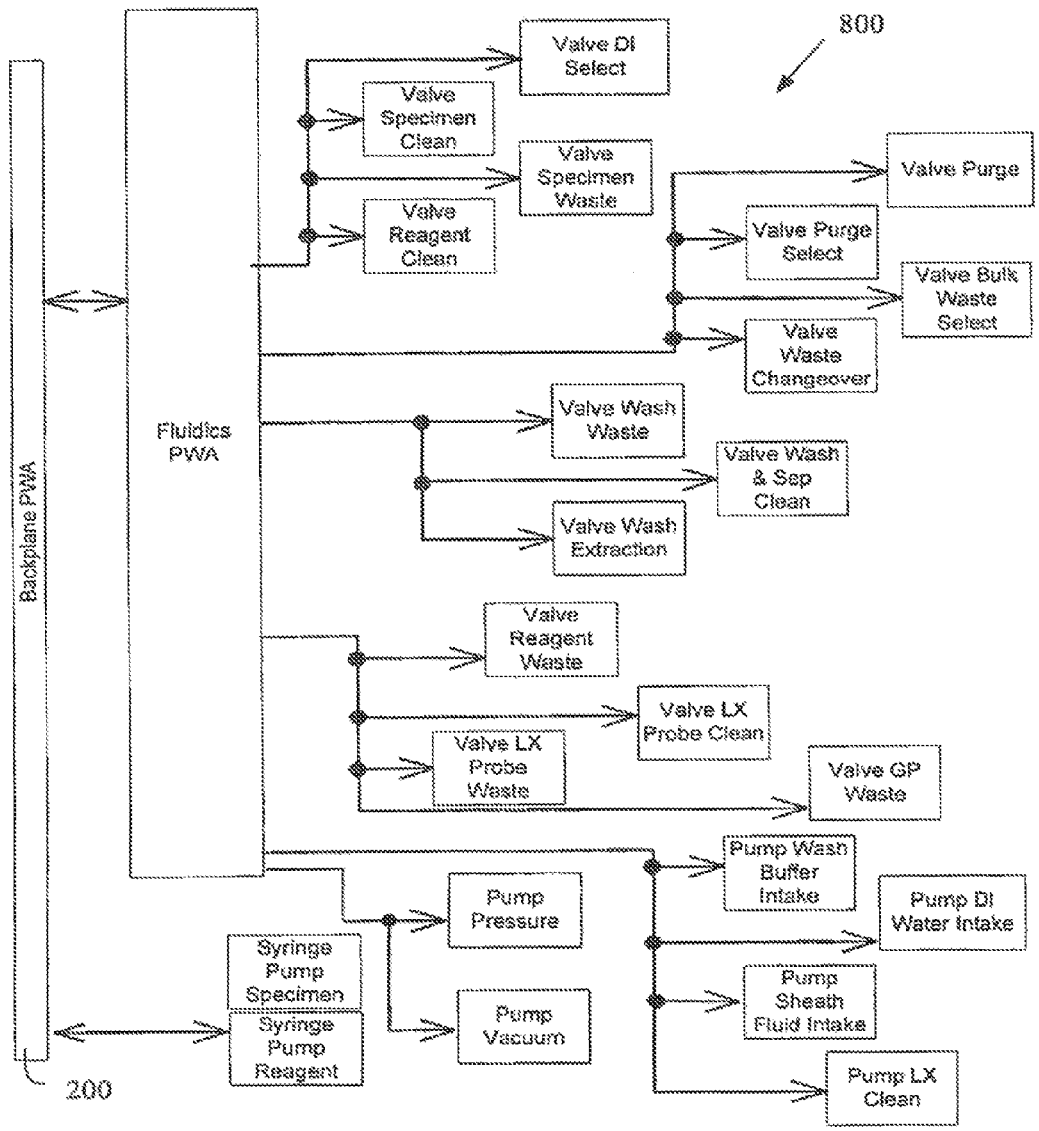
Figure 47A:
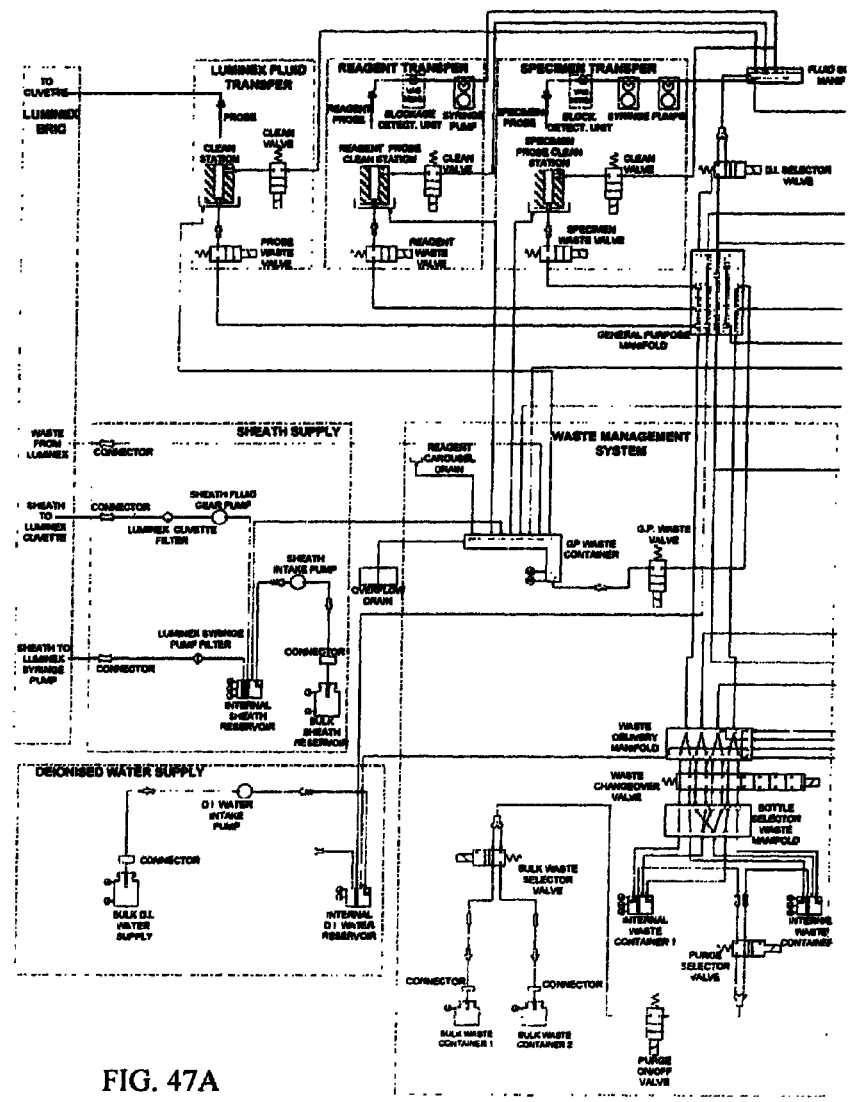
Figure 47B:
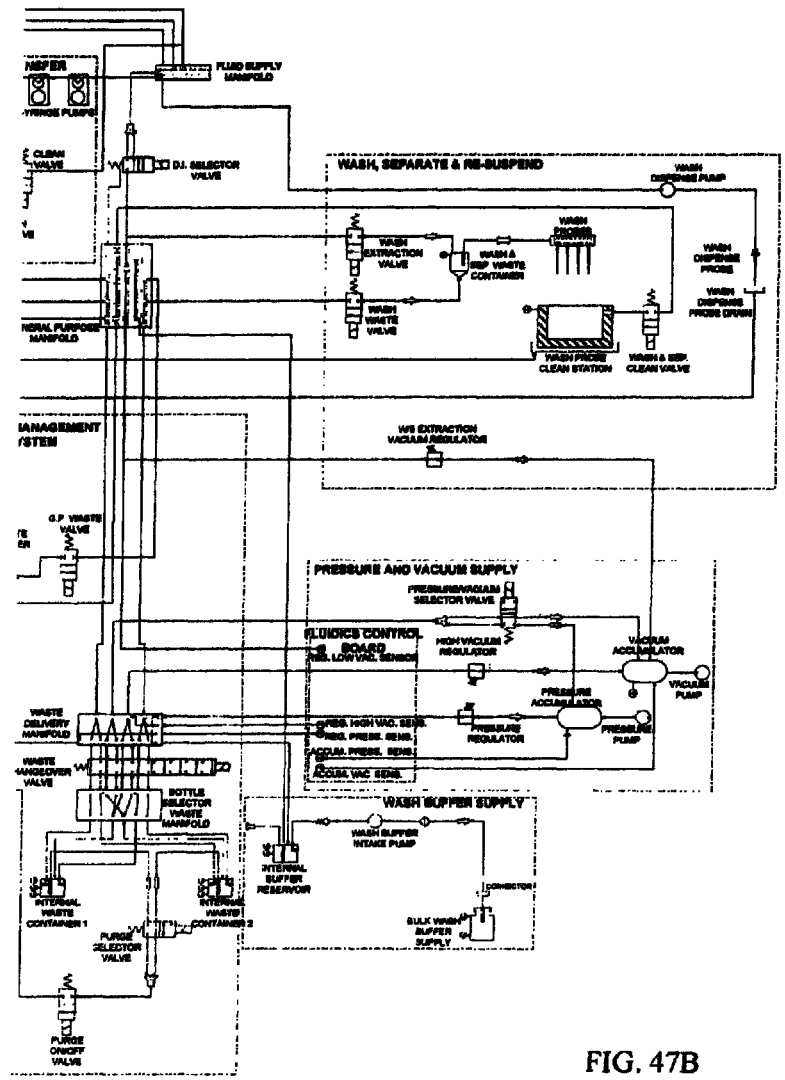
Figure 48A:
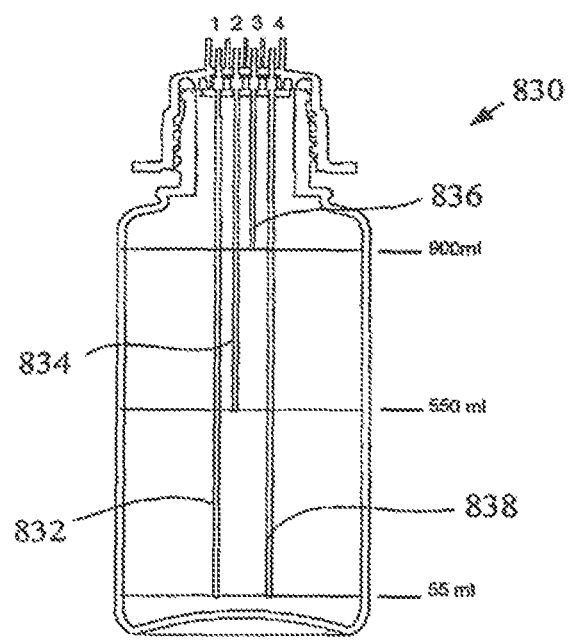
Figure 48B:
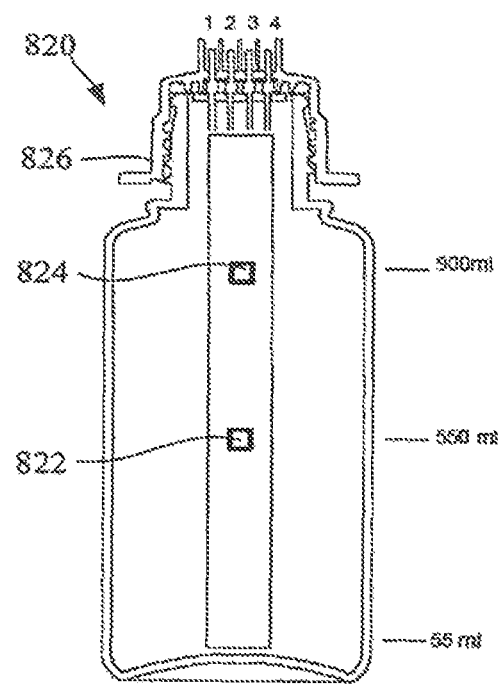
Figure 49:
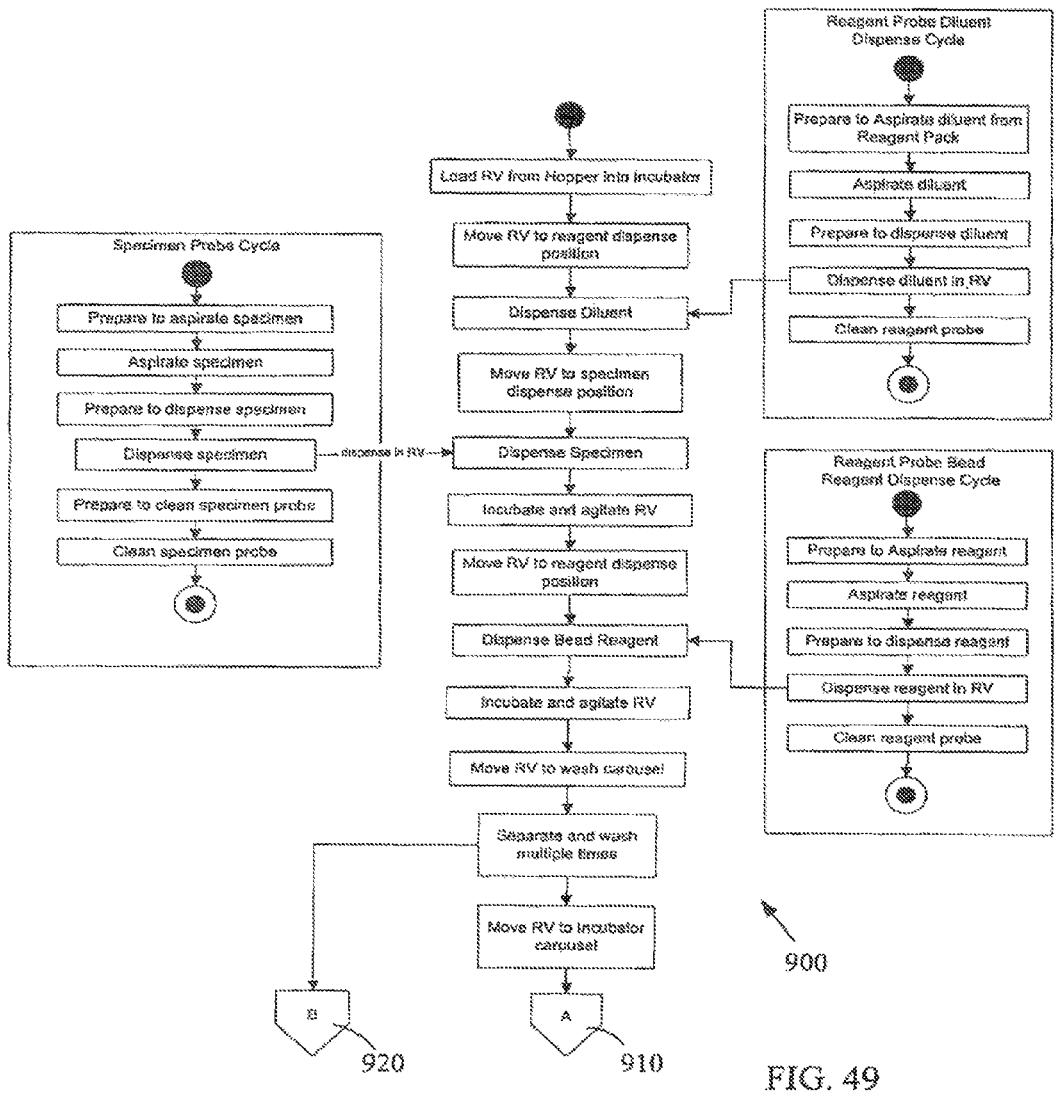
Figure 50:
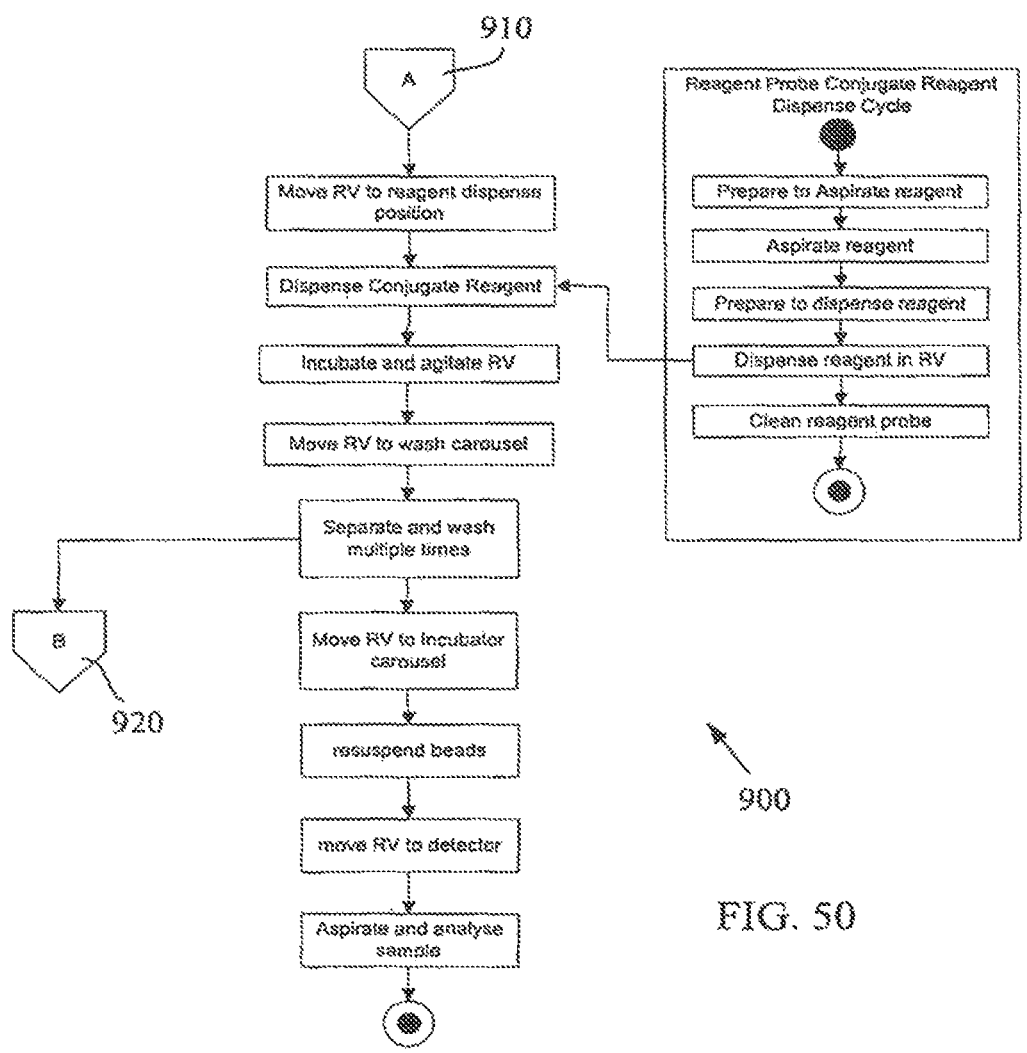
Figure 51:
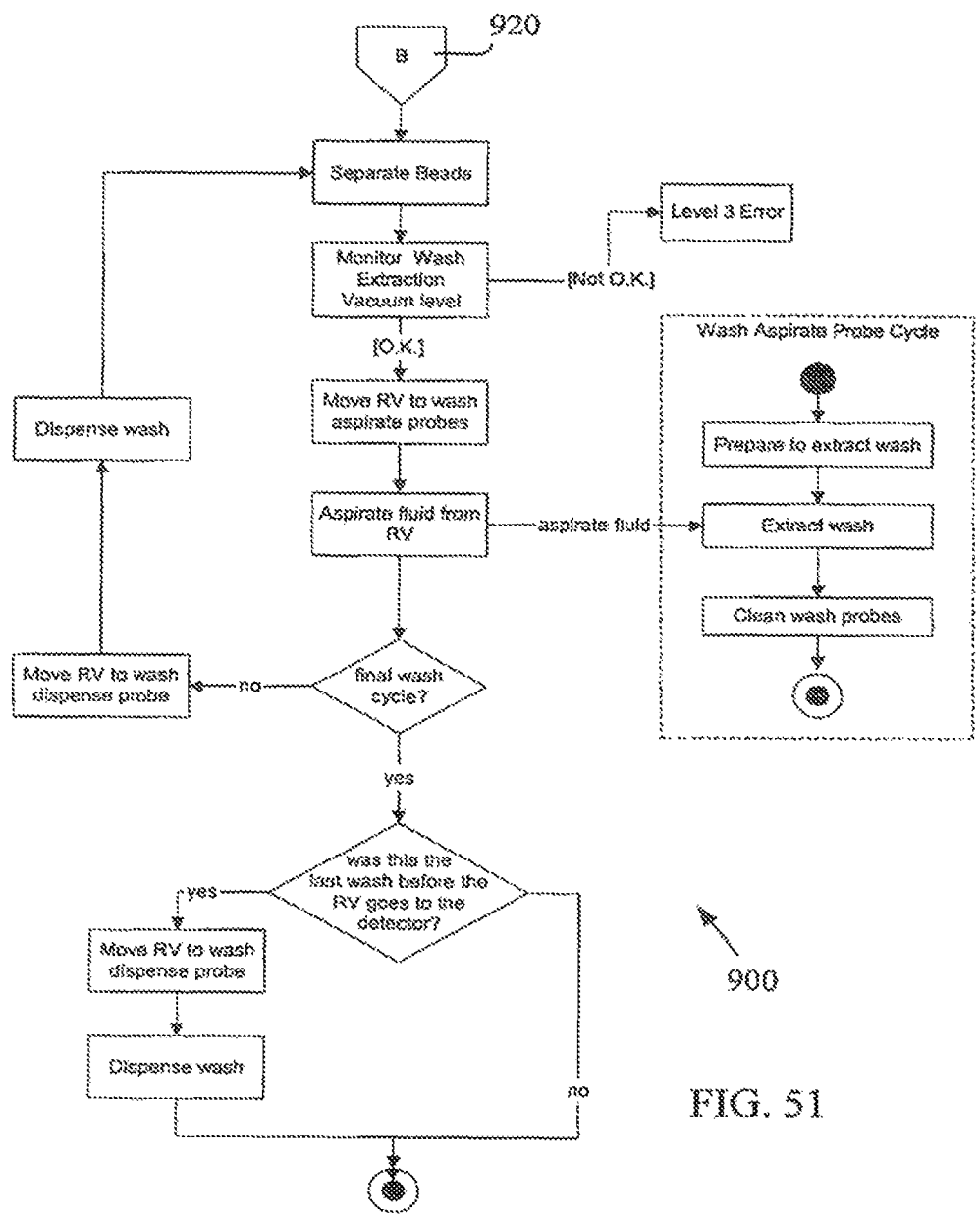
Figure 52:
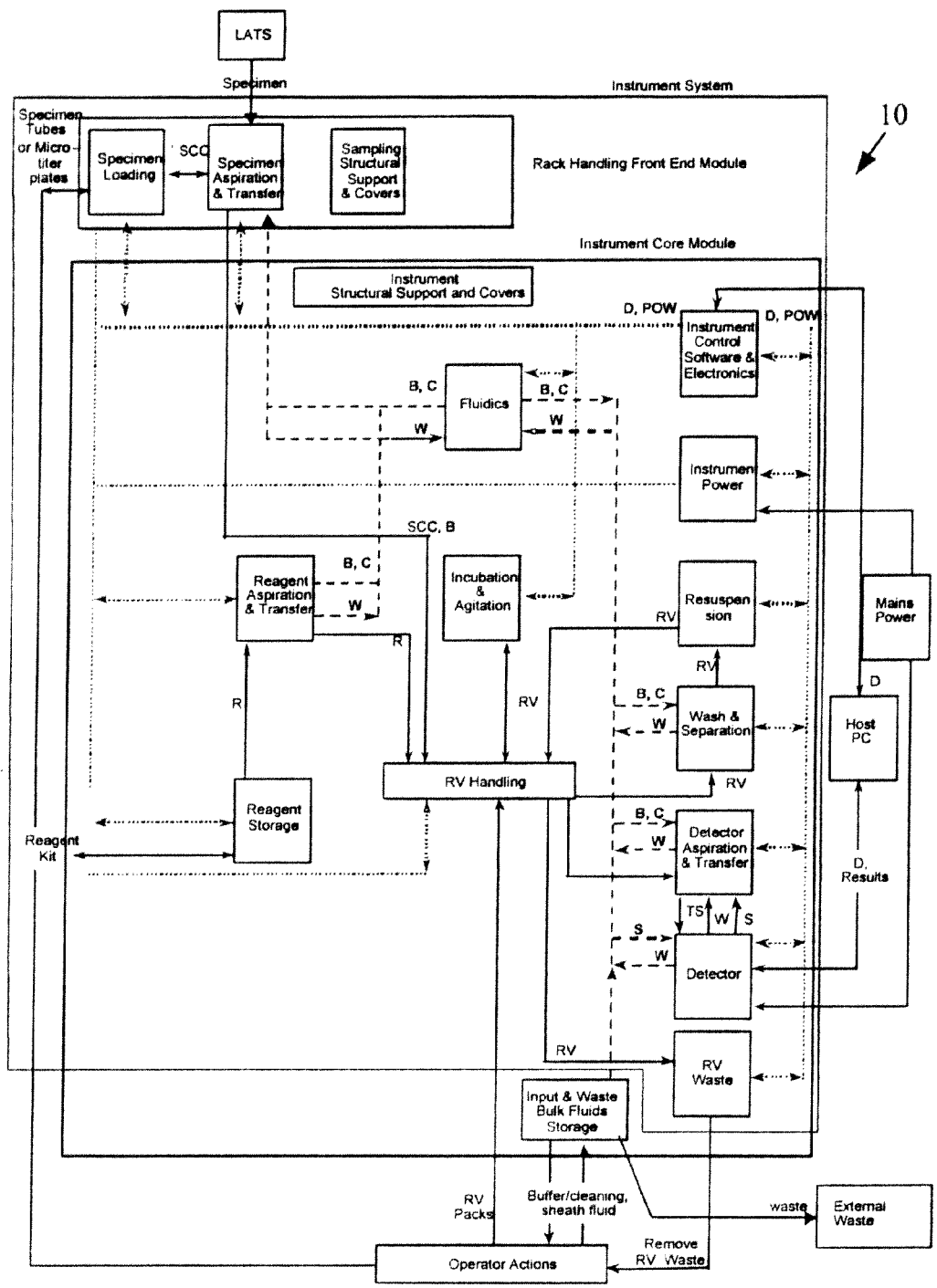

FIGS. 27A and 27B are cross-sectional perspective views of the reagent storage assembly of FIG. 25;

FIGS. 28A-C show a reagent pack and bottles according to an embodiment of the present invention;

FIGS. 29A-C show a reagent pack piercer according to an embodiment of the present invention;

FIG. 30 shows a reagent storage assembly clutch mechanism according to an embodiment of the present invention;

FIGS. 31A-C are cross-sectional side views showing operation of the pack piercer of FIGS. 29A-C;

FIG. 32. is a perspective view of a reagent pack lid opener according to an embodiment of the present invention;

FIG. 33 is a perspective view of a reagent robot assembly according to an embodiment of the present invention;

FIG. 34 is a top view of the reagent robot of FIG. 33, showing a range of movement;

FIG. 35 is a block diagram of the reagent robot assembly of FIG. 33;

FIG. 36 is an exploded perspective view of an incubator and separation carousel assembly according to an embodiment of the present invention;

FIG. 37 is a block diagram of the incubator and separation carousel assembly of FIG. 36;

FIG. 38 is an illustration depicting a separation mechanism employed in an embodiment of the incubator and separation carousel assembly of FIG. 36;

FIG. 39 is a perspective view of a partially assembled incubator and separation carousel assembly of FIG. 36;

FIG. 40 shows a wash station according to an embodiment of the present invention;

FIG. 41 is a block diagram of a wash station according to an embodiment of the present invention;

FIG. 42 is a perspective view of a detector transfer robot assembly according to an embodiment of the present invention;

FIG. 43 is a block diagram depicting the detector transfer robot;

FIGS. 44A and 44B depict a reaction vessel waste assembly according to an embodiment of the present invention;

FIG. 45 is a close up perspective view of the MAD system of FIG. 2, showing containers and other components of a fluidics system;

FIGS. 46A and 46B are block diagrams of a fluidics system according to the present invention;

FIGS. 47A and 47B are detailed schematic diagrams of a fluidics system according to the present invention;

FIGS. 48A and 48B are illustrations of different embodiments of fluid reservoirs with liquid level sensors;

FIGS. 49-51 are flow charts depicting an example of a method of use of a MAD system for performing a serology IgG assay panel; and FIG. 52 is a detailed functional block diagram of a MAD system according to the present invention.

Like reference numerals refer to corresponding parts throughout the several views of the drawings.

5. DETAILED DESCRIPTION OF THE INVENTION

5.1 Overview of the Multi-Analyte Detection ("MAD") System

A general overview of the technology employed in the system follows. It should be appreciated by one of ordinary skill in the art that the following description of the technology employed in the system is intended as exemplary and educational and is not intended to limit the invention. Furthermore, any numerical values, ranges, materials, temperatures, times, or the like, given below are preferred values, not intended to limit the present invention. Following the general description is a more detailed description of each of the modules and various sub-modules and other components.

Figure 1:
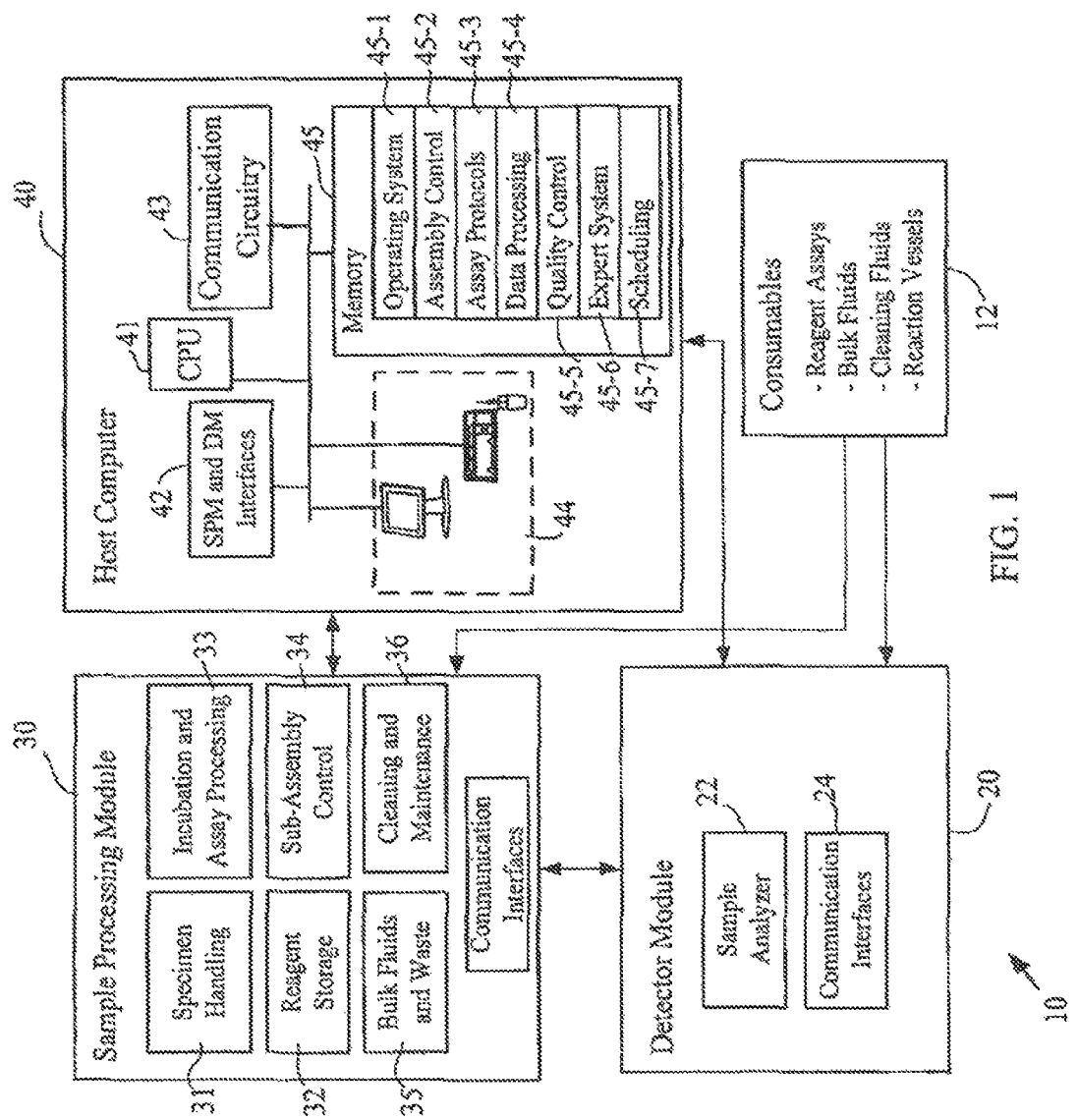
FIG. 1 is a block diagram showing general features of a multi-analyte detection ("MAD") system according to an embodiment of the present invention.

Referring to FIG. 1, the multi-analyte detection system 10 (also referred to herein as MAD system 10) includes a detector module ("DM") 20, a sample processing module ("SPM") 30, and a host computer 40. Each of these modules 20, 30, 40 includes assemblies, sub-assemblies, and/or components that perform various tasks within the overall system and method of using the MAD. (Note that the terms "assembly" and "sub-assembly" are used throughout to help identify levels of component systems within overall system 10, however such term are not meant to limit the invention and may be used interchangeably.)

For example, sample processing module 30 includes assemblies for specimen handling 31, reagent storage 32, incubation and assay processing 33, control of on-board assemblies and processes 34, storage and delivery of fluids and storage of wastes 35, cleaning and maintenance functions 36, and for communication 36 between and among the various assemblies and modules. Detector module 20 includes an analyzer 22 for analyzing samples processed by SPM 30 and interfaces for communicating with other modules and assemblies and for sending assay data to host 40.

Host computer system 40 is generally responsible for providing oversight of necessary operations from instrument control to results evaluation, data storage, quality control, mainframe bidirectional interfacing, and operator assistance. Specific instrument control activities include movement of samples, pipetting samples, pipetting reagents, flushing samples, analyzing samples, reporting data, and troubleshooting the device.

Host computer 40 preferably includes a processor 41, or central processing unit (CPU) 41, memory 45, interfaces 42 for communicating with modules 20, 30, other communication circuitry 45, and a user interface 44 that can include, e.g., a monitor, a keyboard, a trackball, or mouse, and/or a touch screen for data entry. Host computer system 40 also preferably, although not necessarily, includes a printer or other peripheral output devices. Memory 45 includes software and data for performing various operations and control of system 10. For example, memory 45 typically includes software modules such as: an operating system 45-1; one or more assembly control modules 45-2 including instructions for operation and control of modules 20, 30 and other subsystems and components of system 10; assay protocols 45-3; analyzing, processing and storing data 45-4; quality control 45-5; an expert system 45-6 and a instructions and data related to scheduling 45-7 of assays and procedures.

Referring to FIG. 2, a preferred embodiment of MAD system 10 is a self contained, fully automated random assay system incorporating a sample processing module 30 having a number of automated assemblies and components for processing samples and a detector module 20 for analyzing the samples.

MAD system 10 is capable of multiplexing a number of assays in the same reaction tube and preferably employs a multiplexed bead-based chemistry system for performing numerous assays. For example, in one embodiment, system 10 is capable of performing up to 25 or more individual assays, in another embodiment up to 100 individual assays, and in yet another embodiment more than 100 individual assays simultaneously in a single reaction vessel.

Generally, detector module 20 utilizes an advanced analyzer to detect the presence of analytes, such as antigens, antibodies receptors, peptides, oligonucleotides, DNA, RNA, small molecules, viruses, viroids, cells, and the like, in patient samples by integrating the technologies of fluoroimmunoassay and flow cytometry. This combination of advanced technologies allows system 10 to perform, e.g., at least 200 measurements per analyte per specimen, and about 100,000 measurements per minute, yielding up to about 2,200 results per hour. Detector module 20 incorporates a flow cytometer that detects labeled microspheres or beads in a sample, and communicates with hardware and software in host computer 40 for assay control and data analysis. Optionally, detector module 20 incorporates its own computer processor and memory for providing some level of control and analysis and communicating with host 40.

In a preferred embodiment a flow cytometer of detector module 20 analyzes individual microspheres by size and fluorescence, distinguishing preferably three fluorescent colors, green (550-610 nm emission), orange (585-650 nm emission), and red (>650 nm emission), simultaneously. Microsphere size, determined by 90-degree light scatter, is used to eliminate microsphere aggregates from the analysis. Orange and red fluorescence are used for microsphere classification, and green fluorescence is used for quantification of analyte. Additional details and examples of detector module 20 are described in section 5.2 below.

Figure 3:
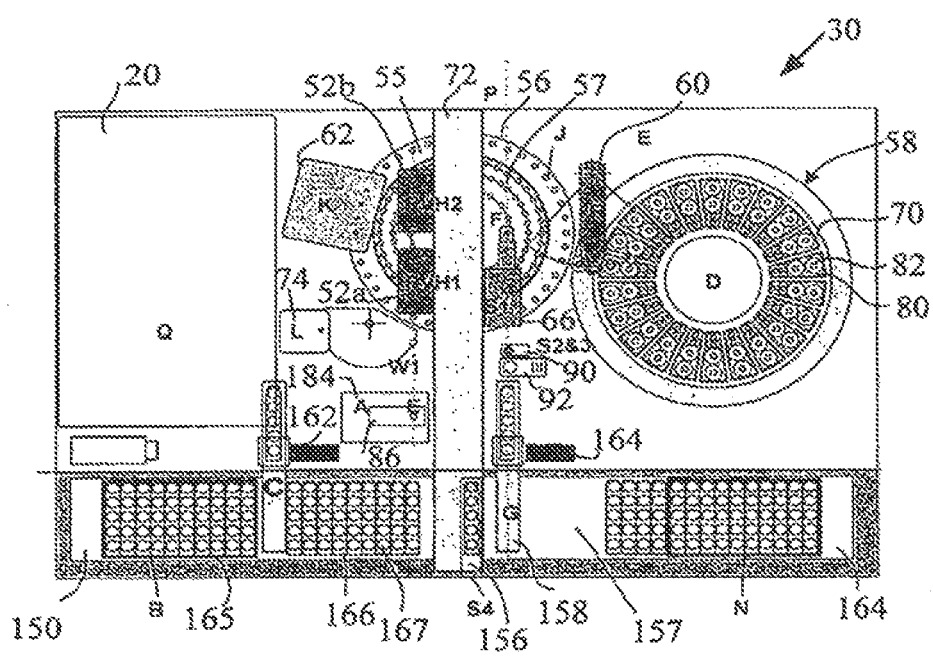
FIG. 3 is a top schematic view of the MAD system of FIG. 2.

Major assemblies and components of sample processing module 30 include a specimen rack handler assembly 50, a reaction vessel handler assembly 52, a reaction vessel supply system 54, an incubator and separation carousel 56, a reagent storage assembly 58, a reagent robot 60, a wash robot 62, a solid waste system 64, a sample handler 66, and a fluidics system 68. Each of these components are shown in FIG. 3 and described in more detail in section 5.3 below.

5.2 Detector Module 5.2.1 Overview of Detector Module ("DM")

According to a preferred embodiment, detector module 20 is a dual-laser flow cytometer system including fluidic, electronic and optical subassemblies. The main optical components of the detector module are: red laser for bead classification, green laser for label excitation, a PMT (photomultiplier tube) for detecting label emissions and photodiodes to detect signal coming as a result of excitation of the classification dyes in microparticles.

More particularly, in one embodiment detector module 20 is an advanced immunoassay analyzer incorporating SUSPENSION ARRAY (LUMINEX CORPORATION). Briefly, SUSPENSION ARRAY analysis involves the process of analyzing populations of microspheres (or "beads") having unique intensities of red and near infrared dyes, allowing each bead population to be identified and analyzed separately. Bead populations are distinguished with unique binding molecules making each population sensitive to a particular analyte. A fluorescent indicator dye is then used to quantify the amount of bound analyte on each bead. Calibrators convert average population intensity into analyte concentration. Performing the chemistry on microspheres, e.g., on the surface of microspheres, leads to significant reduction in reagents, yielding significantly lower costs for consumables. Additional details may be found in U.S. Pat. Nos. 6,592,822; 6,528,165; 6,524,793; 6,514,295; 6,449,562; 6,411,904; 6,366,354; 6,268,222; 6,139,800; 6,057,107; 6,046,807; 5,981,180; 5,802,327; and 5,736,330; as well as in published U.S. Application Numbers 20030132538, and 20020182609, each of which in incorporated by reference herein in its entirety.

Detector module 20, in one embodiment, includes a flow cytometer having one or more lasers, optics, photodiodes, a photomultiplier tube, and digital signal processing to perform simultaneous, discrete measurements of fluorescent microspheres. In one embodiment, three avalanche photodiodes and a high sensitivity photomultiplier tube (PMT) receive photon signals from the microspheres. Detector module 20 in this example digitizes the waveforms and delivers the signals to a digital signal processor (DSP). The detector module works with the SPM and host computer to perform multiplexed analysis simultaneously by using the flow cytometer and digital signal processor to perform real-time analysis of multiple microsphere-based assays. Because a flow cytometer has the ability to discriminate different particles on the basis of size and/or fluorescence emission color, multiplexed analysis with different microsphere populations is possible. Differential dyeing microspheres, emitting light at two different wavelengths, allows aggregates to be distinguished and permits discrimination of, in one embodiment, up to about 25 different sets of microspheres, in another embodiment up to about 100 different sets of microspheres, and in yet another embodiment more than 100 different sets of microspheres. Several control beads are used in every analysis to ensure quality control of the results. The system can analyze small-molecular weight (e.g., T4) and large molecular weight analytes including, for example, IgG, IgA, and IgM antibodies, and glycoprotein hormones.

In one embodiment, fluorescence excitation a preferred embodiment of a MAD system involves two solid state lasers. These lasers illuminate the microspheres as they flow single file through the cuvette. The fluorescent signals are discriminated with selective emission filters and are converted into intensity units by using the DSP. There are two different fluorophores present within the microbeads which emit with two different emission profiles that are separately measured in order to define the address (test analysis) of the bead.

Immunochemical reactants, such as antigens, antibodies receptors, peptides, oligonucleotides, DNA, RNA, small molecules, viruses, viroids, cells, and the like of these assays become bound to the surfaces of uniquely addressed fluorescent microscopic beads. The fluorescent spectral address of each bead identifies each of the assays performed simultaneously on a single sample. Based on its fluorescent signature, every microsphere is classified to its own unique region. In addition, each bead is scanned for the presence of a reporter fluorescence that quantifies the bead-assigned assay at the bead surface. The MAD microspheres are highly uniform, polystyrene-based particles that have been crosslinked during polymerization to provide physical strength and stability. They also contain a magnetic core so that they can be attracted to an electromagnet to facilitate facile washing. The beads may be magnetic, paramagnetic, superparamagnetic or the like to facilitate processing and washing of samples. Varying ratios of different fluorochromes embedded within each microsphere give each bead a unique spectral address. Each microsphere is dyed to emit light in a certain classification channel. All microspheres of given emissions represent a distinct assay within a multiplex of assays. A reporter channel is used to detect fluorescence bound to the surface of each microsphere, and each reporter emission quantitates each of the distinct assays. Only one reporter is needed for a multiplex of assays. To ensure the stability of this address, the microspheres should be protected from light and high temperatures.

One technology employed in the MAD system is flow cytometry. Flow cytometry is a technique that simultaneously measures and then analyzes multiple physical characteristics of single particles, usually cells, as they flow in a fluid stream through a beam of light, most commonly from a laser. As a technique, flow cytometry is somewhat analogous to fluorescent microscopy; one major difference is that flow cytometry provides a digital result. In flow cytometry, measurements are performed on particles (e.g., cells or microbeads) in liquid suspension, which flow one at a time through a focused light (e.g., laser) beam at rates up to several thousand particles per sec.

The properties measured by flow cytometry may include a particle's relative size, relative granularity, internal complexity, and relative fluorescence intensity. These characteristics are determined using an optical-to-electronic coupling system that records how the cells or beads scatter incident light and emit fluorescence.

Figure 4:
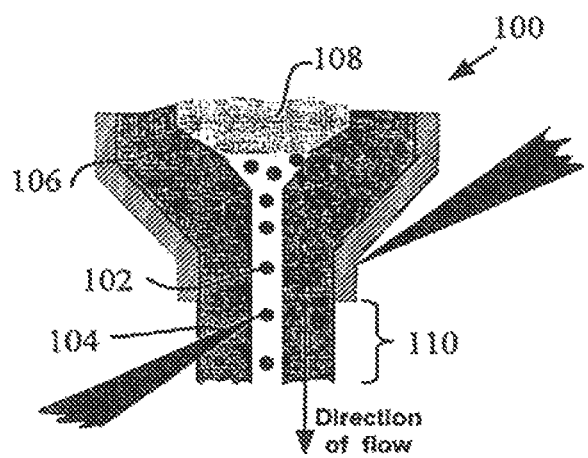
FIG. 4 shows typical flow cytometer fluidics as incorporated in an embodiment of the present invention.

The detector module flow cytometer includes three main systems—detector fluidics, optics, and electronics. The detector fluidics system transports particles in a stream to a laser beam for interrogation. A diagram of a typical flow cytometer fluidics system is shown in FIG. 4. Details of the MAD flow cuvette design and the wavelengths of the two laser beams used in MAD system are provided in FIG. 5. The optics system consists of lasers to illuminate the particles in the sample stream and optical filters to direct the resulting light signals to the appropriate detectors. Details of the MAD detector optics design are provided in FIG. 6. The electronics system converts the detected light signals into electronic signals that can be processed by the computer 40.

As shown in FIG. 4, in the MAD flow cytometer 100, particles 102 are carried to the laser intercept 104 in a fluid stream; this liquid is referred to as sheath fluid 106. Particles 102 are carried by a microscopic jet of buffer and are hydrodynamically focused in the center of the fast moving stream 106 of the sheath fluid. The particles 102 pass one by one (some particles in the flow stream may not be individual entities; particles may be bound to each other or in such close proximity that they are detected as a single bead) through an intense beam of excitation light in the measuring region of the flow cytometer. Each particle thereby produces short flashes of fluorescence, the intensities of which are proportional to the content of the fluorescently labeled constituent. FIG. 4 shows a flow cytometry fluidics system according to an embodiment of the present invention showing the flow direction, injector tip 108, flow cell 110, laser beam 104, and sheath fluid 106.

The fluorochromes emit fluorescent light many times during the transit time of a bead through the flow cuvette.

Suspended particles or cells preferably from about 0.2 to about 150 micrometers in size are suitable for flow cytometric analysis. The portion of the fluid stream where particles are located is called the sample core. When particles pass through the laser intercept, they scatter laser light without loss or gain of energy. Any light excited molecules present on the particle fluoresce. The scattered and fluorescent light are collected by appropriately positioned lenses. A combination of beam splitters and filters directs the scattered and fluorescent light to the appropriate detectors. The detectors produce electronic signals proportional to the optical signals striking them.

List mode data (photon recordings are recorded in a list) are collected for each particle or event. The characteristics or parameters of each event are based on light scattering and fluorescent properties. The data are collected and stored in a computer. These data can later be analyzed to provide information about subpopulations within the sample.

Figure 5:
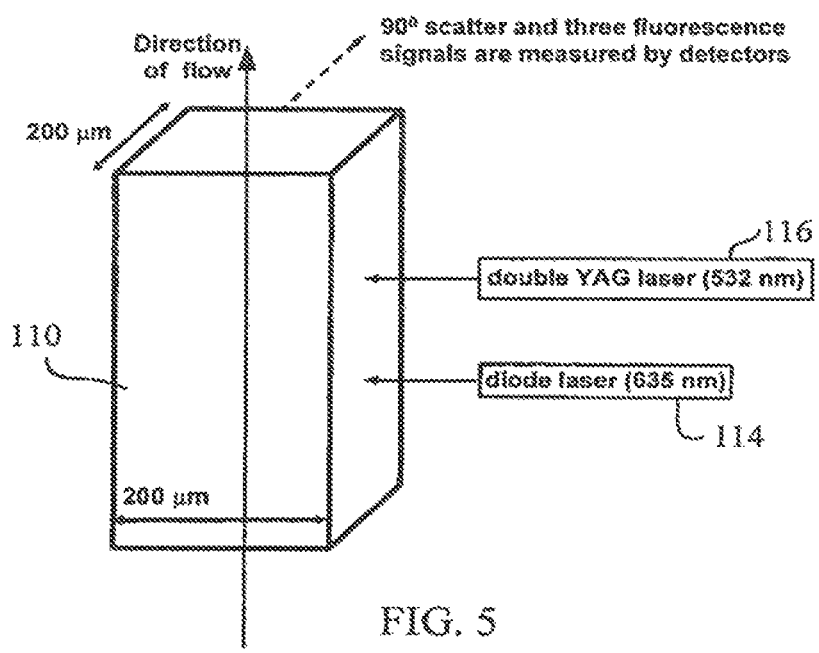
FIG. 5 shows a flow cuvette design and wavelengths of two laser beams according to an embodiment of the present invention.

FIG. 5 details a MAD flow cytometry cuvette flow cell 110 according to an embodiment of the present invention showing the cell dimensions and the laser beam wavelengths 114, 116. The dimensions shown, e.g., approximately 200 μm×200 μm, are approximate inner dimensions of a suitable flow cuvette. According to one embodiment, the outer dimensions are preferably about 2.2 mm by 2.2 mm. One skilled in the art will appreciate that cuvettes of other dimensions or characteristics are known and may be used without departing from the scope of the invention.

Figure 6:
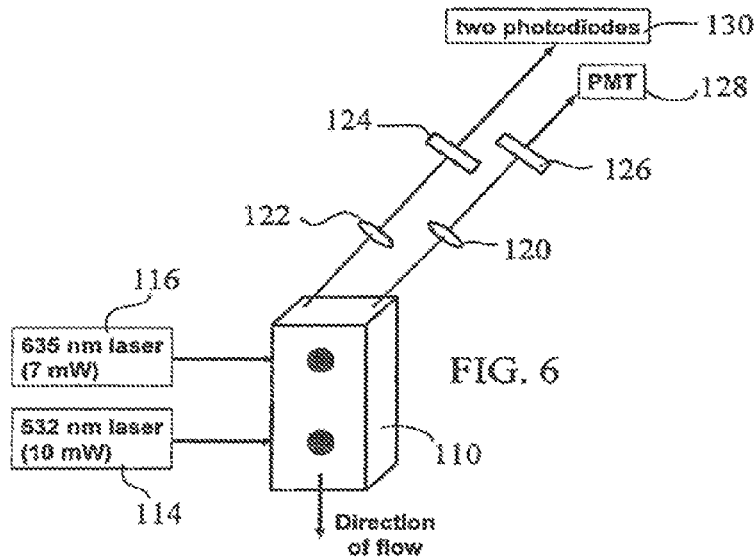
FIG. 6 shows an optics design according to an embodiment of the present invention.

FIG. 6 details a MAD optics design according to an embodiment of the present invention showing flow cell 110, reflectors 124,126, lasers 116,114, lenses 120, 122, and detectors 128,130.

In a preferred embodiment, detector module 20 is equipped with two lasers 114 and 116. Particular characteristics of lasers 114 and 116 are described below, however one skilled in the art will appreciate that numerous other laser systems and analyzers are known in the art and may be used depending upon the types of assays one desires to perform; any such lasers or alternative analyzers or detector modules may be employed in detector module as part of the overall MAD system without departing from the scope of the present invention.

In this example, diode laser 116 produces about 7 mWatts of about 635 nm (red) light. This laser is also referred to herein as red laser 116 or the classifier laser 116 since it is used to excite the classifier dyes within a bead leading to the identification of the bead region to which the bead belongs.

The second laser, laser 114, is preferably a diode-pumped, solid state, continuous wave (CW), doubled Nd:YAG laser. In this example embodiment, laser 114 produces about 15 mWatts of power and about 532 nm (green) light. Laser 114 is also referred to herein as green laser 114 or reporter laser 114 since it functions to excite the reporter (label) groups at the microsphere or bead surface. Green laser 114 preferably has a power stability of less than +/−2% over 8 hours, and a beam diameter of 0.32 mm+/−10%. Laser 114 uses yttrium aluminum garnet (YAG) as the matrix material, doped with neodymium (Nd:YAG). A 15 mm lens is used as the primary focusing lens for the 532 nm laser 114.

Further, in this embodiment, there are two 4 mm lens assemblies 120, 122 located approximately 900 mm from the laser beam path. They are precision aligned to the cuvette and collect the fluorescent signals, both reporter and classifier. A 550 nm-610 nm reflector is used to deflect the reporter signal to the single photomultiplier in the MAD system. A 630 nm-760 nm reflector is used to deflect the classifier signal to two classification channel avalanche photodiodes. One photodiode detects the "red' classifier dye emission and the other the "orange" classifier dye emission. Orthogonal scattered light (from the beads) is also measured on the system using a third avalanche photodiode. A block, referred to as the "U" block, houses the classifier and doublet discriminator lenses, the diodes, and circuitry. In one embodiment, the flow cuvette is made of quartz and has a width and depth of 200 μm. The light gathered by the photodetectors initially exits through one of the cuvette's walls, is reflected by a mirror, and finally passes through a filter before reaching the detector. The numerical aperture of the detector is 0.62. The mirror causes about 2% loss in light intensity and the filter cuts the intensity by about 50%. Fluorescence emission from the bead surface takes place at all angles and only a few percent of the total emitted photons are collected by the first mirror due to the physical limitations of the optics design. Therefore, only a very small percentage (e.g., probably <1%) of emitted photons are actually recorded by the detector.

Alternatively, other more powerful 532 nm lasers 114 may be used to improve the analytical sensitivity of immunoassays. In particular, an approximately 50 mWatt laser photobleaches the primary detector molecule, B-phycoerythrin, used as a reporter for most assays. The optimal wattage for 532 laser 114 is about 10-20 mWatt in this example, however other wattages or lasers may be used.

There are two fluidic paths in this MAD system detector module. The first path involves a syringe driven mechanism that controls the small volume sample uptake. This syringe driven system transports a user specified volume of sample from a sample container to the reaction vessel (RV). After reaction incubation(s), the sample is injected into the flow cuvette at a steady rate for analysis. Following analysis, the sample path is automatically purged with sheath buffer by the second fluidics path. This process effectively removes residual sample within the tubing, valves, and probe. The second fluidics path is driven under positive air pressure and supplies the sheath fluid to the cuvette.

As will be described in more detail below, in this embodiment, following the last aspiration of wash, MAD system 10 dispenses wash buffer, e.g., approximately 20-70 µA, more preferably about 50 µl, into the reaction vessel (RV) in preparation for fluorescence reading. Approximately all of this volume is aspirated to the detector. The first approximately 5 µl is ignored by the detector before reading commences. The length of time to read the beads is generally dependent on the bead concentration since in this example there is a defined number of beads read for all regions, e.g., in this example about 200 beads read for all bead regions. This typically requires from about 5 to 25 sec. Counting of beads on the MAD system 10 terminates when either the defined number of each regional bead in the assay panel are counted, or when the allocated time for fluorescence analysis is completed. Since not all beads are at exactly the same concentration, most bead sets will acquire more than 200 counts. Analysis terminates with the last bead region to reach the defined number, e.g., 200, counts. The allocated time is determined by the sample flow rate and by its volume. The assay cycle time for the preferred timing sequence used by the IgG and IgM serology panels, and the systemic autoimmune panel, is, e.g., 30-40 sec, more preferably about 36 sec. The percent of the cycle time that the MAD system is reading fluorescent beads with the preferred timing sequence is therefore in this particular example about 28% to 53%. Of course, other time cycles may apply depending upon system set-up and types of assays performed.

The transit time for an individual bead to travel from the flow cuvette 110 location in which it is interrogated by red laser 116 to the location where the bead is illuminated by green laser 114 is about 35 µsec. The instrument's firmware measures the exact transit time during the detection calibration step. In an actual assay, the detector measures this time from bead's coincident CL1 and CL2 readings (see FIG. 7), and then measures the conjugate derived fluorescence (RP-1) (see FIG. 7). Since the flow rate is approximately constant, MAD system 10 "knows" that a given green fluorescent signal is associated with the red and orange emissions registered 35 µsec earlier. Because the bead concentration in the flow stream is low, there is only a very low statistical chance that the RP-1 signal would be misassigned to the wrong bead, i.e., a close proximity second bead in the flow cell. Since the flow rate for the MAD system is nominally 2.3 msec, a bead would flow 81 microns in 35 µsec. The distance between the focal points for the two lasers 114, 116 is therefore about 81 microns.

Because the fluorescence readings of the red 116 and green 116 emissions must be temporally coordinated, it is desirable that the flow rate remain constant within a narrow range. Some change in flow rate does occur and the MAD system can accommodate minor fluctuations. Larger changes in the flow rate of beads through the detector would cause significant problems. When detector module 20 of instrument 10 is calibrated, not only are the voltage settings adjusted to attain the three pre-designated RFI readings, but the instrument also adjusts for the time required for bead transit from the red 116 to the green 114 laser illuminations. As the flow rate changes due to pressure changes in the system, the transit time changes in a near linear relationship. Once MAD system 10 is calibrated and the transit time established, subsequent change in pressure (and thus flow rate) will affect the results, leading to deleterious effects including lower RFI values and decreased precision.

In one embodiment, detector module 20 takes somewhat less time to read the beads than the LUMINEX LX100, all else being equal. This is because the MAD system's analyzer preferably employs efficient magnets for wash and separation of analytes. Fewer beads are therefore lost with the MAD system 10, the concentration of beads in the flow cell is higher, and the time to count 200 beads per region is less.

Fluorescent measurements of beads on detector module 20 are gated, where a gate is a boundary that defines a subset or sub-population of events. Gates are set by electronically drawing boundaries around the data subsets. Gates can be used either for data acquisition or analysis. Inclusive gates select only the events that fall within (and on) the boundary. Exclusive gates select only the events that fall outside of the boundary. (The gates described in this paragraph are data acquisition and exclusive gates). One gate is fixed by the firmware and two gates are optionally set by the operator. The first gate is automatically established and determines whether the CL1 and CL2 signals for an individual bead fit within one of the established bead map regions. If it does, the bead passes that gate. If not, the data for the bead is filtered out and subsequently ignored. The second gate, which is operator established through the user interface, is the doublet discriminator gate. This gate is based on the light scatter measurement of the bead. The purpose of this gate is to exclude bead aggregate events (larger than an individual bead) or bead debris events (smaller than an individual bead). The third filter is the RP-1 gate. This gate excludes two types of events—zero RFI beads and very bright beads (high statistical outliers) from further data analysis. The last gate is also user defined.

Fluorescent spillover occurs when two or more emission spectra overlap so that selective filtering cannot occur. In some flow analyzers, emission spillover is corrected using a technique called compensation. Compensation involves subtraction of some emission percentage from another emission signal. One embodiment of system 10 does not use compensation; however, the reporter signal does not significantly spill over into the classification emission.

The reporter fluorochrome is bound to the surface of the microsphere and provides raw analytical data. Because a microsphere suspension provides near liquid phase reaction kinetics, each microsphere of a particular spectral address theoretically binds an equal number of reporter molecules. Equal binding results in a statistically even distribution of reporter on each microsphere in a set. This means numerous replicates for each microsphere population are measured from a single well. The confidence in a given measurement strengthens with increased replicate measurements. For adequate confidence, 200 events per microsphere set in each well is usually sufficient.

5.2.1 Characteristics and Uses of Microspheres

In a preferred embodiment of system 10, instead of employing commonly used microtiter wells to host the immunochemistry-based assays, the immunoassay reactions occur on the surface of microscopic, magnetic, polystyrene-core beads known as microspheres. Suitable microspheres are disclosed, for example in the LUMINEX patents listed above. Although such microspheres are not necessarily part of detector module 20, they are described herein as they are integral to the principals of operation of an exemplary embodiment of the detector module 10 as described.

Prior to use, microspheres are maintained in suspension in a bead reagent solution. Individually dyed with combinations of two different fluorescent dyes (red and orange), a microsphere may have one of many possible levels of classifier dye fluorescent intensities. The various combinations of dyes create a sets of, in one embodiment, up to 25 uniquely color-coded microsphere sets, in another embodiment up to 100 uniquely color-coded microsphere sets, and in yet another embodiment more than 100 uniquely color-coded microsphere sets. In one embodiment, antigens or antibodies indicative of a specific bacterial or viral antigen, protein, or other molecule are coated onto the surfaces of each uniquely color-coded bead set, making each different microsphere set representative of a different assay.

Because in this example each microsphere is coated with antigens or antibodies specific for a given condition, each microsphere is equivalent to an individual microtiter well used in many enzyme-linked immunosorbent immunoassays (ELISAs). Alternatively, beads may be coated with proteins, antibodies, ligands or the like in order to run a wide variety of assays and assay formats. MAD system 10 can simultaneously run (multiplex), according to one embodiment, up to 25 assays in a single reaction vessel, in another embodiment up to 100 assays in a single reaction vessel, and in yet another embodiment, more than 100 assays in a single reaction vessel, using as little as 5 µl of sample. Beads may include fluorescent or other labels, or may be secondarily labeled during processing with labeled antibodies that bind to a target molecule after it is bound to a bead.

Figure 7:
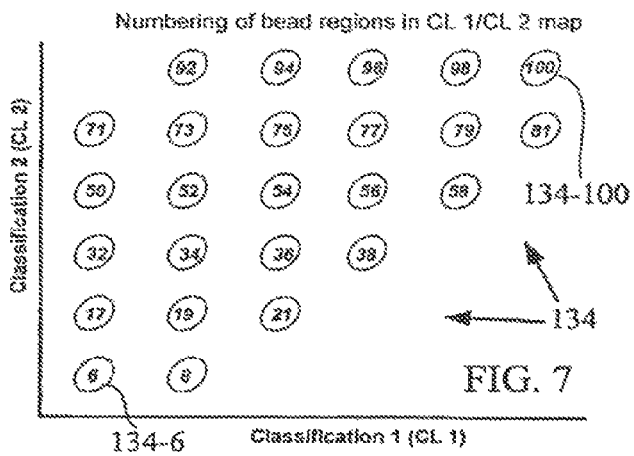
FIG. 7 shows a bead "map" showing relative fluorescence signals from two classifier dyes for a set of 25 beads according to an embodiment of the present invention.

FIG. 7 shows microspheres serving as the vehicle for molecular reactions. The microspheres are approximately 8.0 µm polystyrene microspheres that bear carboxylate functional groups on the surface. The microspheres are available in 25 distinct sets 134 that are classified by the flow cytometer by virtue of the unique orange/red emission profile of each set, as shown in FIG. 7. Microspheres of this size provide sufficient surface area for covalent coupling of $1-2\times10^6$ target molecules per microsphere. In use, fluorescence classification of dual-labeled fluorescent microspheres is used. Two-dimensional dot plots report the classification of a 25 microsphere set based on simultaneous analysis of logarithmic orange fluorescence (FL2) and logarithmic red fluorescence (FL3). FIG. 7 also shows the positioning of each numbered bead set with regions 6 (labeled "134-6") and 100 (labeled "134-100") containing the least and most amount, respectively, of combined orange and red dyes.

Fluorescent reactants, e.g., fluorescent antibodies, antigens, or nucleic acid probes provide specific signals for each reaction in a multiplexed assay. Because each fluorescent reactant binds specifically to a target that is present on only one bead set in a multiplexed assay, the soluble reactants do not need to be differentially labeled. All fluorescent molecules are labeled with a fluorophore such as the organic green-emitting dyes BODIPY and fluorescein isothiocyanate, or a more commonly used biological fluorophore such as phycoerythrin. Any fluorochrome can be used as a reporter; however, each fluorochrome has a characteristic emission spectrum which affects the amount of spillover into the orange fluorescence channel. In one example green-emitting fluorophores are used.

To prepare a multiplexed assay, individual sets of microspheres are conjugated with the target molecules required for each reaction. Target molecules may be antigens, antibodies, oligonucleotides, receptors, peptides, etc. Fluorescent reactants may be complementary oligonucleotides, antigens, antibodies, receptors, etc., i.e., any molecule that will specifically bind to the target molecule. After optimizing the parameters of each assay separately in a nonmultiplexed format, the assays can be multiplexed by simply mixing the different sets of microspheres. The fluorescent reactants also are mixed to form a cocktail for the multiplexed reactions. The microspheres are then reacted with a mixture of analytes, for example in a biological sample, followed by the cocktail of fluorescent reactants. After a short incubation period, the mixture of microspheres, now containing various amounts of fluorescence on their surfaces, are analyzed with the flow cytometer. Data acquisition, analysis, and reporting are performed in real time on all microsphere sets included in the multiplex. As each microsphere is analyzed by the flow cytometer, the microsphere is classified into its distinct set on the basis of orange and red fluorescence, and the green fluorescence value is recorded. Two hundred individual microspheres of each set are analyzed and the median value of the green fluorescence is reported.

With respect to protein antigens, methods for coupling proteins to bead surfaces are well known. For example, covalent coupling of protein antigens to bead surface carboxyl groups by amide bond formation requires protonated carboxylic acids for the initial activation and esterification steps of the conjugation reactions. Since the pKa of carboxylic acids is higher in ethanol than in water, conducting the initial steps in buffered ethanol is advantageous compared to conducting them in aqueous buffer. For example, ethanol raises the pKa of methacrylic acid from pH 4.9 to approximately pH 6.0, which means that approximately ten-fold more carboxyl groups will be available for coupling when the beads are activated and esterified at pH 5.0 in buffered ethanol compared to pH 5.0 in aqueous buffer. However, because the classification dyes used to define the spectral addresses of the beads are soluble in organic solvents and are only infused into the bead surface, it seemed possible that exposure of the beads to ethanol would result in leeching of these dyes. Depending on the extent of extraction, leeching of classification dyes could reduce classification efficiency, and if extreme, could even cause misclassification. Other potential effects of ethanol include increasing bead autofluorescence and decreasing bead dispersion in aqueous solution. The objective of a conducted experiment described below was therefore to determine whether exposure of dyed beads to ethanol compromised classification efficiency, increased autofluorescence, and/or decreased dispersion in aqueous solution. To address these issues, dyed beads were exposed to absolute ethanol for four hours and sampled at 30 minute intervals. At the end of the exposure period, the beads were evaluated sequentially in an LX-100 flow fluorometer and classification, autofluorescence, and bead dispersion data were acquired. The data showed no change in classification efficiency and bead dispersion for the duration of the study, however, there was a nominal increase in autofluorescence for some regions after 120 minutes and a substantial increase for these regions after four hours. Overall, the data from these experiments indicated that activation and esterification of bead surface carboxyl groups for 60 minutes in 90% ethanol would not have adverse effects on the classification efficiency, autofluorescence, and dispersion of dyed beads. A consequence of this could be rearrangement of the bead surface ultrastructure through redistribution of hydrophilic and hydrophobic polymers, and a change in the ability of the beads to remain dispersed in aqueous solution. This concern could be dismissed however, because doublet discriminator data did not reveal any impact of ethanol on bead dispersion.

The data from this study indicated that exposure of dyed beads to ethanol for 60 minutes during carboxyl activation and esterification would not have any consequence on classification efficiency, autofluorescence, or dispersion of the beads in aqueous solution. Thus, exploiting the power of ethanol to raise the pKa of bead surface carboxylic acids offers a practical opportunity to increase the coupling efficiency of bead ligation procedures.

An embodiment of detector 20 uses a 14-bit analog to digital converter (ADC). The resolution in terms of histogram bin width is about 1/32,000. This is fairly limited resolution. A current version of the DSP in the LUMINEX obtains eight fluorescent readings from each bead during its lifetime in the focused region of the reporter laser. The RFI values reported by the DSP of the detector are essentially an integration of the eight fluorescent readings per bead. The height (direction of flow) of the laser-illuminated region in the detector flow cell is about 30 µm and the velocity of the sample stream is roughly 2.3 msec. Thus, the residence time of the bead in the illuminated region is about 13 µsec. Assuming a fluorescence lifetime of 5 nsec for the reporter label, the beads could be excited and then fluoresce 2,600 times (13 µsec/5 nsec) during the transit time (assuming no photobleaching). Therefore, reporter emission is recorded for less than 1% of the time the bead-bound label is in the laser light path.

In one embodiment, detector module 20 is a flow cytometer that uses a two-step calibration initiation. One calibrator (CAL-1) adjusts the correct gain for the bead classifier photodiode detectors (CL1 and CL2) and for the doublet discriminator detector (DD). The second calibrator (CAL-2) adjusts the gain for the reporter PMT (RP1). A current practice is to calibrate with CAL-1 to target values and calibrate CAL-2 to a fixed value, for example a value of approximately 17,000 irrespective of the target value. In one embodiment, the CAL-2 target value is around 3,800±10%.

In flow cytometry, electronic gating typically is used to isolate classes of cells or particles. Often, gating is used to differentiate one population of cells or particles from other populations. Doublet discriminator (DD) gating is also used to eliminate debris and aggregates from the counting statistics. The within-RV CV % values are lower when DD gates are used. In the case of the detector, differentiation is accomplished via region gating (CL1 and CL2) and there is a partial gate on the reporter channels that allows elimination of very low RFI events (usually between 0-2). DD gating is almost exclusively used by flow cytometers to eliminate debris and aggregates.

In addition to recording three different fluorescence measurements, MAD system 10 also detects light scatter. The collected scattered light is orthogonal scatter, also referred to as right-angle, side-angle, or wide-angle scatter. Orthogonally scattered light is a good reflection of the size of the particle from which the light impinged and was scattered. Side-angle scatter is easily capable of distinguishing a bead from a bead doublet (two beads stuck to each other or in very close vicinity). Detection of bead doublets is called doublet discrimination. In flow cytometry it is the usual practice to eliminate recorded doublet events from the data analysis since their physicochemical behavior is often aberrant when compared to single beads. Elimination of doublets can improve the precision and accuracy of an assay. When light impinges on a particle it is scattered without loss of energy in many directions. The magnitude and angles of scatter depend on such parameters as particle size, density, and shape.

Right-angle light scatter is detected on the MAD instrument with an avalanche photodiode, the same type of detector used to classify the beads into regions.

Figure 8:
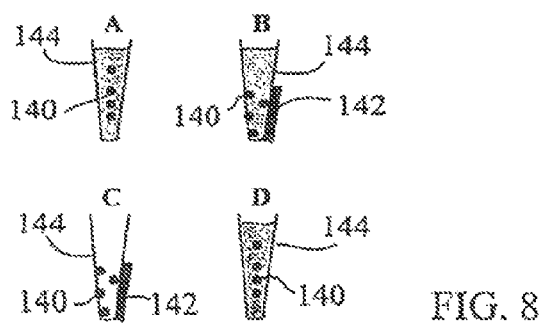
FIG. 8 shows washing of magnetic beads using electromagnets according to an embodiment of the present invention.

FIG. 8 schematically represents a process of washing microspheres 140, or beads, using magnets 142. Microspheres can be magnetic or have metallic properties or other properties that allow them to be attracted to magnets 142 during washing. When washing is required, reaction vessels 144 containing beads 140 in a solution 146 (e.g. a buffer solution or an assay reagent) are placed near two strong electromagnets 142 (e.g., in separation carousel 55 of FIG. 3). Magnets 142 attract and hold beads 140 to the sides of the reaction vessel 144. Liquid 146 is then aspirated from the reaction vessel leaving the beads on the vessel 144 sides attracted to magnets 142. After removal of the magnets 142 as shown in FIG. 8C, and beads are resuspended in another volume of liquid 146 as shown in FIG. 8D.

5.3 Sample Processing Module ("SPM")

5.3.1 General Features of SPM

Referring again to FIG. 3, one embodiment of sample processing module 30 can include a number of subsystems and components for automating sample handling and assay procedures of system 10. Such subsystems can include a specimen rack handler assembly 50, a reaction vessel handler assembly 52, a reaction vessel supply system 54, an incubator and separation carousel 56, a reagent storage assembly 58, a reagent robot 60, a wash robot 62, a solid waste system 64, a sample handler 66, and a fluidics system 68.

Each of the various subsystems and their interactions are described in more detail in sections below. Each of these subsystems and their physical relationship to other subsystems and components within SPM 30 are described in the context of an exemplary embodiment of system 10, and such examples are not intended to limit the invention. One skilled in the art will appreciate that variations in each subsystem and/or their interactions may be made without departing from the scope of the invention.

For example, in the embodiment of system 10 detailed below, SPM 30 includes twenty seven discrete stepper motors for actuation of various instrument robotic systems. These include multiple high speed high power carousel drives capable of better than, e.g., 0.5 sec positioning times, for moving incubation and separation carousel 56 and reagent carousel 70. In addition, multiple X, Y robots having, e.g., at least 0.5 mm placement accuracy, preferably about 0.2 mm or better placement accuracy, are employed for driving specimen rack handler 50, reaction vessel handlers 52, reagent robot 60, sample handler 66, wash robot 62, and detector transfer robot 74. Additionally, Z-theta robots may be used to minimize probe movement times even further for time critical actions. One skilled in the art will appreciate that different number and types of subsystems and drive motors may be employed without departing from the overall spirit of the present invention.

Motor drives and sensor feedback are provided by a number (e.g., four or more) of custom designed stepper and sensor control printed wire assemblies (PWA's; also termed herein printed circuit boards, or PCB's), each capable of simultaneously driving multiple motors. Each has the capacity for multiple, e.g., up to 24, sensor inputs used for positional feedback and motor step loss detection.

As will be described in more detail below with respect to some subsystems, e.g., specimen rack handler 50, RV handlers 52, reagent robot 60 and incubator carousel assembly 56, integrated circuit boards related to each subsystem of SPM 30 preferably communicate over an integrated compact PCI bus main system processor board of host computer 40. The main system processor board of host 40 can be, e.g., a Pentium III or the like single board computer running at 850 MHz, with 128 Mbytes on board RAM and 48 Mbytes flash disk permanent storage. Alternatively host 40 can also be a remote server which the device communicates with over a network. The logging of operational data to a controlling host via USB minimizes the requirement for data storage on system 10.

SPM 30 as described in the example below also incorporates four or more pipetting probes for manipulating samples and reagents, e.g., a sample handing probe associated with sample hander assembly 66, a reagent probe associated with reagent robot assembly 60, a wash dispense probe associated with wash robot 62, and a detector probe associated with detector robot 74. Sample handler 66 probe is used to aspirate and dispense samples from within tubes 167 on specimen rack handling assembly 50 into reaction vessels on incubation and carousel assembly 56. Reagent robot 60 probe is used to aspirate and dispense reagents from reagent packages 80 in reagent carousel 70 into reaction vessels on incubation and separation carousel. In one embodiment, reagent robot 60 and sample handler 66 probes share a common tapered-tip design and are interchangeable. Wash robot 62 probe and is used to dispense wash solution into reaction vessels on incubation and separation carousel 56. Detector robot 74 probe is used to aspirate the completed assay bead solution into detector 20 for analysis.

Each of the probes described herein are preferably made of stainless steel with an internal polished surface to reduce nonspecific binding. In one embodiment, internal diameter of sample handler 66 and reagent 60 probes at the tapered tip is 475±25 µm (e.g., approximately 60-fold wider than the diameter of the magnetic beads). All probes except the detector probe are preferably tapered and beveled. Sample handler 66 and reagent robot 60 probes preferably incorporate sensors such as capacitive liquid level sensors for accurate and repeatable sensing of the liquid surface height, as well as pressure sensing for detection of blockage and/or when a probe is in contact with the bottom of an empty vessel.

Additional details of each of the subsystems and major components of sample processing module 30 follow.

5.3.2 Specimen Rack Handler Assembly

Figure 9:
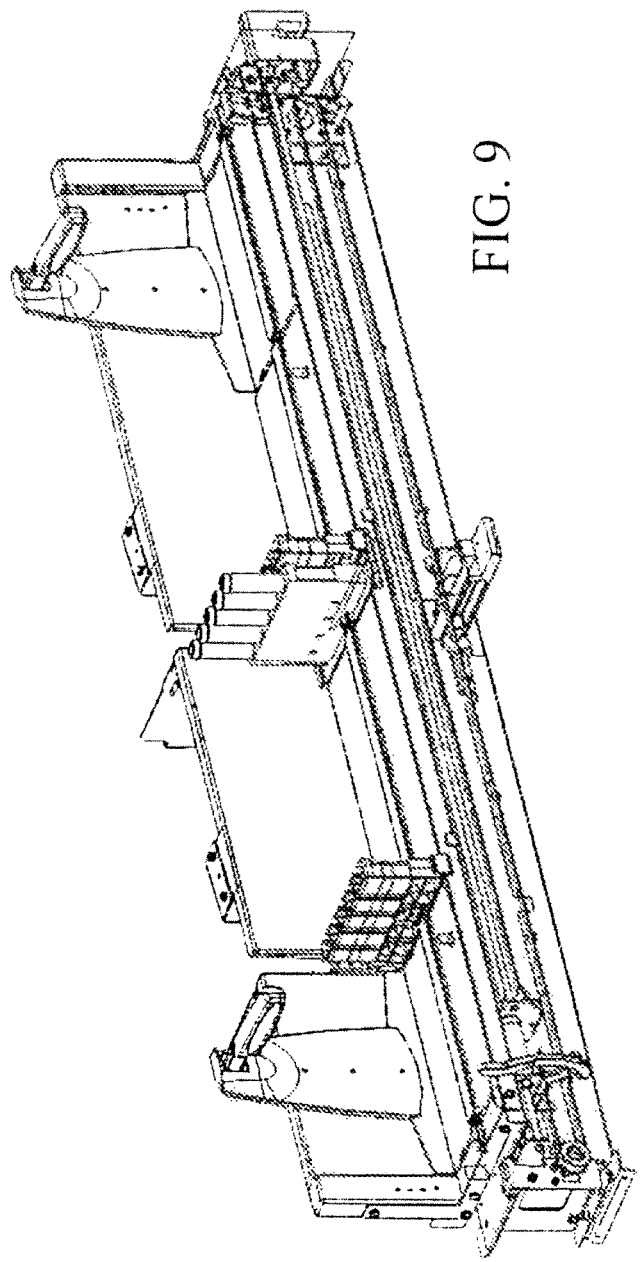
FIG. 9 is a perspective view of a sample rack handler assembly according to an embodiment of the present invention.
Figure 10:
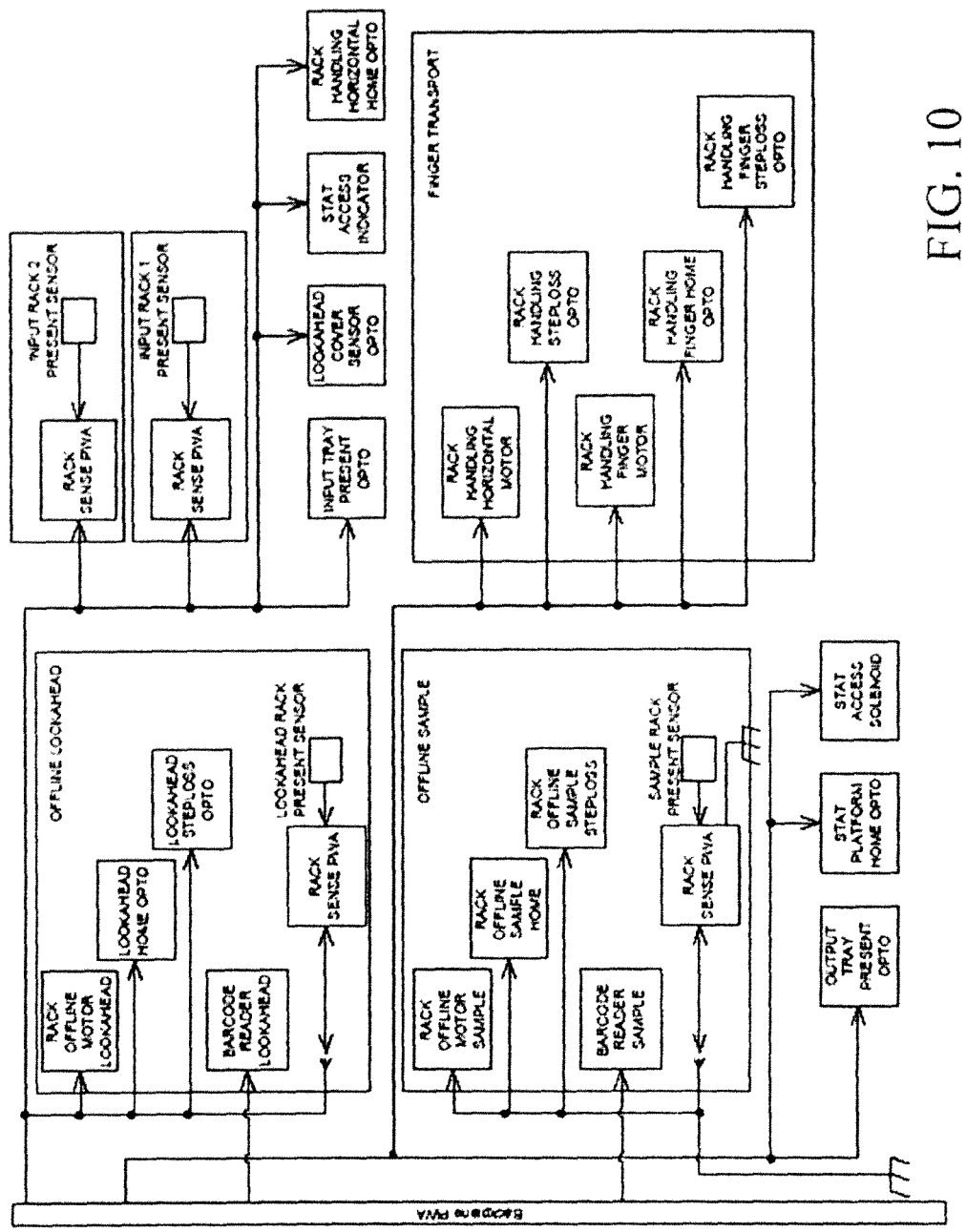
FIG. 10 is a block diagram of the specimen rack handler assembly of FIG. 9.

FIGS. 9 and 10 depict a specimen rack handler assembly 50 (also referred to herein as "specimen handler" or "rack handler") according to an embodiment of the present invention. Specimen handler 50 moves samples from an input area 150 through an instrument work area 160 to an output area 164. In doing so, the specimen handler moves the samples into an aspiration position. The specimen handler identifies each rack 166 and sample tube 167 by reading a barcode contained on each. There is a STAT (Short Turn Around Time) drawer 156 that provides the user with a mechanism for inserting a rack 166 to be sampled and tested out of sequence. The specimen rack handler assembly 50 also allows for continued uninterrupted operation while a user adds or removes samples.

Specimen handler assembly 50 generally includes an input area 150, 151, a main work area or horizontal platform 160, a robotic finger 152, a look-ahead offline platform 154, a STAT drawer 156, an aspiration offline platform 158, a look-ahead barcode reader 162, an aspiration offline barcode reader 164, and sample trays and racks 166.

Robotic Finger 152 is designed to move sample racks 166 along horizontal platform 160 without interfering with any of the other specimen handler 50 components. In one embodiment, finger 152 employs a 2-axis mechanism (horizontal in the x-axis and rotational). The two-axes work in conjunction to allow the finger to either push a rack (e.g., to the right or left) or bypass a rack. The horizontal axis provides the horizontal motion while rotational axis provides the option for either engaging or disengaging from pushing the racks.

Referring to FIG. 10, horizontal movement of finger 152 is belt-driven by a stepper motor 222. This motor/belt drive assembly 222 is preferably located underneath the horizontal platform 160 to minimize its interference with other specimen handler 50 components and accessibility to users.

The rotational axis movement is also belt-driven by a stepper motor 226. Motor 226 preferably rotates a square shaft (on which the horizontal motion occurs) of finger 152 to move finger 152 down to a disengaged position (as shown) or up into an engaged position. In the engaged position, finger 152 can slide racks 166 from right to left along horizontal platform as shown in FIG. 9 under the power of horizontal stepper motor 222.

The number of sensors monitor the position and status of the robotic finger 52. A finger horizontal home optical sensor 223 located on farthest right side of the specimen handler 50 determines the horizontal home position of finger 52. A Finger horizontal step optical sensor 224 located on the farthest right side of the specimen handler 50 determines the horizontal position of finger 152. A finger rotational home optical sensor 228 located on farthest right side of specimen handler 50 determines the rotational home position of the finger 152. A finger rotational step optical sensor 230 located on the farthest right side of the specimen handler 50 determines the rotational position of the finger 152. Each of the motors 222, 226 and sensors 223, 224, 228, 230 is electrically connected to system 10 via backplane printed wire assembly 200.

The look-ahead offline platform 154 is designed to move the racks (and associated specimen tubes) off the horizontal platform 160 and identify them for the host control 40 software. Look-ahead barcode reader 162 is used to read and identify barcodes of both samples 167 and rack 166 when the look-ahead offline platform pulls a rack 166 off horizontal platform 160.

Scheduling software in host computer 40 optimizes the throughput of the instrument and uses the information provided by barcodes on each of the racks 166 and sample tubes 167.

Movement of the offline look-ahead platform 154 is driven by an offline look-ahead motor 202. Motor 202 moves platform 154 (and a rack 166 located thereon) in a y-axis direction (e.g., in a direction perpendicular to the long axis of horizontal platform 160) to present racks 166 and sample tubes 167 to bar code reader 162. A number of optical sensors are present on the look-ahead offline platform 154. For example, a look-ahead offline rack optical sensor 210 determines the presence of a rack 166 on the platform. This sensor 210 is located on the top rear of the look-ahead offline platform 154204. A look-ahead offline platform home optical sensor determines the horizontal (y-axis) home position for the look-ahead offline platform. Sensor 204 is located behind the horizontal platform 160 near barcode reader 162. A look-ahead offline platform step optical sensor 206 determines the horizontal (y-axis) position for the look-ahead offline platform. This sensor 206 is located behind the horizontal platform 160 on the rotational drive gear. Rack sensor 210 communicates with circuit board 208 and each sensor 202, 204, 206, 210 electrically communicates with system 10 through backplane 200.

The STAT drawer 156 is designed to provide the user the ability to place a rack 166 (with samples 167) at the head of the queue for immediate processing by instrument 10. Rack 166 is placed just prior to aspiration offline platform 158 so it will be moved onto platform 158 as soon as the current rack is finished. No other action is required by the user, aspiration offline platform 158 will automatically transfer the rack and sample information to the scheduling software in host 40.

A sensor 234, e.g., such as a mechanical plunger type sensor, located on the underside of STAT drawer 156 determines the status of the STAT drawer 156.

The aspiration offline platform 158 is designed to move the racks (and associated specimen tubes) off the specimen handler 50 horizontal platform 160, identify them for the software and provide an aspiration location for the sample handler assembly 66 (which includes a robotically-controlled sample aspiration probe). As with barcode reader 162, aspiration barcode reader 164 associated with aspiration offline platform is used to identify both the rack 166 and individual tube 167 when aspiration offline platform 158 pulls them off of the horizontal platform 160. Typically, this is just confirming the information obtained by barcode reader 162 of the look-ahead offline platform 154, but occasionally, e.g., when STAT drawer 156 is used, barcode reader 162 will be providing new information to the scheduling software.

Similar to look-ahead platform 147, aspiration or sample offline platform 158 is driven by a motor 212. Motor 212 moves platform 158 (and a rack 166 located thereon) in a y-axis direction (e.g., in a direction perpendicular to the long axis of horizontal platform 160) to present racks 166 and sample tubes 167 to aspiration bar code reader 164.

The number of optical sensors are present on the aspiration offline platform 158. For example, an aspiration offline rack optical sensor 220 located on the top rear of aspiration offline platform 158 determines the presence of rack 166 on the platform. Aspiration offline home optical sensor 214, e.g., located behind horizontal platform 160 near the barcode reader 164, determines the horizontal (y-axis) home position for aspiration offline platform 158. An aspiration offline step optical sensor 216, e.g., located behind the horizontal platform on the rotational drive gear, determines the horizontal (y-axis) position for the aspiration offline platform 158.

Sensor 220 communicates with rack sense circuit board 218, and all of sensors 212, 214, 216, 164 and 218 communicate with backplane 200.

Horizontal platform 160 is designed to provide a stable horizontal surface for rack movement, input and output areas 151, 162 for sample trays, and manual rack input 150 and output 164 areas 150, 164.

Manual input area 150 provides the ability to add single racks 166 to the queue. Manual input area 150 is located at the far left of specimen handler assembly 50. When a rack 166 is placed here, sensor 220 is tripped notifying software in host 40. Finger 152 moves the rack 166 to the end of the queue. An optional manual input optical sensor 146, e.g., located behind the back wall of the specimen handler 50, includes a mirror mounted on the specimen handler 50 front. Placement of a rack 166 in manual input area 150 breaks the reflected beam of sensor 246.

Input tray area 151 provides a location for the placement of a sample tray 165. Once a sample tray 165 is placed, it essentially becomes part of horizontal platform 160 over which racks 166 are moved.

Input tray area sensor 252, e.g., located underneath specimen rack handler assembly 50, is preferably a magnetic reed type sensor. Sample trays 165 are equipped with magnets in the base to trip sensor 252 when the sample tray 165 is properly placed.

Look-ahead area 155 provides a storage area for racks 165 awaiting aspiration. Output holding area 157 provides an output area for racks (after sample aspiration). Typically, output holding area 157 will only have racks when the output tray 162 is missing or full.

Output tray area 162 provides a location for the placement of a sample tray 165. Output tray area sensor 232, e.g., located underneath specimen rack handler 50, is preferably a magnetic reed type sensor similar to sensor 252. As described above, sample trays 165 are equipped with magnets in the base that trip sensor 252 when such sample tray 165 is properly placed. An optional output tray capacity sensor, e.g., located behind the specimen handler 50, monitors how many racks 165 are on the output tray 162. After a specified number of racks, e.g., ten, have moved onto output tray area 162, such sensor trips software in host 40 to request the customer to remove and empty the output tray.

Manual output area 164 provides a location for the removal of single racks 166 from the output area 162.

In one embodiment, sample trays 165 are designed to carry ten racks 166. Sample trays 165 allow large numbers of racks 166 to be added to or removed from the instrument 10 with ease. When not in the instrument (being carried) a self-locking mechanism is used to ensure the racks 166 cannot inadvertently slide off from the tray 165. The self-locking mechanism automatically unlocks when the rack is placed on the instrument 10 or on a flat surface.

During typical operation of specimen handler assembly 50, sample tubes 167 are loaded into racks 166 that contain up to five bar-coded sample tubes in each rack. Optionally, racks 166 are loaded into a tray 165 that hold up to ten racks in a queue awaiting tube barcode reading and sample processing. Controls and calibrators are also loaded into the same racks and are appropriately barcoded for identification. After tray 165 is placed in the input tray area 151 on horizontal platform 16, input tray sensor 252 detects tray 165. Finger 152 retracts and moves all the way to the left of manual input area 150. Finger 152 then rotates to the horizontal position, and moves racks 166 to the right until the look-ahead rack sensor 210 detects a rack on the look-ahead offline platform 154. Look-ahead offline platform 154 retracts, allowing the look-ahead barcode reader 162 to read the barcodes.

After reading the barcodes, the look-ahead offline platform 154 returns to the original position. Finger 152 moves the rack off the look-ahead offline platform 154 and onto the look-ahead area 155. The rack is here until aspiration offline platform 158 is available. Once the aspiration offline platform is available, finger 152 moves the rack onto aspiration offline platform 158 until the aspiration rack sensor 220 detects the rack on aspiration offline platform 158. Aspiration offline platform 158 then retracts into SPM 30 allowing the aspiration barcode reader 164 to read the barcodes.

Next, specimen robot 66 (see FIG. 3) obtains samples from the sample tubes 167 in the rack 166. Aspiration offline platform 158 then returns to the original position. Finger 152 moves the rack off the aspiration offline platform 158 to the output area 164. The rack is held in the output holding area 164 until the output tray area 162 is available. Finger 152 moves the rack onto a tray in output tray area 162. Finally, the output tray is removed from instrument 10.

5.3.3 Reaction Vessel Handling and Supply Assembly

Figure 11:
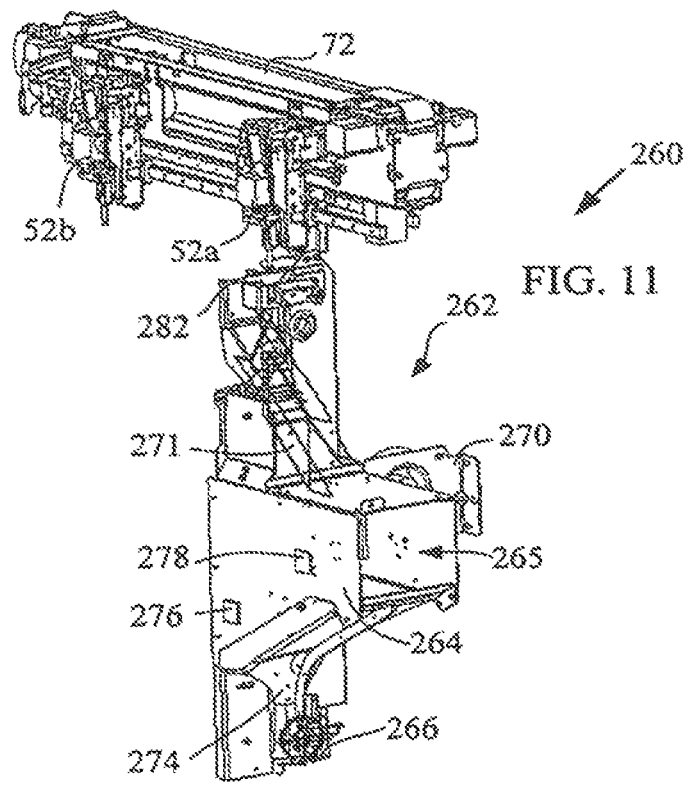
FIG. 11 is a perspective view of a reaction vessel ("RV") handler and supply assembly according to an embodiment of the present invention.

Referring to FIG. 11, reaction vessel handing and supply assembly 260 generally includes a reaction vessel supply 262 ("RV supply 262") and two reaction vessel handlers 52a and 52b. RV handlers 52a, 52b and their associated motors and components are also collectively referred to herein as RV handler sub-assembly 52 or simply RV handlers 52.

5.3.3.1 Reaction Vessel Supply

FIGS. 11-16 depict a reaction vessel supply system 262 according to an embodiment of the present invention. Reaction vessel supply system 262 generally includes a reaction vessel supply bin 264, or hopper, a reaction vessel supply motor 266, belt 268, fans 270, and belt guards 272. Reaction vessel supply system 268 stores enough reaction vessels to supply device 10 for a long period, e.g., six or eight hours or more, of continuous operation. Reaction vessel supply system 262 also presents reaction vessels to a position where the reaction vessel handlers 52a, 52b can retrieve them. The maximum time interval between presentations of reaction vessels to pick up position is preferably 45 seconds or less, more preferably 33 seconds or less. Reaction vessel supply system 262 stores reactions vessels in a clean environment such that the reaction vessels do not become contaminated and interrupt the integrity of results of device 10.

Referring to FIGS. 12-14, RV storage sub-system 262 includes a lugged belt that loops through bulk storage bin 264, or hopper 264, which has a funnel shaped section 274 at its bottom. A geared down stepper motor 266 is used to drive belt 268 through storage bin 264, mixing RVs and collecting RVs with pick up lugs 269 attached to belt 268. RVs that are picked up and reach the top of the belt's 268 travel are detected by an optical through beam detector 280. Two static wedge shaped belt guards 272 and a fan style blower 270 with duct 271 remove RVs that are incorrectly presented by lugs 269 before they reach optical beam detector 280. Lugged belt 268 is stopped whenever a RV is detected. RV handler 52a is then used to transfer the detected RV into incubator carousel 57 for use in the assay process.

The RV supply bin 264 includes a front-loading style door 265 that acts as a chute, when opened, to gather any errant RVs. The operator can add RVs to the RV Supply (without interrupting instrument operation) at any time by simply opening door 265 and adding RVs. RV supply belt 268, also known as hopper belt 268, is located at the rear of the RV supply bin 264.

RV supply bin 264 has two sensors 276, 278 to determine the RV level in supply hopper 264. Sensors 276, 278 are preferably infrared through beam sensors. In one embodiment, sensors provide feedback when the RV level drops below an amount sufficient to provide a specified amount of run time, e.g., over an hour of instrument run time at 100 RVs per hour, and to detect when the RV supply bin 264 has been refilled. For example, the "high" sensor 278 might detect an approximate RV full level as approximately 800 RVs and "low" sensor 276 might be set for approximately 200 RVs.

Referring to FIGS. 13A-13C, the presence of an RV 290 in a belt lug 269 is determined by RV presentation optical sensors 280a and 280b. These sensors determine when RV 290 has been picked up by RV Supply belt 268 and has arrived at the presentation position 282 (location where RV Handler 52a picks up supply RVs). These sensors 280a, 280b are located at the top of the supply belt 268.

In one embodiment, sensors 280a and 280b are dual infrared through beam sensors that permit differentiation between a lug 269 containing a RV 290 (as shown in FIG. 13A) and an empty lug. Beam sensors 280a, 280b are positioned so that RV 290, if present, breaks the beam of sensor 280a and beam of sensor 280b is broken by belt lug 269.

As an empty lug 269 passes through the detection point 282 sensors 280a and 280b see the logic pattern in FIG. 13B. As a lug 269 containing a RV 290 passes through the detection point sensors 280a and 280b see the logic pattern in FIG. 31C. The dotted line indicates when the hopper control software would stop the belt 268 and wait for the RV handler 52a to remove RV 290. Both through beam sensors 280a, 280b, preferably employ a modulated signal to reduce sensitivity to ambient light conditions.

Referring now to FIG. 14, RVs are moved from the supply bin 264 to the presentation point 282 by a motor 266 and belt 268 drive system. Motor 266 is preferably, although not necessarily, located below supply bin 264 as shown. Motor 266 and its associated gears, e.g., lower pulley 288 and drive belt 271, move lug belt 268 around lower and upper pulleys 288 and 291, respectively. As belt 268 turns, lugs 269 move through RV supply bin 264 and pick up RVs 290. Lugs 269 are preferably specially designed to pickup one RV 290 at a time regardless of the RV's orientation within the supply bin 264.

Fan 270 and belt guards 272 are designed to ensure that only one RV is presented to RV Handler 52a. Fan 270, here mounted on the side of the RV Supply Bin 264, essentially blows any incorrectly positioned or additional RVs off belt lugs 269. Belt guards 272, located in the vertical corridor between the RV supply bin and presentation point 282, provide a direct physical barrier to incorrectly positioned or additional RVs on belt lugs 269. Additionally, a stainless steel rooftop may be mounted to the Supply Bin body to physically remove any improperly positioned RVs.

Referring to the block diagram of FIG. 15, optical sensors 280a, 280b and hopper sensors 276 and 278 are associated with one or more printed wire assemblies, e.g., PWA 284, which communicates with backplane 200. In addition, RV supply motor 266 and belt 268 are monitored by RV supply step optical sensor 286 to determine if step-loss is occurring during movement of belt 268. In this embodiment, sensor 286 is preferably located on rotational gear 288 used to move the belt. When a step-loss (error or collision) is detected, the drive current to motor 266 is removed in an effort to minimize the possibility of damaging carousel 56 or the object it has collided with. During the movement of motor 266, the control software calculates the exact time when the encoder will be in the middle of either a slot or the adjoining rib. The software then checks at each calculated time to compare the sensor 286 state to the predicted state. If a discrepancy is detected, a position error is reported.

In one embodiment, reaction vessels are presented within the following approximate tolerances: Z-axis, +/−1.0 mm; Y-axis, +/−1.0 mm, X-axis, +/−0.5 mm. In some cases, such tolerances may be preferable to help avoid reaction vessel jamming in the pickup lugs or not being correctly placed into incubation carousel 57.

The drive torque applied to the belt may be increased by the use of a reduction drive, e.g., a 15:80 or similar reduction drive, on motor 266. Also, belt pulleys 288, 290 preferably have ridged edges to maintain belt alignment and are preferably mounted with their axes approximately square to belt 268 centerline. A user interface, e.g., interface 44 on computer 40, notifies a user when the RV supply hopper 264 needs to be refilled.

Optionally, the RV supply assembly 260 includes a timeout feature. For example, if the RV belt 268 is unable to pickup and present a RV within a defined period of time, e.g., 30 or more seconds from the last presentation, the RV supply assembly 260 will cease operation and the instrument 10 will notify the user via the user interface 44.

In use, host computer 40 or a control subsystem determines that an RV is required and causes stepper motor 266 to drive belt 268 through supply bin 264, mixing RVs and collecting RVs with pick-up lugs 269. RVs that are improperly picked up or positioned, are then removed by belt guards 272 and a fan 270 before they reach presentation point 282. At presentation point 282, optical beam detectors 280a, 280b detect the presence of an RV 290 and a lug 269. The lugged belt is stopped when a RV 290 is detected within a lug 269. RV handler 52a then transfers the presented RV 290 into incubator carousel 57 for use in the assay process.

5.3.3.2 Reaction Vessel Handlers

FIGS. 16 to 21 show a reaction vessel handler sub-assembly 52 according to an embodiment of the present invention. Reaction vessel handler assembly 52 generally includes horizontal drives 302a, 302b and vertical drives 304a, 304b, gripper assembly 306a, 306b, and horizontal tracks 300 on common gantry 72. Reaction vessel handler assembly 52 moves reaction vessels 290 from various locations to other locations, automatically aligns the reaction vessels 290 at pick-up, detects the presence of reaction vessels held within the gripper assembly 306a, 306b, and provides feedback of RV handler 52a, 52b location and status to the computer 40. In a preferred embodiment, reaction vessel handler assembly 52 includes two reaction vessel handlers 52a, 52b, operating simultaneously to increase the efficiency and speed of system 10.

Referring back to FIG. 3, RV handler assembly 52 cooperates with specimen rack handler 50, incubation and separation carousel assembly 56, RV storage supply 262 and RV waste 64 assemblies. Each RV handler 52a, 52b interfaces with different components of the instrument 10. In some cases, they may interact with the same component but they do so at different locations. TABLE 1 provides examples of RV handler 52a, 52b interaction with other components. Additional details of the interaction between the various component modules and subassemblies will be described herein in more detail in later sections.

TABLE 1

Reaction Vessel Handler Interactions

| RV Handler | Interacts with |
| --- | --- |
| RV Handler 52a | RV Supply 262 |
| | RV Waste 64 |
| | Detector Transfer Robot 74 |
| | Separation Carousel 55 |
| | Incubator Carousel 57 (all three rings) |
| RV Handler 52b | Separation Carousel 55 |
| | Incubator Carousel 57 (two outer rings only) |

Figure 17:
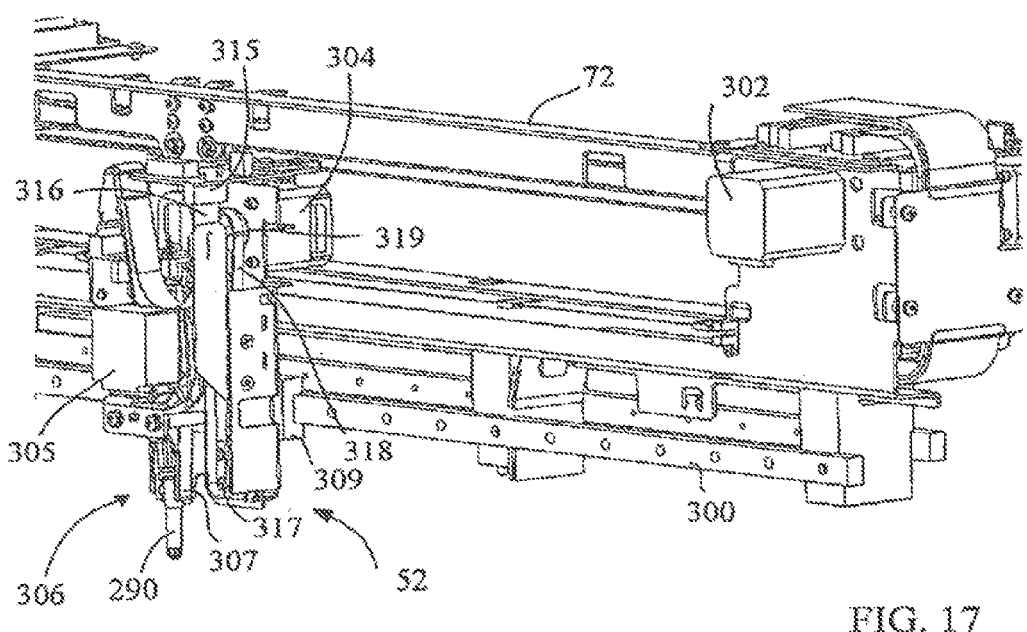

Referring to FIG. 17, each of the RV handler mechanisms 52a and 52b includes a common horizontal linear travel axis 300 (y-axis) upon a common gantry 72 and separate but preferably, although not necessarily, similar gripper assemblies 306a and 306b, which include a vertical linear axis (z-axis) and gripping axis (theta axis).

Each RV Handler 52a, 52b is associated with a horizontal drive 302, a vertical drive 304, and a gripper assembly 306, respectively. Note that because RV handler 52a, 52b include essentially the same components and sub-assemblies, the terms RV handler assembly 52, horizontal drive 302, vertical drive 304, gripper assembly 306, etc., are occasionally used herein without using "a" or "b" to designate a particular RV handler.

Horizontal Drives 302 move the RV Handlers 52 horizontally (e.g., along y-axis) along gantry 72. Motor 266 and associated gearing are mounted on the stationary gantry 72. RV Handlers 52 are attached by slide 309 to rail 300 and attached to motor 302 by belt 312 such that motor 302 and associated gearing drive belt 312 and move RV handler along rail 300.

The horizontal range of motion for RV Handler 52a is constrained to travel over the RV supply 262, incubator carousel 57 (e.g., forward half only), separation carousel 55 and the detector robot 74. The horizontal range of motion for RV Handler 52b is constrained to travel over incubator carousel 57 (rear half only) and separation carousel 55.

Horizontal drive 302 preferably has two sensors to determine its position. A horizontal home optical sensor preferably determines the horizontal home position of the RV handlers 52. Horizontal step optical sensor preferably determines the horizontal position of the RV Handlers 52. Both sensors are preferably located on gantry 72.

Vertical Drive 304 moves grippers 307 vertically (z-axis) on the RV Handlers 52a, 52b. Motor and gearing of vertical drive 304 are mounted in the moving RV Handler 52a, 52b. Gripper assembly 306 rides on a rail bearing 316 (located vertically within the RV Handler 52) and is attached to the motor and gearing 304 by a belt 318 and pulleys 317, 319. In this embodiment, although not necessarily, vertical range of motion for both RV handlers 52a, 52b is approximately the same and constrained by hard stops 315 located at the end of the rail bearing.

To prevent RV handlers 52 from dropping a RV when the power is interrupted (either power loss or e-stopped), the vertical drive control circuitry incorporates a dynamic braking feature preferably. During dynamic braking, gripper head 306 is prevented from free falling by the back EMF created in the motor winding. The dynamic braking circuitry works by shorting the windings of the vertical axis stepper motors with a relay connected to the 24V power supply. Since the drive current to the stepper motor is provided by the same power supply it ensures that dynamic braking is enabled as soon as the drive current is interrupted.

Vertical drive 304 has two sensors to determine its position. A vertical home optical sensor, preferably located on the RV handler 52 determines the vertical home position of the RV Handler. A vertical step optical sensor, also preferably located on RV handler 52, determines the vertical position of the RV handler 52.

Figure 18A:
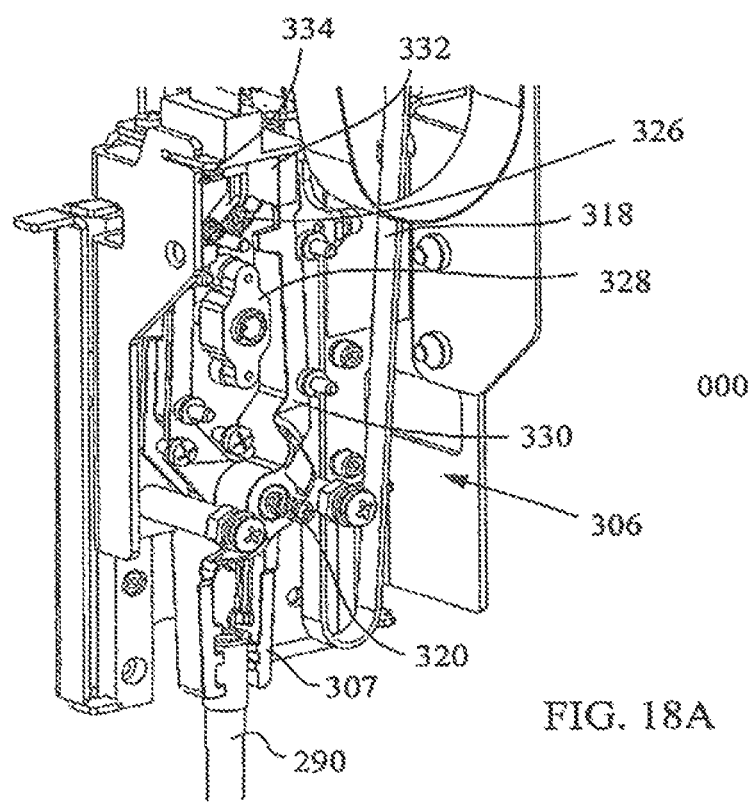
Figure 18B:
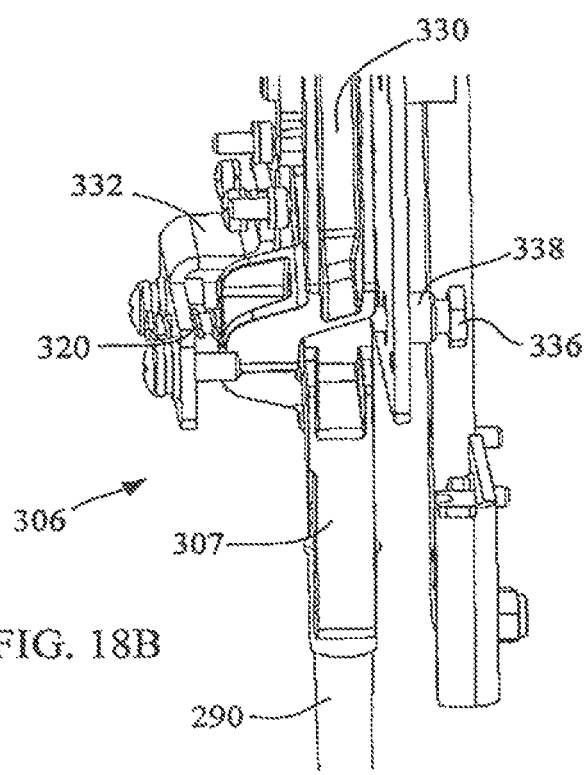
Figure 18C:
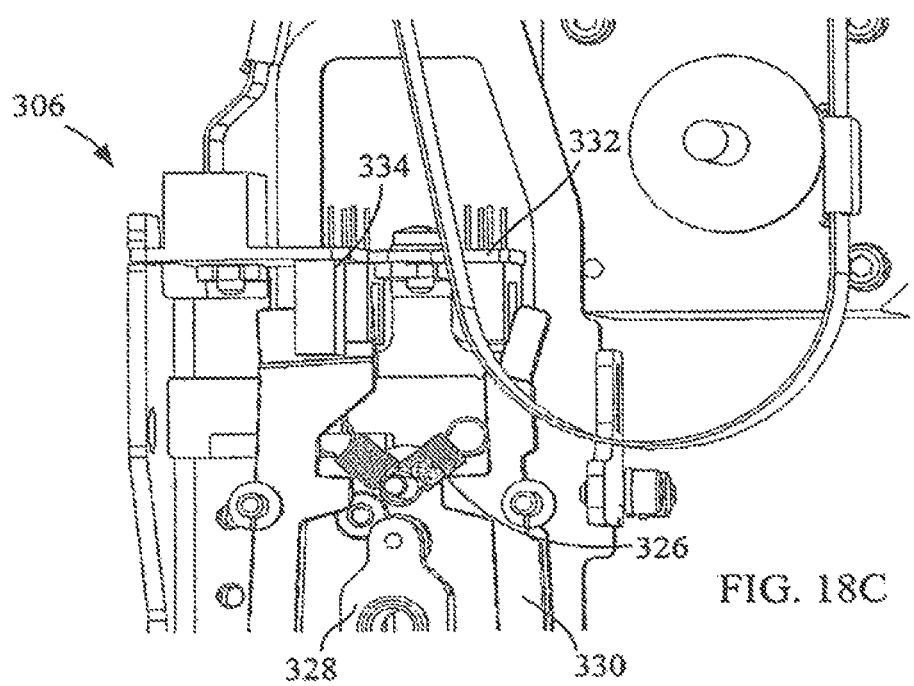

FIG. 18A-C shows additional detail of gripper head assembly 306 with FIGS. 18A and 18C having gripper drive motor 305 and support bracket 332 removed. In this embodiment, gripper assemblies 306 employ a cam driven scissor 330 mechanism actuated by a stepper motor 305. The motor 305 and cam are mounted on the gripper assembly 306. Gripper assembly 306 uses coil springs 320 and specially designed gripper jaws 307 to provide a consistent gripping force and compensation for misalignment of RVs.

Sealed ball bearings can be are used in both jaws to prevent wear and increase alignment accuracy. Due to the light axial spring load on the gripper jaws 307 no spacer has been used in this embodiment to separate the bearings in each jaw. Both jaws are lightly spring 320 loaded against the alignment/pivot pin 336. FIG. 18B shows the alignment pin 336, gripper jaws 307 and spring 320. A nyloc nutsert 338 prevents pivot pin 336 from moving. The thread on the alignment pin is preferably cut undersize to permit alignment to the gripper motor bracket 332.

Referring to FIG. 18C, gripper assemblies 306 use one or more, e.g. two, optical sensors 332, 334 to determine if an RV 310 is present in the gripper jaws 307. Sensors 332, 334 are located on each RV Handler 52a, 52b. Each sensor 332, 334 monitors one side of gripper jaws 307.

In one embodiment, flexible wire cables are used to prevent fatigue failures for the moving components on the vertical and horizontal axes. The thin nature of the cable helps minimize stresses within the wires thus maximizing fatigue life. The cables are capable of, e.g., greater than 5,000,000 moving cycles with a minimum bend diameter of approximately 40 mm or more. The cables are preferably constrained in both the vertical and horizontal directions to limit bending. The cables are also routed to avoid rubbing on potentially damaging surfaces. Strain relief is provided by mechanically clamping the cables to a connection point.

Gripper jaws 307 are aligned in the x-axis (e.g., left to right in FIG. 18B) by adjusting alignment pin 336 that runs through the gripper jaws.

Figure 19A:
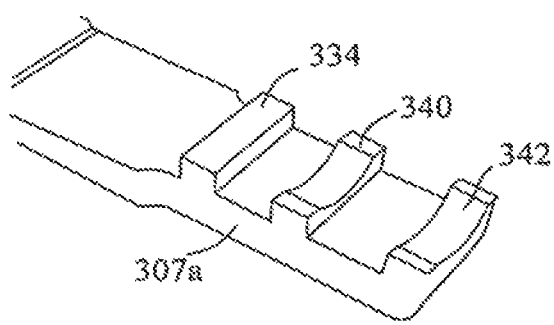
Figure 19B:
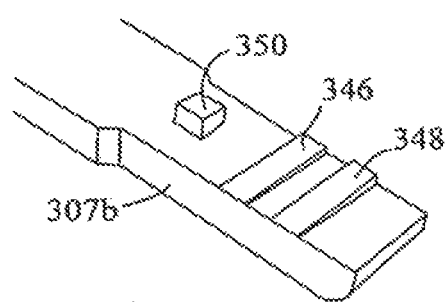

Referring to FIGS. 19A and 19B, in one embodiment gripper jaws 307 include two jaw pieces 307a and 307b. Each jaw piece 307a and 307b includes grip features, e.g., 340, 342, 344, 346, 348 and 350, to position and hold RVs. Examples of grip features for a primary 307a and secondary 307b jaw piece are shown, however other grip patterns or features may be used. In this embodiment, primary jaw 307a of FIG. 19A includes two contoured grip features 340 and 342 configured to position and hold RVs in a vertical orientation. A rib 344 helps prevent upward sliding of an RV. Secondary jaw piece 307b includes a single point of contact 348 that contacts the side of an RV and helps hold it against features 340 and 342 of primary jaw. A second, smaller, feature 346 only contacts the upper flange of an RV (see FIG. 21) if the RV is pulled vertically out of jaws 307. An upper rib 350 prevents upward shifting of an RV in the event of a collision.

Referring to the block diagram of FIG. 20, motors 302, 304 and 305 of RV handlers 52a and 52b communicate with backplane circuit board 200 through RV handler gantry circuit board 356. RV handler vertical motor 304 communicates through RV handler head circuit board 354. Gripper motor 305 communicates with gripper motor board 352, which communicates with RV handler head circuit board 354. One skilled in the art will appreciate that a different arrangement of circuit boards or other control features may be employed.

5.3.3.3 Reaction Vessel (RV) Design

Referring to FIG. 21, a typical reaction vessel 290 according to the present invention employs a non-nesting design compatible with the hopper style RV supply system 262 described herein. RV 290 generally is dimensioned as a tube or vessel having a body 368 and an open end 360. External ribs 366 at end of RV opposite opening 360 help prevent nesting with other RVs. In addition, a flange 362 provides an upper stop surface for grippers 307 and extends internally to form a lip on the inside of RV opening to further reduce possibility of RV nesting. A locating shoulder 364 provides a lower stop surface for grippers 307 and may be used to support RV 290 when placed in a nest or carousel such as incubation and separation carousel 56. RV 290 preferably includes similar internal geometry as the existing B-R RVs (BIO-RAD part no. 223-9391) over the bottom half of the RV.

5.3.3.4 Operation of Reaction Vessel Handling and Supply Assembly

During use, RV Handler 52a removes an RV 290 from RV Supply 260 as described previously and places RV 290 in incubator carousel 57 (see FIG. 3). Then, sample and reagent are added to RV 290 using sample handler assembly 66 and reagent robot assembly 60, respectively as described below. RV 290 is incubated for a specified amount of time (chemistry dependent). RV Handler 52b then moves RV 290 from the incubator carousel 57 to the separation carousel 55, where the sample undergoes a wash and separation process within RV 290.

After the wash and separation process, RV Handler 52b moves RV 290 from separation carousel 55 back to incubator carousel 57. Additional reagents or conjugates are added if need. Incubation and washing are repeated as required by the particular assay. After assay preparation is complete, RV handler 52a then moves the RV 290 from the incubator carousel 57, or in some cases from wash and separation carousel 55 or some other location, to the detector transfer robot 74. Typically, interaction of RV 290 with the RV handlers 52a, 52b is finished at this point.

Each RV Handler 52a and 52b is capable of adjustment and alignment with other components of system 10. For example:
- Alignment of RV handler 52a to the incubator carousel 57 (all three rings) in the x-y-z directions.
- Alignment of RV handler 52a to the separation carousel 55 in the x-y-z directions.
- Alignment of RV handler 52a to the detector robot 74 in the y-z directions.
- Alignment of RV handler 52a to RV supply 260 in the y-z directions.
- Alignment of RV handler 52a to RV waste 700 in the y-z directions.
- Alignment of RV handler 52b to the separation carousel 55 in the x-y-z directions.
- Alignment of RV handler 52b to the incubator carousel 57 (two outer rings only) in the x-y-z directions.

5.3.4 Specimen Handler Assembly

FIGS. 22-24 show a specimen handler assembly 66, also termed herein "sample handler assembly 66", "sample handler 66" or "specimen handler 66", according to an embodiment of the present invention. Sample Handler assembly 66 includes a number of subsystems and components, including a specimen probe 370 (also termed "sample probe"), a sample robot 380, a sample liquid level sensor 390, a blockage detection sensor 392, and a clean station 90.

Specimen probe 370 is designed to aspirate and dispense specimens and be easily cleaned in clean station 90. Sample robot 380 preferably includes a probe mount 376 for holding sample probe 370 and moves probe 370 in the y and z directions, e.g., horizontally along gantry 72 and rail bearing 382 and vertically to engage sample tubes 167 and RVs 290. Similar to RV Handlers 52, which are located on opposite side of gantry 72, sample robot 380 is driven by a horizontal and vertical motors such as stepper motors 384, 386 (see FIG. 23). One or more optical sensors 388 provide accurate monitoring of probe 370 position.

Generally, sample handler 66 aspirates a sample from the specimen rack handler 50 and dispenses the sample into an reaction vessel 290 held on incubator carousel assembly 56. Sample handler 66 monitors specimen probe 370 for any loss of function or blockage, minimizes dead volume required using liquid level sensing, and minimizes the amount of sample used. Sample handler assembly 66 also cleans the specimen probe 370 to minimize any carryover between samples and/or reagents and provides the ability to sample various volumes.

5.3.4.1 Sample Probe

Sample, or specimen, probe 370 is designed to aspirate and dispense samples and undergo easily cleaned. Referring to FIG. 23, sample probe 370 includes a head 372 for engaging with probe mount 376 of robot 380 (FIG. 22) and a tapered tip 374. Internal diameter of the lumen 376 of probe 370 is preferably reduced at tip 374 to enhance dispense accuracy. Sample probe preferably uses a dual cavro pump system (discussed below with respect to system fluidics) to aspirate, dispense and clean. A smaller, e.g., 250 µL, syringe performs the aspiration and dispense functions while a larger, e.g. 2.5 mL, syringe performs the cleaning function. Probe lumen 376 is fluidly connected with system 10 fluidics through tube 378 (see FIG. 22) attached to probe mount 376. In a preferred embodiment, sample probe 370 is replaceable and shares a common design with reagent probe 61. Additional features of the sample/reagent probes are described in section 5.3.5 below.

Sample probe 370 is preferably mounted on an electrically insulated material, which facilitates the operation of the sample handlers liquid level sensing (LLS) system 390 described below.

5.3.4.2 Sample Robot

Sample robot 380 is designed to mount the sample probe 370 and move the probe in vertical and horizontal directions along gantry 72. Referring to FIG. 24, stepper motors 384 and 386 provide the motion in each axis using a pre-tensioned belt (e.g., belt 383 of FIG. 23 connects to horizontal motor 384 on opposite end of gantry 72). Optical sensors provide accurate monitoring of the probe position. For example, a horizontal step optical sensor 388 determines the horizontal position of sample robot 380. This sensor is preferably located on the gantry. Optionally, a horizontal home optical sensor also located on gantry 72 determines the horizontal home position of the sample robot 380. Similar to RV handlers 52, vertical home optical sensors and vertical step optical sensors can be located on sample robot 380 may be used to determine the vertical home position and instantaneous position, respectively, of robot 380.

5.3.4.3 Sample Liquid Level Sensing (LLS) and Blockage Detection

The LLS system 390 is designed to detect the entrance and exit of the sample probe 370 from liquid. The LLS uses the change in capacitance that occurs when a probe enters or exits liquid. Due to the small change in capacitance that occurs, stray capacitance is minimized by electrically isolating the sample probe 370 using a relatively non-conducting probe head 372 and mount 376 compared with conducting body of probe 370.

Sample blockage detection 392 includes a pressure sensor that monitors the pressure variations that occur during aspirating or dispensing samples. The pressure ranges that occur during normal (good) aspiration and dispense are well known. When a probe becomes blocked the pressure variations change and fall outside of the known values. When this occurs, an auto-recovery is initiated by host 40. Probe 370 is cleaned using pre-defined protocols. If this does not correct the problem, the user is notified to take corrective action.

5.3.4.4 Clean Station

Referring again to FIG. 23, clean station 90, mounted on SPM 30 chassis near the incubation and separation carousel 56, is designed to clean probe 370. Probe 370 is cleaned before and after each sample aspiration and dispense. To achieve the carryover specifications, a two stage clean station 90 is used. In the first clean stage, probe 370 discharges directly into drain 400 (which carries contaminated liquid away). Then, in the second clean stage, the probe moves into a well 402 where liquid 404 (e.g., wash buffer) is pumped through the probe and fills well 404. In this stage, the inside and outside of probe tip 374 are washed. Vacuum extraction through port 402 is used to remove used wash fluid 374.

5.3.4.5 Example of Operation of Sample Handler Assembly

In use, after sample probe 370 is cleaned in the clean station 90, probe moves vertically to the home position over a specimen rack located on aspiration platform 158 of rack handler 50. Robot 380 moves probe 370 vertically down until specimen liquid is detected by the LLS system 390. After liquid detection, the sample robot 380 moves a fixed distance further into the liquid and the specimen is aspirated. During aspiration, blockage detection system 392 monitors the aspiration pressure to determine if the sample probe is blocked (either partially or completely). Additionally, during aspiration the sample robot 380 moves the probe down to ensure the probe stays in the liquid. After aspiration, sample robot 380 moves to vertical home position. During this movement, the LLS system monitors the liquid level to ensure the probe exit from the liquid is at an expected position.

Specimen handler assembly 66 then moves horizontally along gantry 72 to incubator carousel 57 and down to set position for specimen dispense. The specimen is dispensed into an RV on the incubator carousel 57. Sample Robot 380 then moves sample probe 370 back up to the vertical home position. Specimen handler assembly 66 moves horizontally back to clean station 90 stage one clean position 400. Sample robot 380 then moves sample probe 370 down to the clean station 90 and discharges the over-aspirate volume and a set amount of buffer into clean station 90. Sample robot 380 moves sample probe 370 to the stage two clean position 374. Wash Buffer is pumped through the sample probe 370 into the clean station 90 to clean both the inside and outside of the probe. Finally sample robot 380 returns to the vertical home position.

5.3.5 Reagent Storage Assembly

5.3.5.1 Overview of Reagent Storage Assembly

FIGS. 25-32 depict the components and relative functions of a reagent storage assembly 58 according to an embodiment of the present invention. In particular, FIGS. 25 and 26 depict reagent storage assembly with storage lid 412 open (FIG. 25) and closed (FIG. 26). Reagent storage 58 generally includes a reagent cooler 410, rotational and agitation drives 440, 441, a barcode reader 442, reagent carousel 70, pack piercer 420, and a pack lid opener 430. The reagent storage generally stores reagents under favorable conditions. Preferably, the temperature of the reagent storage is at least about 8° C. and at most about 10° C. Reagent storage 58 also maintains bead homogeneity, preferably within about ±5 percent, both horizontally and vertically, within the reagents. Reagent storage 58 also preferably can store up to 20 reagent packs within a removable carousel. The reagent storage preferably maintains performance characteristics in an ambient temperature of at least about 15° C. and at most about 30° C. Reagent storage minimizes dead volume within reagent bottles, minimizes reagent loss through evaporation, identifies reagent packs with barcodes, allows a user to change individual reagent packs and/or change or remove the entire reagent carousel 70. Furthermore, reagent storage automatically opens reagent pack covers to aspirate reagents and automatically pierces the reagent bottle caps prior to reagent aspiration.

In one embodiment, the reagent carousel 70 preferably includes twenty or more variable reagent pack or kit positions

456. Two or more of the positions preferably contain a detector clean kit (70% isopropyl alcohol) and a detector calibration kit (two bead sets stored in separate bottles). The assay panel reagent kits each preferably contain up to four liquid reagents. Also, the reagent motor movement is bi-directional. The reagent carousel is chilled to about 2-8° C. while the assay incubator is kept at about 37° C. (±0.5° C.). The temperature of the refrigerated reagent compartment is maintained by compressed liquid refrigeration mounted beneath the incubator.

Additional details regarding components and sub-assemblies of reagent storage assembly 58 are described below.

5.3.5.2 Reagent Cooler

Reagent cooler 410 maintains a relatively constant ambient temperature, e.g., between approximately 8° C. and 10° C., within the reagent storage 58. Reagent cooler 410 accomplishes this using an insulated housing 411 and a vapor compressor 445 or other refrigeration mechanism to cool the reagents.

In one embodiment, cooler 410 includes a 12/24V vapor compressor 445 unit with a charge of, e.g., 132A refrigerant, an air-cooled condenser to dissipate heat, a fan to force air through the condenser, a drier to remove excess moisture from the refrigerant, a capillary tube expansion valve, a stainless steel tub evaporator 411 or housing which surrounds the reagents and provides cooling, insulation 413 around the evaporator tub to provide insulation and prevent external condensation; and an insulating lid 412 to prevent heat flow into the system.

Evaporator tub 411 is preferably stainless steel or the like and surrounded by structural foam insulation 413. The stainless steel provides high durability and consistency of manufacture, while the structural foam minimizes the heat conducted into the refrigeration system through the evaporator walls and reduces condensation on the exterior surfaces of the reagent storage 58. A structural foam thickness of approximately 17 millimeters is desirable to helps prevent potential condensation under ambient conditions of 40° C. and 90% RH, however other types and thicknesses of insulation may be used. A capillary tube can be used as a refrigeration expansion valve.

Reagent cooler lid 412 provides insulation for the top of reagent cooler 410, and access to the reagent carousel 70 for the reagent probe 60, reagent pack piercer 420, and reagent pack lid opener 430. In a preferred embodiment, reagent cooler lid 412 is moved by the same motor and drive assembly as the pack piercer 420 discussed below. A lid home optical sensor, e.g., similar to other optical sensor described herein, determines the home position of lid 412. This sensor preferably is near pack piercer/lid motor and gearing 446.

5.3.5.3 Rotational and Agitation Drives

Referring to FIG. 26, rotational drive 440 is a belt-driven turntable powered drive motor. In one embodiment, rotational drive employs a 48-volt motor, although other motors may be used. Rotational drive 440 moves rotates carousel the reagent packs (rotationally) to the various positions required for pack piercing, reagent aspiration and pack presentation (for replacement).

Agitation drive 441 performs the two functions of agitating the reagent bottles and lifting the reagent carousel 70 up to the installation/removal position. Preferably, the same drive motor is used in both functions. A simple clutch of two pins (moving in slots) on a lead screw/sun gear assembly 450 (e.g., see FIG. 27B) is used to accommodate each function. The agitation drive 441 agitates the reagent bottles by rotating lead screw/sun gear assembly 450, 451, e.g., a the 75-millimeter lead screw/sun gear assembly 450, 451, back and forth.

The sun gear 451 then rotates two rows of planetary gears 452, which include heads 453 upon which the reagent bead bottles sit.

Planetary gears 452 include a plastic bushing, which sits on a stainless steel bearing, to eliminate potential corrosion. Planetary gears 452 are supported on 3 mm stainless steel pins with spherical tops. In a preferred embodiment, sizing and finish of the pin was chosen to minimize wear between the pin and the hub of the planetary gear. The pin length was chosen to elevate the planetary gear hub above any fluid that may be present in the drive mechanism.

The motor agitation 441 lifts or lowers the reagent carousel 70 by rotating pins (in either direction) and engaging the lead screw. Once the pins have engaged the lead screw/sun gear 450, 451, the reagent carousel 70 is raised or lowered. To balance the friction forces while raising and lowering the lifting platen 455, vertical guide pins 457 are positioned symmetrically on the turntable. In this embodiment, a 75 mm lead screw 450 was chosen to provide stability for the lifting platen 455 in the raised position. The lead screw/sun gear 450, 451 and platen gear materials were selected for their noise and wear reduction properties. Example gears and suggested suitable materials are listed below in TABLE 2.

An agitation drive home optical sensor located on the rotational gear driven by the agitation drive motor 440 can be used to determine the rotational home position of the Agitation Drive.

An agitation drive proximity sensor can be used to determine a vertical home position of the agitation drive 441 and to determine if a reagent carousel 70 is loaded. This sensor is preferably located on a post that penetrates the tub floor.

The vertical position of the lifting platen 455 can be determined by rotating the turntable to align a pin, e.g., steel pin 457 on the bottom of the lifting platen and the proximity sensor. The lifting platen 455 can then be homed by lowering the platen until the pin 457 actuates the proximity sensor. The proximity sensor detects the presence of a reagent carousel 70 by detecting one or more pins, for example four steel pins, that are pushed to the same level as the home steel pin when a reagent carousel is loaded. In one embodiment, proximity sensor is a reed switch.

A rotational drive home optical sensor can be used to determine the rotational home position of rotational drive 440. This sensor is preferably located on the rotation gear driven by the rotational drive motor.

The addition of a reagent pack to carousel 70 may cause the agitation drive to agitate the reagent packs continuously for four minutes to ensure the complete suspension of the bead.

5.3.5.4 Barcode Reader

Referring to FIG. 27B, reagent pack barcode reader 442 views barcodes on reagent packs 80 (See FIG. 28) through a heated window 443 on the reagent cooler 410. In one embodiment, barcode reader 442 type is a MICROSCAN 710 reader. Other barcode readers are known and may be suitable.

The barcode reader window 443 is heated to prevent external and internal condensation. The electrical resistance of the heating element is, e.g., between 30-100 Ohms. The barcode reader heated 443 window operates whenever reagent storage 58 is refrigerated. The control algorithm is a simple open loop that modulates the drive current to window 443 to match the resistance of the window and the ambient temperature.

5.3.5.5 Reagent Carousel and Kits

Referring to the embodiment depicted in FIGS. 28A-C, prior to use, both the bead and conjugate reagents are stored in packs 80 contained within reagent carousel 70. Reagent carousel 70 is removable and has slots 465 for holding up to twenty or more reagent packs 80. Each pack 80 has capacity for up to four bottles 82, e.g., 2 bead bottles and 2 conjugate bottles. In some cases, diluent or other reagent fluids may be provided. Whether each bottle gets used in a particular pack is chemistry dependent. All reagent packs are identifiable, e.g., barcoded 472, preferably during the manufacturing process. Barcode 472 includes information such as reagent type, bead lot, expiration date, etc.; Barcode 472 is preferably located on the outer end of reagent pack 80 enabling identification after it is inserted into one of slots 456 of carousel 70.

To limit reagent and conjugate evaporation as well as preventing dust and other particles entering the bottles, the reagent pack 80 (also termed reagent kit or reagent cartridge) design incorporates two levels of seals. A primary foil seal covering each bottle is used to prevent spillage and evaporation during shipping and prior to use. A secondary seal, or flip top lid 470 covers all reagent bottles 82 in pack. The lid can be connected to a pushrod mechanism inside the individual reagent pack 80 and spring loaded in the closed position as shown in FIG. 28A. As the pack lid opener pushes down on the pushrod as described below, lid 470 is forced open on this individual pack.

Examples of a bead reagent bottles are shown in FIGS. 28B and 28C. Reagent bottles 82 include an access hole at top of bottle 82 to allow reagent transfer robot 60 access. A lip 461 on top edge serves as an attachment point for foil sealing which covers hole 460 until reagent is ready for use, at with time foil seal is pierced by pack piercer 420. A vertical rib 462 on the side of bottle 82 promotes vertical mixing of the bead suspension. Without such rib 462 or other mechanism, significant vertical gradients in bead concentration may exist even with high levels of agitation. Radial ribs 464 across bottom of bottle 82 engage planetary gear heads 453 to facilitate agitation when the beads have settled out of suspension. A circumferential rib 469 on bottom helps centralize bottle 82 on planetary gear heads 453. A relatively conical or tapered bottom 466 helps minimize dead volume. During storage outside of the instrument 10 or transportation the beads may settle out of suspension and typically concentrate in the lowest point in the bead bottle, which in this case is an approximately flat bottom, e.g., approximately 6 mm in diameter, to distribute settled beads. Other versions of the bead bottle have a conical center, however, when the beads settled they may form a tight clump in the center of the bottle and may be difficult to re-suspend. With a flat portion 468 on the bottom, settled beads form a thin film across the entire flat surface instead of clumping and may require less agitation during re-suspension.

Reagent pack 80, also termed reagent kit or cartridge, can be stored on the instrument once opened, and includes the appropriate reagents to carry out sample testing, wash solution is typically, although not necessarily supplied separately by the system fluidics. In one embodiment, each reagent kit includes one bottle of sample diluent, one bottle of coated magnetic beads, and one bottle of conjugate as shown in FIG. 28A. Preferably, pack 80 includes enough reagent material to carry out a large number of tests, e.g., 100 tests.

Reagent kits 80 may contain reagents including beads that allow the end user to control and monitor the quality of results for each individual sample. For example, two specific bead "regions" may be used. First, in order to ensure an appropriate sample has been added to the reaction, the M.A.D. system chemistry can employ a bead called "Serum Verification Bead." This bead ensures that either serum or plasma was used in the assay, and that the appropriate volume of sample has been added to the reaction. If samples other than serum or plasma (i.e., urine, cerebral spinal fluid, nasal aspirates etc.) are used in the assay, or if the incorrect volume of sample is added to the reaction vessel, the Serum Verification Bead will identify a possible issue, and flag the results. Second, in order to ensure consistency of reading by the lasers within detector 20, the system chemistry can employ a bead called "Internal Standard Bead." This bead adjusts for variable laser detector response, standardizing the laser for each read.

Reagent carousel 70 also provides an interface between the reagent bottles and the agitation gears 453. Agitation of each reagent bottle 82 about its vertical axis assists to maintain bead homogeneity within the reagents. As described above, reagent storage 58 design rotates individual reagent bottles with an oscillatory motion to achieve consistent homogeneity. The bottle design includes a vertical rib to promote mixing both radially and vertically within the bead suspension. As shown in FIG. 26, each Reagent Pack contains 2 bead bottles, which are agitated by rotating each container about its vertical axis.

Reagent temperature sensors may be used to monitor the temperature of the reagent storage 58. Reagent storage 58 utilizes thermistors temperature sensors, for example two sets of two sensors. One set of thermistors, referred to as air sensors, measure the air temperature within the reagent cooler 410. These sensors provide the primary feedback for the temperature control algorithm. The second set, referred to as the wall sensors, measure the temperature of the evaporator wall. The feedback from these sensors is used to prevent excessive refrigeration of the evaporator and potential icing problems. Redundant temperature sensors are used to assist in troubleshooting during service and maintenance.

5.3.5.6 Pack Piercer

Referring to FIGS. 29A-29C, reagent pack piercer 420 is a sub-system within the reagent storage assembly 58 of the MAD instrument 10. Reagent pack piercer 420 is used to open the primary seal on each reagent bottles 82 in a pack 80 just prior to the first reagent aspiration from that reagent pack 80. Once opened, the primary seal cannot be closed. The secondary seal, or reagent pack lid 470, is used to prevent evaporation after the primary seal is opened.

Reagent pack piercer 420, located on reagent cooler lid 412, includes a drive mechanism 446 attached to the rear of the reagent storage and a piercer arm 421 which extends over the reagent cooler 410 to actuate a number of piercer pins 480, in this case four as reagent packs 80 in this example are designed to hold up to four reagent bottles 82. Piercer arm 421 also supports the reagent storage insulation lid 412 and reagent pack lid opener mechanism 430. The reagent pack piercer 420 is used to open the primary seals on reagent bottles 82 prior to the first reagent aspiration from the reagent pack 80. The primary pack seals are opened by driving the piercer pins 480 down through the sealing foil and to create a set of holes that match the diameter of the piercer pin tips 481 (see FIG. 31A-C). The piercer pins 480 are then retracted so reagent can be aspirated from the reagent pack.

In this embodiment, pack piercer 420 and the reagent cooler lid 412 use the same motor 446. Pack piercer 420 uses the motor only when lid 412 is in the closed position. Once the lid is closed, the motor drives the lever arm 421, with piercers 480, 481 at the end, down into the reagent packs 80.

Drive mechanism 446 preferably, although not necessarily includes the following features. A ball screw drive is used to prevent high friction forces variations due the high working loads. A belt drive is used due to the space constraints and to provide easier service access to the motor. Lead nut is free to float within the retainer so that side loads do not cause excessive wear or degradation to the bearings within the nut. All side loads are carried by two sealed bearings on the lower ends of the drive links. A spherical bearing connects the drive links to the piercer arm 421 to prevent possible binding caused by over constraining the mechanism.

A number of sensors or detectors are association with pack piercer 420. For example, a pack piercer home optical sensor located on piercer arm 421 determines the home position of pack piercer 420 from which the piercers 480 can lower into the reagent packs 82.

A pack piercer/lid step optical sensor determines if steploss is occurring during either pack piercing or lid movement (raising or lowering). This sensor is located on the rotational gearing used to pierce and move the lid.

The pack piercer also uses an optical sensor to detect the position where the insulation lid seals against the evaporator top edge. The design was chosen because it eliminates any problems due to backlash in the reagent lid system.

An optional lid closed sensor 482 using a flag 485 that breaks optical sensor 482 (e.g., see FIG. 31A) serves as a collision detection sensor during the lid lower action. If the lid is obstructed during the lower move the lid will move relative to the piercer arm, the closed sensor is used to flag the collision notifying the software to halt the axis and prompt the user to remove the obstruction.

A pack detector mechanism detects the top of the reagent pack during the pierce stroke. This design uses a spring-loaded pin with a flag 485 that breaks an optical sensor 484. This particular design helps avoid problems due to variation in pack height or backlash in the pack piercer mechanism.

A pierce detector flag 492 and sensor 494 mechanism checks the height of each of the piercer pins at the completion of the pierce stroke, e.g., an elevated pin 480 indicates that the pierce has been incomplete. Because each of the piercer pins is spring loaded, the height of the highest pin is measure via the pierce detector's spring-loaded plate 492 and an optical sensor 494.

A piercer interlock 486 located on the main arm 421 helps prevent piercer probe tips from being exposed while the reagent storage lid 412 is raised.

A mechanical clutch 488, shown in FIG. 30, is optionally included as the drive mechanism may be sufficiently highly geared that a user is unable to back drive the mechanism even if power is not applied to the stepper motor. To prevent operators damaging themselves or the instrument 10, clutch 488 is monitored by a sensor 489. Disengaging the clutch will cause the instrument 10 to Estop.

To ensure alignment to reagent carousel 70, pack piercer 420 optionally utilizes a floating guide block on the piercer tips 481. During initial part of the pierce stroke the floating guide block locates onto the carousel top and centers the piercer pins over the reagent bottles. In one embodiment, guide block can tolerate a +/−2.0 mm or more of misalignment between the piercer mechanism and the reagent carousel.

FIGS. 31A-31C depict a typical operation of pack piercer 420 after piercer is initialized during instrument startup, leaving the reagent lid 412 in the closed position. Prior to the first reagent aspiration from a pack 80 (e.g., 3 to 10 seconds, preferably approximately 6 seconds), reagent carousel 70 is rotated to position the reagent pack 80 directly under the piercer pins 480. Once in position, the pierce probes 481 are driven down. The spring loaded lid actuation pin opens the secondary seal 470 on the reagent pack 80.

The piercer pin guide block 490 engages the reagent carousel and centers the piercer pins 480 over the reagent bottles 82. The pack detection pin touches the top of the reagent pack, trips the optical sensor 484 and sets the pierce depth to which to drive. As the probe tip 481 drives down, the piercer probe tip shoulders 483 bottom out on the bottle tops as shown in FIG. 31C.

Spring loading on each pin 80 takes up the difference in bottle heights while the piercer 481 tip travels to the full pierce depth. At the pierce depth the pierce detection optical sensor 494 senses whether all piercer pins have successfully pierced the pack. After successfully piercing the bottles 82, the piercer pins are retracted and the reagent lid 470 is returned to the closed position.

As mentioned above, pack piercer 420 is also used to open and close the reagent storage lid 412. During a typical open and close procedure, reagent storage insulation lid 412 is closed and held down by gravity. To open the lid, piercer 420 lifts the reagent storage insulation lid to the point where it engages on the underside of the external cover. The piercer continues to lift, raising the external cover to a point where a pulley on the front of the piercer engages in a slot on the external cover. As the piercer continues to lift, the external cover reaches a point where the gas strut overcomes the weight of the cover. The piercer is now required to hold the external cover down. When piercer reaches the top of its travel, lid is fully open and reagent carousel can be raised. To lower the lid the same steps are repeated in reverse.

5.3.5.7 Reagent Pack Lid Opener

FIG. 32 depicts a reagent pack lid opener assembly 430. Lid opener 430 is a sub-assembly within the reagent storage assembly 58 of the MAD system 10. Reagent pack lid opener 430 opens and closes the secondary seal (e.g., reagent pack lid 470) on a reagent pack 80 just prior to aspiration of a reagent. To minimize reagent evaporation reagent pack lid opener 430 does not open the secondary seal on other reagent packs 80, which are not required for that particular reagent aspiration process.

Reagent pack lid opener 430 preferably performs up to 3 or more lid open and close operations per test. In one example, based on 800 tests per day, 365 days per for 7 years, this equates to over 6,000,000 cycles.

Reagent pack lid opener 430 is designed to minimize the amount it encroaches on the reagent storage lid 412 insulation. In one example, a lid insulation thickness of approximately 15 mm assists in minimizing or preventing condensation forming on the outside of the lid when the instrument is operating at high end of the temperature and humidity range.

Reagent pack lid opener 430 optionally has a low profile to prevent clashing with the reagent transfer robot 60 during aspiration (e.g., see FIG. 25). The underside of the reagent transfer robot, at the bottom of its vertical travel in each of the four aspiration positions, defines the top of the operating space envelope.

Reagent pack lid opener 430 is aligned to reagent pack piercer mechanism using a hole and slot with 2 dowel pins. As the pack piercer 420 is aligned to the Reagent Carousel using a jig, the lid opener 430 mechanism inherits the same alignment.

To provide the maximum alignment tolerance between the reagent carousel 70 and lid opener mechanism 430, the design uses large diameter buttons 512 in the reagent carousel 70 and smaller actuation pins 500 in the lid opener. The lid opening buttons in the reagent carousel provide accurate alignment with the lid 470 hinge on each reagent pack 80 and a large target area for the actuation pins 500.

During the "open pack lid" action the reagent pack opener gearing 508, including a smaller gear 514 attached to stepper motor 510 and a larger gear that drives pin actuation arm 501, overdrives the vertical axis to ensure packs lids are always opened fully. Larger gear 512 in the vertical drive is spring 504 loaded to prevent steploss. This permits the stepper motor 510 to drive through the full range of movement regardless of where the carousel 70 is positioned, within the 2.0 mm vertical tolerance zone.

In one embodiment, no direct steploss detection is used on the reagent pack lid opener 430. In the case of steploss on either the horizontal or vertical axis during the lid opening process will, at worst, cause the reagent transfer robot 60 to steploss on its descent into the reagent pack 80. While the initial steploss is not detected, respective home optical sensors, e.g., vertical (rotational) home sensor 506 and horizontal home sensor 502, will sense that steploss has taken place on the vertical axis when actuation finger 501 is raised to close the pack lid; or on the horizontal axis when finger 501 prepares to open well 500a.

As shown in FIG. 32 reagent pack lid opener includes an actuation mechanism 499 attached to the top of the reagent storage lid 412 and actuation pins 500a-500d which are used to transfer the actuation force through lid 412 to the top of the reagent carousel 70. Actuation pins 500a-500d (generally termed actuation pin 500) are located to align with the reagent pack 80 lid above the aspiration points for each of, in this case, four reagent bottles. Lid opener 430 uses a finger 501 to depress the actuation pins 500a-d and utilizes a spring, e.g., 505d or similar mechanism for each pin 500 to return to the raised position. Finger 501 has a horizontal axis 503, which permits finger 501 to travel between the four actuation pins 500.

In one example of typical operation, the pack lid opener 430 is initialized during instrument startup. Approximately 3 seconds prior to a reagent aspiration, finger 501 is moved to position it above the required actuation pin, e.g., 500a. This action is called "Prepare to open pack lid". Just prior to a reagent aspiration, finger 501 is rotated down, the actuation pin 500a engages the reagent carousel 70 and the reagent pack lid 470 is opened. This action is called "Open pack lid". The reagent robot then lowers reagent probe 61 into the reagent pack 80, reagent is aspirated and reagent probe 61 is extracted. Finger 501 is rotated to a raised position and spring 505 force returns the actuation pin 500 to the raised position. This action is called "Close pack lid".

5.3.5.8 Typical Operation of Reagent Storage Assembly

FIG. 27 depicts a typical operation of reagent storage assembly 58. Briefly, the reagent storage 58 lifts the lid and raises the lifting platen 455 to the reagent carousel 70 installation position. Lifting platen 455 then rotates to present the desired reagent pack location to the user. The user installs either a new pack or replaces the entire reagent carousel 70. Reagent storage 58 lowers lifting platen 455 and closes the lid 412. Barcodes 472 are read to identify any new reagent packs 80.

Reagent storage 58 agitates the reagent pack for a period of time, e.g., four minutes, and reagent packs are ready for use. The reagent packs are periodically agitated to ensure uniform bead density throughout each bottle 82.

If the instrument 10 requires a specific reagent (in this case, from a new pack), the new reagent pack is rotated to a pack piercing position below pack piercer 420. Pack piercer 420 then moves down, opens the reagent pack lid, and breaks the primary seal on all of the reagent and conjugate bottles within the pack. Pack piercer 420 returns to the ready position allowing reagent pack lid 470 to close. Reagent pack 80 is rotated to the proper aspiration position (based on which reagent or conjugate bottle is to be aspirated from). Pack lid opener 430 opens the reagent pack lid 470. Reagent probe robot 60 aspirates the desired amount of reagent or conjugate. Pack lid opener 430 then closes the reagent pack lid 470.

5.3.5.9 Example Specifications of Reagent Storage Assembly components

The following TABLES 2-12 provide specifications for various reagent storage assembly 58 components described above. The specifications and values provided in the table are intended only as examples according to one embodiment, and are in no way limiting of the scope of the invention.

TABLE 2

Sample materials each of the reagent storage assembly gears

| Gear | Material |
|---|---|
| Sun gear | Acetyl |
| Planetary gear hub | Lubriloy D |
| Inner planetary gear | Polyurethane (95 shoreA) |
| Outer planetary gear | Nylon (6,6) |

TABLE 3 details the drive ratios for the agitation and turntable axes.

| Axis | Stepper Pulley (No. of teeth) | Secondary Pulley (No. of teeth) | Degrees per step | Steps per degree |
|---|---|---|---|---|
| Agitation | 24 | 192 | 0.225 | 4.4444 |
| Turntable | 24 | 192 | 0.225 | 4.4444 |

TABLE 4 details the drive ratios for the carousel lifter and agitation drive.

| Axis | Drive ratio |
|---|---|
| Lead screw pitch | 25 mm/rev |
| Agitation gear ratio | 212:28 |

TABLE 5

Suggested agitation parameters

| Agitation | Amplitude | Frequency | Period |
|---|---|---|---|
| New pack introduction | 450 degrees of rotation at the bead bottle | 1.5 Hz | 4 minutes on |
| Steady state running | 450 degrees of rotation at the bead bottle | 1.5 Hz | 3 seconds on 12 seconds off |

TABLE 6

Suggested nominal distances between hardware elements.

| Angular displacement | Default Angle |
|---|---|
| Carousel checking pin 1 - from lifting platen vertical home pin | 32 deg CW |
| Carousel checking pin 2 - from lifting platen vertical home pin | 122 deg CW |
| Carousel checking pin 3 - from lifting platen vertical home pin | 212 deg CW |
| Carousel checking pin 4 - from lifting platen vertical home pin | 302 deg CW |
| Agitation drive slot length | 144 deg |
| Lifting platen lowered (drive pins at end of drive slots) - Dog clutches disengaged | 300 deg ACW |
| Agitation drive pin centred in slot - Agitation drive pin at end of drive slot | 72 deg |

TABLE 6-continued

Suggested nominal distances between hardware elements.

| Angular displacement | Default Angle |
|---|---|
| Maximum lifter travel (rotational) | 1656 deg |
| Maximum lifter travel (distance) | mm |
| Stopping distance on proximity sensor - equivalent to 0.35 mm vertical | 5 deg |
| Back off distance for proximity sensor | 72 deg |
| Stopping distance on back off from proximity sensor | 10 deg |

TABLE 7

Suggested nominal drive currents for drive motors.

| Motor duty | Current |
|---|---|
| High hold current - used by turntable motor during agitation and carousel raise and lower | 1 amp |
| Low hold current - used by turntable and agitation motor while stationary | 0.5 amps |
| Agitation current - used by agitation motor during agitation | 6 amps |
| Move current - used by turntable and agitation motor during carousel rotation | 4 amps |
| Acceleration and deceleration current - used by turntable and agitation motor during carousel rotation | 6 amps |
| Lower carousel move current - used by agitation motor during carousel lower (the low current eliminates the danger of crushing users fingers) | 1 amp |
| Lower carousel acceleration and deceleration current - used by agitation motor during carousel lower (the low current eliminates the danger of crushing users fingers) | 1.5 amps |

TABLE 8

Suggested acceleration and velocities for the hardware elements.

| Parameter | Default Value |
|---|---|
| Disengage and engage dog clutch velocity | 45 deg/sec |
| Raise and lower lifting platen acceleration | 1000 deg/sec$^2$ |
| Raise and lower lifting platen velocity | 450 deg/sec |
| Vertical home velocity | 100 deg/sec |

TABLE 9

Suggested default soft set-ups for the turntable and agitation drive.

| Position - Relative to home Home = 154.1 clockwise from the front centre | Default Distance |
|---|---|
| Lifting Platen vertical home pin | 30.4 CW |
| Lifting platen lowered (drive pins at end of drive slots) - Lifting platen raised | 1440 deg CW |
| Pack 1 - Outer Bead Bottle Aspirate Position | 56.5 CCW |
| Pack 1 - Inner Bead Bottle Aspirate Position | 51.4 CCW |
| Pack 1 - Outer Conjugate Bottle Aspirate Position | 43.2 CCW |
| Pack 1 - Inner Conjugate Bottle Aspirate Position | 30.8 CCW |
| Pack 1 - Barcode 1 Read Position | 80.9 CW |
| Pack 1 - Barcode 2 Read Position | 80.9 CW |
| Pack 1 - Pierce Position | 115.9 CW |
| Pack 1 - User Access Position | 154.1 CCW |

TABLE 10

Suggested reagent bottle nominal positions

| Position | Distance from rotational axis |
|---|---|
| Well 1 (Outer bead bottle) | 148.45 mm |
| Well 2 (Inner bead bottle) | 120.15 mm |
| Well 3 (Outer conjugate bottle) | 100.45 mm |
| Well 4 (Inner conjugate bottle) | 87.55 mm |

TABLE 11

Suggested nominal vertical heights of the reagent storage elements

| Interfacing element | Distance above Base Support |
|---|---|
| Top of evaporator wall | 171 mm |
| Top of lid under reagent probe | 188 mm |
| Base of reagent bottles | 90.55 mm |
| Top of reagent bottles | |

TABLE 12

Suggested drive ratios for sample stepper motors.

| Axis - position | Drive pulley | Steps/mm | mm/Step |
|---|---|---|---|
| Lead screw | Lead screw 2 mm/rev | 100 | 0.01 |
| Piercer tips | ~7 times the lever ratio of the ball screw | 14 | 0.0714 |

5.3.6 Reagent Robot and Probe Assembly

FIGS. 33-35 show a reagent robot and probe assembly 60, also referred to simply as reagent robot 60 or reagent transfer assembly 60, according to an embodiment of the present invention. Reagent robot 60 generally includes a probe arm and head assembly 520 for mounting a reagent probe 61 similar to aspiration probe 370 described above, a rotational motor assembly 522, a vertical column and motor assembly 524, a base 526, a power in and rotational circuit board (PCB) 528, a vertical movement PCB 534, and a liquid level sense PCB 536. Reagent robot 60 accurately aspirates reagent and conjugate from reagent storage 58 and dispenses the reagent and/or conjugate into reaction vessels in incubator carousel 57. The reagent robot further provides liquid level sensing for use in tracking reagent usage. During use, the reagent robot moves to "stow" position when reagent storage assembly 58 is opened and pauses operation. Furthermore, reagent robot 60 cleans the reagent probe 61 in a wash station similar to aspiration wash station 90 to prevent any material carryover and/or contamination.

Probe 61 (shown with reagent robot 60 in FIG. 25) is threaded into probe head 521 (also termed probe mount 521). Reagent probe 61 transfers reagents from the reagent storage 58 to RVs on the incubator carousel 57. In the present embodiment, reagent probe includes the same features as, and is interchangeable with, specimen probe 370 described above with respect to FIGS. 22 and 23. For example, the tip of probe 61 has a reduced internal diameter to increase fluid dispense velocity and aid dispense accuracy. Top of probe 61 is preferably connected near probe mount 521 to a reagent syringe pump (e.g., a Cavro XP3000 syringe pump or the like) by a length of rigid walled PTFE or similar tubing filled with buffer fluid.

Probe arm and head assembly 520 includes probe mount 521, the connection to the reagent syringe pump and a probe blockage sensor, or pressure transducer. Arm 520 (and therefore, the probe) is adjusted horizontally by using the slotted screws 523 attaching arm 520 to the vertical column 525. As shown in FIG. 34, this adjustment provides the radial alignment required to align the probe for accurate movement between clean station 527, reagent storage 58 (e.g., four positions such as access ports 530a-d), and incubator carousel assembly 56 (e.g., two positions such as access ports 532a and 532b).

Head 521 provides a connection for the fluidics tubing and the liquid level sensing 536 to the reagent probe 61. Probe 61 is preferably threaded into the underside of head 521 with a small o-ring providing a seal. Head 521 provides adjustment of the probe in the z-angular direction relative to the probe head. The adjustment is in the x-y directions of the probe head only. Essentially, this moves the probe tip in either the x-y directions while the probe base (threaded into the probe head) is stationary.

A pressure transducer can be used to detect partial or complete blockages of the probe. The instrument monitors the pressure transducer for pressures outside the range of normal operation. Pressures outside of the normal operating range can be due to a number of factors. Error codes for each out of range pressure exist and assist with troubleshooting. The liquid level sensor 536, probe mount 521, reagent probe 61 and tubing are optionally interchangeable with those used on specimen handler assembly 66.

Rotational motor assembly 522 drives a belt and gear 527 to rotate vertical column 525 and thus reagent probe arm 520 through a fixed arc as shown in FIG. 34. Hard stops are located at the end of the travel arc. During normal operation, the travel arc is from incubator carousel assembly 56 middle ring, corresponding to port 532b, to the reagent carousel inner hole 530d. Clean station 527 is also included (approximately at the center) in the arc of motion.

The rotational home position of the probe preferably does not correspond to clean station 527 center. This design allows the reagent robot 60 clean position to be adjusted rotationally using motor assembly 522 to turn vertical column 525.

Vertical column and motor assembly 524 moves the reagent arm 520 and probe 61 in the vertical direction. The amount of travel is governed by different parameters for each specific location (e.g., incubator carousel 57, clean station 527, and reagent storage 58). The vertical travel at the incubator carousel 57 and clean station 527 is set to a fixed position determined during instrument alignment procedures. Liquid level sensor 536 determines the vertical travel at the reagent storage 58. Each parameter can be modified using a service program interface within the MAD host 40 software. The vertical movement is accomplished using motor 524 which employs a belt and gear system to move the top portion 538 of the vertical column 525 up and down. Additionally, a spring 529 is used to help hold column 538 in the up position when holding current is removed from the motor. Essentially, this prevents the probe from becoming damaged by collision with other parts when the instrument power is turned off.

Base 526 is mounted to the instrument SPM 30 chassis by two or more bolts, and provides a stable platform on which all other reagent robot 60 components are mounted. Base 526 also incorporates hard range of motion stops that physically prevent reagent robot 60 from moving outside the defined range of motion.

Example characteristics of vertical axis 524 and theta axis 522 stepper motors that may be employed in reagent robot 60 are shown in tables 13 and 14, respectively. In both examples below, stepper motors for the vertical 524 and theta 522 axis are attached to a pre-tensioned belt, which is attached to the vertical arm 525 of reagent robot 60.

TABLE 13

Example characteristics of a vertical axis stepper motor

| Feature | Number | Comment |
| --- | --- | --- |
| Resolution of stepper | 200 steps per turn | Full stepping |
| PCD of pulley | 11.2 mm | 14 tooth pinion |
| Resolution on the Axis | 0.17584 mm/step | |

TABLE 14

Example characteristics of a theta axis stepper motor

| Feature | Number | Comment |
| --- | --- | --- |
| Drive ratio | 5.714285714 | 14 tooth pinion and 80 tooth gear |
| Resolution of stepper | 1600 micro steps per rev | 200 step per turn with 8 micro steps per full step |
| Radius of point on Axis | 168 mm | Probe arm radius |
| Resolution on the Axis | 0.115395 mm | |
| Resolution on the Axis | 0.039375 degrees | 0.039375 |

5.3.6.1 Reagent Robot Circuit Boards and Sensors

Referring to FIG. 35, power in and rotational printed circuit board (PCB) 528 provides a single electrical connection to the instrument via backplane 200, operational power and sensing to horizontal, or rotational, motor 522, and operational voltages (drive & sensing voltages) to all other reagent robot 60 components. The input signals from the instrument are received via a large ribbon cable attached to the PCB. The operational power and sensing for the rotational motor 522 is distributed to the motor and optical sensor 540 by two wire connections to the PCB. The remaining operational voltages (for the rest of reagent robot 60 components) are transferred via a single cable to the vertical movement PCB 534. Rotational step optical sensor 540 determines the rotational position of the Reagent Robot and provides step loss monitoring. The sensor is located on the rotational drive motor assembly 522. A rotational home optical sensor (not separately shown) preferably determines the rotational home position of reagent robot 60. This sensor is located on the power in and rotational PCB 528. If replacement is required, the entire PCB is replaced. PCB 528 in this embodiment is located on a bracket that is directly mounted to base 526 as shown in FIG. 33.

Vertical movement PCB 534 provides power and sensing to the vertical motor 524 and power to the liquid level sense PCB 536. The operational power and sensing for vertical motor 524 is distributed to motor 524 and optical sensor 542 by two wire connections to PCB 534. Liquid level sense PCB 536 is connected via a ribbon cable. Vertical movement PCB 534 is mounted on the non-moving portion of vertical column 525. Vertical step optical sensor 542 determines the vertical position of reagent robot 60 and provides step loss monitoring. This sensor 542 is located on vertical drive motor assembly 524 and is connected to the vertical movement PCB 534. Vertical home optical sensor (not separately shown) is located on PCB 534 and determines the vertical home position of the robot 60. If replacement of this sensor is required, the entire PCB is replaced.

Liquid level sense PCB 536 uses capacitance sensing to determine when the probe comes into contact with a liquid. The instrument uses this information to determine the probe insertion depth into the reagent pack and reagent volume remaining within the bottle. Liquid level sense PCB 536 is mounted on the moving portion 538 of the vertical column 525. Additionally, a ground lug from the reagent storage assembly 58 is attached to the reagent robot to ensure proper operation of liquid level sensor 536.

5.3.6.2 Operation of Reagent Robot

In an example of typical operation of reagent robot 60, probe 61 is cleaned at the clean station 527. Reagent robot 60 returns to the ready position over clean station 527. Reagent robot 60 then rotates probe 61 over a specific well, e.g., port 530a, in reagent storage 58. Reagent robot 60 then lowers the probe into the reagent pack and aspirates a specific volume of reagent. After aspiration, reagent robot 60 lifts the probe above the reagent storage assembly 58 and rotates over the incubator carousel 57. Once over the proper location of incubator carousel 57, robot 60 lowers probe 61 into a hole, e.g., 532a, in the incubator carousel 57 lid. Reagent robot 60 then dispenses the reagent into an RV on the incubator carousel 57. After dispensing reagent, the reagent robot 60 raises the probe from incubator carousel 57 and rotates probe 61 to the center of the clean station 527. Finally, reagent robot lowers probe 61 into the clean station 527 for cleaning

5.3.7 Incubator and Separation Carousel Assembly
5.3.7.1 Overview of Incubator and Separation Carousel Assembly FIGS. 36-42 depict the structure and function of an incubator and separation carousel assembly 56 (also generally referred to herein as "incubator carousel assembly" 56) according to an embodiment of the present invention. Referring to FIG. 36, the incubator and separation carousel assembly 56 is designed to incubate the reaction vessels at predetermined temperatures. Preferably, assembly 56 incubates specimens at not less than about 34° C. and not more than about 39° C. with a stability of about ±0.5° C. over an interval of about 45 minutes. The assembly 56 also agitates the reaction vessel during incubation at defined intervals for approximately about forty percent of the incubation period. Preferably, the agitation frequency is about 22 Hertz with an amplitude (peak to peak) of about six millimeters for about three seconds. Of course, other incubation and/or agitation parameters may appropriate for a given assay and be used without departing from the scope of this invention. The outer separation carousel 55 portion of incubator carousel assembly 56 also magnetically holds the beads (described below) in reaction vessels when liquid contained in the reaction vessel is aspirated. Preferably, each reaction vessel located on separation carousel 55 is associated with two magnets, positioned to maximize bead retention as described in more detail below. Incubator and separation carousel 56 also moves the reaction vessels to defined positions for aspiration, dispense, and movement. It is preferred that the time required to move any reaction vessel to another location is less than about 0.5 sec.

Incubator and separation carousel assembly 56 interfaces with other sub-modules and components of system 10, e.g., as shown below in TABLE 15.

TABLE 15

Incubator And Separation Carousel Assembly Interactions*

| Incubator Carousel interfaces with; | Separation Carousel interfaces with |
|---|---|
| RV Handler 52a | RV Handler 52a |
| RV Handler 52b | RV Handler 52b |
| Reagent Transfer Robot | Wash Aspiration Probes |
| Specimen Transfer Robot | Wash Dispense Probe |

*Both Carousels interface with RV Handler 1 and RV Handler 2, however they typically do so in different locations.

Referring to FIG. 36 the incubator and separation carousel assembly 56 has a number of components, including, e.g., an incubator lid 550, an inner incubator carousel 57, an outer separation carousel 55, a separation carousel drive 552, an incubator carousel drive 554, a tub-incubator chamber 556, 558, and a fan and heater assembly 560, 561. Typically, all of the components are mounted on or attached, directly or indirectly, to a main support casting 562, that is attached to the main instrument 10 chassis.

Incubator lid 550 is insulated to maximize thermal performance and to minimize heat loss. A single large knurled nut 551, located in the lid center, is used for removal and replacement of lid 550. Holes in lid 551 allow the RV handlers (e.g. holes 554), reagent transfer robot 60, wash robot 62, and specimen aspirate robot 66 to access RVs located on either incubator carousel 57 or separation carousel 55.

5.3.7.2 Incubator Carousel

Incubator carousel 57 holds a large number, e.g., 100, RVs within two outer rings 57a, 57b of forty RV receptacles each and one inner ring 57c of twenty RVs. Outer two rings 57a,b are used for incubating samples while the inner ring 57c is used as RV storage only when "temporary" situations occur. For example, a temporary storage occurs when instrument 10 is unable to process the RVs to either the detector 20 or the waste 64.

Incubator carousel 57 is agitated at a frequency of, e.g., 22 Hertz with an 6 millimeter amplitude (peak to peak) for approximately 3 seconds. Samples are agitated for approximately 29% of the time spent on incubator carousel 57. Other incubation parameters may be used.

TABLE 3 provides and example of which incubator carousel rings interface with the various other components of the instrument.

TABLE 16

Incubator Carousel Ring Interfaces

| Interfacing device | Outer ring 57a | Middle ring 57b | Inner ring 57c |
|---|---|---|---|
| RV Handler 52a | Yes | Yes | Yes |
| RV Handler 52b | Yes | Yes | No |
| Specimen transfer robot | Yes | No | No |
| Reagent transfer robot | Yes | Yes | No |

Referring to the block diagram of FIG. 37, temperature sensors 570 and 572 are utilized to monitor the temperature of the incubator carousel 57. The incubator chamber interior temperature and the ambient incubator chamber 556 housing temperature are monitored using dual thermistor assemblies 570, 572 respectively, to provide redundancy. The thermistor assemblies 570, 572 are connected to the temperature sensor PCB, mounted inside the incubation chamber 556, which is covered to prevent fluid spills from damaging the circuit. The temperature sensor PCB 574 is mounted to provide cable connection access from the outside of the incubator tub.

5.3.7.3 Separation Carousel

Separation carousel 55 holds approximately 40 RVs in a single outer ring on an independently driven carousel (e.g., driven by motor assembly 552). Separation carousel 55 runs concentrically around the outside of incubator carousel 57. Separation carousel 55 has several characteristics differentiating it from the incubator carousel 57. For example, one differentiating characteristic is a number of magnets 580 (with backing plates 582) installed in the inner portion of the separation carousel 55 as shown in FIG. 38. Magnets 580 hold the microspheres in the RV (which is held in RV receptacle 584) while wash buffer is added and removed as described above with respect to FIG. 8. Backing plates 582 provide a secure base for the magnets as well as containing the magnetic field to separation carousel 55.

Additionally, due to the high magnetic strength used, separation carousel 55 optionally has a steel magnetic shield 586 installed between the separation carousel and the incubator carousel. Magnetic shield 586 prevents stray magnetic field from interfering with the chemistries occurring on the incubator carousel 57.

The magnetic separation process is used to allow removal of spent sample and reagent following incubation as well as washing of the beads to remove non-specifically bound sample and conjugate reagent. When a RV is placed into separation carousel 55 magnets 582 attract the beads into a patch on the inner wall of the RV. After a separation period of 30-90 seconds, more preferably 55-65 seconds (dependent on scheduler and timing) the carousel moves the RV under the wash aspirate probes. The probes are driven to the bottom of the RV where they aspirate all the remaining fluid out of the RV without aspirating any of the beads. The attraction of the beads to separation magnets 282 forces the bead patch to remain held to the RV wall. Once all the excess fluid has been removed the aspiration probes are retracted from the RV. Separation carousel 55 positions the RV under the wash dispense probe where wash buffer is dispensed into the RV. The wash buffer flows over the bead patch and removes non-specifically bound analyte and conjugate reagent. The separation and wash process is repeated a number of times as specified by the chemistry protocol.

TABLE 17 suggests which instrument components typically interface with separation carousel 55.

TABLE 17

Separation Carousel Interfaces

| Interfacing device | Separation Carousel |
|---|---|
| RV Handler 52a | Yes |
| RV Handler 52b | Yes |
| Wash Aspirate Probes | Yes |
| Wash Dispense Probe | Yes |
| Specimen transfer robot | No |
| Reagent transfer robot | No |

5.3.7.4 Separation Carousel Drive

Referring to FIG. 39, separation carousel drive 552 contains a servo-motor 552a, a pulley 590a, an encoder ring 592, tensioning spring 596 and a timing belt 594. All these components work together to move separation carousel 55 to locations required by the host 40 software to complete various tasks (e.g., RV movement, wash buffer dispense or aspiration).

Servomotor 552a, which is commonly used in reagent storage drives, is well suited to its role of slewing separation carousel 55 back and forth. Pulley 590a is sized to maintain proper meshing with timing belt 594. The pulleys 590a and 590b on the separation carousel 55 and incubator carousel 57 are preferably similar.

Encoder ring 592a, which is mounted on pulley 59a, allows the sensor to determine the position of the separation carousel 55.

Tensioning spring 596 maintains a specific tension on timing belt 594 throughout its operational lifetime. This reduces vibration, noise and eliminates problems associated with belt wear. Tensioning spring 596 is mounted to the motor mounting 598 and the instrument chassis. Timing belts 594a, 594b, which are preferably the same or similar for both separation and incubator carousel, is preferably although not necessarily a KEVLAR reinforced polyeruthane continuous timing belt.

A separation carousel rotational step optical sensor determines the rotational position of the outer carousel 55. The sensor is located in the incubator carousel housing 556 on the rotational gear, while the optical flags are located on the bottom of the rotational gear. The optical sensors use quadrature encoders to determine and monitor the position of the carousels. The following describes the operation of the sensors with quadrature encoders.

Quadrature encoders associated with quadrature optical sensor circuit board 576 of FIG. 37 provide feedback to the control software for the carousel drives 552, 554. The quadrature encoders sense the encoder ring 592a, 592b on each of the carousel pulleys, providing feedback from the carousel side of the drive system and detecting belt breakage or slippage.

Each carousel 55, 57 has its home position identified by one slot on the step loss detection castellated ring 592a, 592b, which is 150% larger than the other slots. The home position is found by rotating the carousel until both sides of the slot have been detected. The carousel is then driven back to the center of the slot and is considered homed.

Both of the carousel motor drives 552, 554 in the assembly 56 use a quadrature encoder for position feedback. Two techniques are used to monitor the drive positions during rotations and while static.

The basic feedback is provided by an optical quadrature encoder positioned under a slotted ring 592a, 592b that is incorporated into the web of the large drive pulleys 590a, 590b on each of the carousel drives. The encoder produces two slightly out of phase signals. The rotational direction of a slot passing between the sensor's detector and emitter is determined by the order in which the sensor signals change state.

The first technique used for tracking the carousel positions uses a high-speed counter to track the total number of slots passed. Slots detected in clockwise direction are added to the total count while slots detected in counter-clockwise direction are subtracted from the total. Due to the speed of the counter the cumulative slot count is capable of tracking slots during fast moves and agitation even where mechanical vibration causes effects similar to switch bounce. The counter output is predominantly used after a carousel move or after agitation to check that the carousels are in the correct position prior to interfacing with another device.

The second technique used for position tracking is used to detect loss of position control during moves and agitation. When an error or collision is detected the drive current to the motor is instantly removed in an effort to minimise the possibility of damaging the carousel or the object it has collided with. During a move or agitation the control software calculates the exact time when the encoder will be in the middle of either a slot or the adjoining rib. The software then checks at each calculated time to compare the sensor state to the predicted state. If a discrepancy is detected a position error is reported.

5.3.7.5 Incubator Carousel Drive

Incubator carousel drive 554 is essentially the same or similar to the separation carousel drive 552 except for the motor and bearing. While the separation carousel drive does not use a bearing, the constant agitation of the incubator carousel 57 benefits from the use of a bearing to provide impact and vibration cushioning. The demands on the incubator carousel motor, slew and agitation, suggest that this motor preferably is more durable and reliable than the motor used in the separation carousel. Additionally, the bearing chosen provides both impact and vibration cushioning and prevention of bearing failure due to localized welding and consequent pitting.

Incubator carousel rotational step optical sensor determines the rotational position of the Incubator. The sensor is located in the incubator carousel housing underneath the rotational gear.

5.3.7.6 Tub—Incubator Chamber

Incubator chamber 556, 558 is preferably fabricated from structural polyurethane foam to provide good thermal insulation. The thermal insulation is beneficial to prevent heat flow into the rest of the instrument and to provide a constant air temperature throughout the incubator. The incubator chamber minimizes the heat loss by insulating the casting, minimizing air leakage through the timing belt slots and providing a cover for the wash aspirate and dispense probes. Incubator chamber 556, 558 also provides an overflow drain to prevent any liquid from reaching heater 561.

Additionally, mounts for the reagent transfer robot and specimen transfer robot clean stations are preferably located on the incubator chamber.

5.3.7.7 Fan and Heater

The incubator assembly 56 is heated to provide an optimised stable environment for the assay chemistry. A predefined warm-up time for the incubator is preferable because the incubator is generally only constantly heated during assay chemistry.

To avoid adding mass to incubator carousel 57 an air heating element 561 and fan 561 are beneficial to control temperature inside the incubator. Heater 561 and fan 560 are preferably automatically configured to permit either 110/240 volt compatibility when the instrument is configured to the source voltage.

A single use thermal fuse protects the heater element from any over-temperature conditions that may occur. The nominal trip temperature for the thermal fuses is 70° C. (~184° F.). Software will typically flag any thermal fuse trips or defective heater as a temperature out of range condition.

Fan 560 is preferably equipped with a tacho output to enable detection of fan failure or error. Fan and heater assembly 560, 561 is removed from the bottom of the incubator and separation carousel assembly 56 without requiring the accessing of either carousel.

Fan 560 circulates the heated air around below the incubation carousel. Dual thermistors monitor the air temperature 570 and provide feedback to the heater control circuitry 561a, 561b. The air thermistors are mounted on the metal housing surrounding the drive mechanisms.

5.3.7.8 Operation of Incubator and Separation Carousel Assembly

According to one embodiment, typical operation of incubator and separation carousel assembly 56 is as follows. An RV is removed from the RV supply 262 and delivered to incubator carousel 57 outer ring 57a by RV Handler 52a. Incubator carousel 57 rotates the RV to the reagent dispense position where reagent is added. Incubator carousel then rotates the RV to the sample dispense position where sample is added. Incubator Carousel 57 then agitates and incubates the RV.

After agitation and incubation of the sample in the RV, incubator carousel 57 rotates the RV to a RV pickup position where the RV is removed from the incubator carousel placed on separation carousel 55 by RV Handler 52b. The separation carousel rotates the RV to the wash aspirate probe position where the wash probe robot removes the liquid. Separation carousel 55 rotates the RV to the wash dispense position where liquid is added to the RV.

After washing, separation carousel 55 rotates the RV to a RV pickup position where the RV is removed from the separation carousel and placed in the incubator carousel 57 middle ring by RV Handler 52b. If required, the incubator carousel will also rotate the RV to accommodate any the addition of any other reagents. Incubator carousel 57 holds and agitates the RV until the incubation time is completed. Incubator carousel 57 then rotates the RV to a RV pickup position where the RV is removed by RV Handler 52a and delivered to detector robot 74.

5.3.8 Wash Station Robot

Referring to FIGS. 40-41, according to one embodiment, a wash robot 62 includes a wash probe head and column assembly 610 a clean station, and a wash dispense probe 620. Wash robot 600 aspirates waste fluids from reaction vessels while the separation carousel 55 holds the beads, by magnetic force, within the reaction vessels. The wash robot provides a uniform aspiration of liquid when aspirating from between one to four reaction vessels. The wash robot cleans all wash aspiration probes after use. Angled tip probes 612 are preferred to minimize probe blockage, however, blockage detection sensors are used to detect blockage of any wash aspiration probe. The wash system also provides the wash buffer for washing and re-suspending the beads.

Wash probe head and column assembly 610 move the wash probes vertically to the following positions: an RV aspirate position, a probe cleaning position and a ready position. Wash probe head 614, to which one or more probes 612 are installed (e.g., two, four or more probes 612), is mounted on the top of the column 616. Column 616 is driven vertically using a stepper motor 618 and belt drive.

Wash robot 62 includes sensors home position and steploss. For example, a wash probe vertical home optical sensor 622 (see FIG. 41) determines the vertical home position of the wash probe head and column. This sensor is located on top of the wash robot housing. A wash probe rotational steploss optical sensor, optionally determines if steploss during the vertical movement of the wash probes 612 has occurred. An encoder wheel can be is mounted on the stepper motor 618. Horizontal wash motor 630 and wash well are also optionally used. Motors 618, 630 and sensors, with as sensor 622 and 632 preferably communicate with system 10 through circuit board 634 and backplane 200.

The clean station 62 is mounted on a tilting axis, which moves between a cleaning position and a retracted position. In the cleaning position, the clean station is rotated into the path of probes 612. In the retracted position, the clean station is rotated out of the probe path.

A clean station home optical sensor optionally determines the tilt home position of the clean station. In one embodiment, a clean station home optical sensor is located on the rear of the wash probe housing and is tripped by a flag rotating on the stepper motor.

A wash probe blockage sensor optionally determines if a wash probe 612 is blocked. Such a wash probe blockage sensor is preferably a conductive type sensor with one end mounted in the clean station and the other on the wash probes 612. If liquid remains in the clean station after cleaning, then the wash probes 612 did not perform the clean aspiration properly.

Wash dispense probe 620 is mounted on the right side of wash robot 600. The Wash dispense probe 620 dispenses a measured amount of wash fluid into the RVs located on the separation carousel. A FMI micropump, located in the fluidics subsystem as described below, provides the wash fluid through a fluid line 636. Wash dispense probe 620 is mounted on a retractable lever arm 624, which allows the probe to be rotated out of the way for service intervention.

During typical operation of the wash robot 600 RV handler 52b removes an RV from incubator carousel 57 and places it on the separation carousel 55. RV contains a mixture of sample, reagent and conjugate depending on how far the assay has progressed. Separation carousel 55 moves the RV under one of the four wash probes 612 (after a predetermined separation time to allow the magnets to collect the beads against the RV wall). Wash robot (in the ready state with its clean station retracted) then lowers the wash probes into the RV to remove the liquid. Liquid is aspirated from the RV through the wash probe, e.g., by a nominal 15 kPA vacuum. After aspirating fluid from the RV, wash robot 600 then raises the wash probes and clean station tilts forward under the wash probes. The Wash robot lowers the wash probes into the clean station and DI water fills the clean station. The liquid is aspirated from the clean station by a nominal 30 kPA vacuum. Wash robot then raises the wash probes and the clean station retracts. Next, the separation carousel moves the RV under the wash dispense probe, where wash dispense probe dispenses a measured amount of wash buffer into the RV. The amount of wash buffer depends on the type of assay being performed and the progress of the RV in the assay.

After a predetermined separation time to allow the magnets to collect the beads against the RV wall, the separation carousel then moves the RV under one of the four wash aspirate probes. The RV is again presented to the wash probes and the wash probe liquid aspiration is repeated. Depending on the type of chemistry being performed the washing of the beads can occur a number of times.

After the last wash, the RV is presented to the wash dispense probe and a resuspend volume of liquid is dispensed into the RV. Separation Carousel 55 moves the RV to the RV Handler 52b pickup position. RV Handler 53b then removes the RV from the separation carousel 55 and places it on the incubator carousel 57.

5.3.9 Detector Transfer Robot Assembly

FIG. 42 shows a detector transfer robot 74, or detector robot 74, according to an embodiment of the present invention. Detector robot 74 generally includes a reaction vessel rotational arm and drive 650, a waste disposal lever 652, a clean station and drive 654, and a detector module probe mount 656. Detector robot 74 presents reaction vessels to a detector module probe (also termed "detector probe", not shown) on mount 656 and disposes of the reaction vessels after sample aspiration. Detector robot 74 also cleans the detector probe between each use and provides a stable mounting platform for mounting the detector probe.

RV rotation arm and drive 650 moves an RV from the "putdown" position (e.g., by RV Handler 52a on incubator carousel 57) and presents it to the detector module probe for aspiration. A drive motor 658 attached to a lead screw 660 rotates and moves the arm vertically. The vertical movement is accomplished by rotating the arm until it hits a hard stop (in this case, the vertical structure, or vertical stainless steel rod 662), of detector robot 74, then the lead screw 660 continues to turn, driving arm 664 vertically (either up or down).

Referring to FIG. 43, the following sensors monitor the position and movement of the RV rotational arm and drive 650. A detector robot rotational home optical sensor 666 located on detector robot 74 housing is designed to determine the rotational and vertical home position of the detector robot 74. A detector robot rotation step optical sensor 668 determines the rotational position of detector robot 74. This sensor is located on the rotational gearing above motor 658. Vertical positioning of the arm 664 is controlled by parameters set within the software. Vertical alignment is performed during instrument installation. After the initial alignment, modification of the alignment is only required when the distance between the detector module probe tip and the RV bottom exceeds 1.0 mm. An optimum distance is between 0.5-1 mm.

Referring again to FIG. 42, downward arm 664 motion at the pickup position triggers the action of the waste disposal lever 652. When the arm moves down waste disposal lever pushes the RV out of the rotational arm 664 and into the waste chute 670. Waste disposal lever 562 includes a prong and lever. The prong is used to push the RV up and out of the rotational arm 664 and the lever pushes the RV over into the waste chute 670.

Clean station and drive 654 raises and lowers the clean station 672 to the detector module probe. Clean station and drive 654 also uses a drive motor 674 and lead screw 676 to vertically move clean station 672. All the fluidics connections to the clean station are located on the bottom of the clean station. This allows the clean station to move freely up and down without tangling the fluidics tubing. Clean station 672 has multiple fluid lines, e.g., one input fluid line (for cleaning the outside of the probe) and two output fluid lines (one for draining the clean station and one as an overflow).

Referring back to FIG. 43, the following sensors monitor the status, position and movement of the clean station and drive 654. Clean station home optical sensor 678, located on detector robot 74 housing, determines the vertical home position of clean station 672. Clean station vertical optical sensor 680, located on the rotational gearing associated with motor 674 used to move clean station 672, determines the vertical position of the clean station. Additionally, a clean station overflow sensor is a conductive sensor mounted on or within clean station 672 to monitor clean station for any blockage that would cause clean station 672 to overfill.

The detector module probe mount 656 secures the detector probe to the top of detector robot 74. Detector Module probe is placed through the top of the mount 656 and secured using the threaded nut. The mounting position is adjustable by a slot and screw combination. The probe has holes, for example five holes of approximately 0.005 inch, or about 0.0127 mm, running through it and contains an internal screen.

During typical operation of detector robot 74, rotational arm 664 moves to an RV acceptance position and RV Handler 52a places a RV in the RV holder 665 of rotational arm 664. Rotational arm 664 rotates clockwise to below the detector module probe and raises the RV to the aspiration position for the Detector Module probe in probe mount 656 as shown in FIG. 42. Detector module probe aspirates the sample from the RV. After aspiration, rotational arm 664 lowers and rotates back to the pickup position. Rotational arm 664 then lowers causing the waste disposal prong to push the RV out of the rotational arm. Lowering the rotational arm activates spring loaded waste disposal lever 452 and the lever moves forward and pushes the RV into the waste chute 670. Next, clean station 672 rises to clean the detector module probe and rotational arm 664 returns to the RV acceptance position. Clean station 672 lowers after cleaning the probe.

While detector transfer robot assembly 74 is described above as being an assembly within sample processing module 30, robot assembly 74 may be part of or incorporated within detector module 20.

5.3.10 RV Waste Assembly

FIGS. 44A and 44B show a reaction vessel waste assembly 700 according to an embodiment of the present invention. Reaction vessel waste assembly 700 generally includes a reaction waste chute 670 (as described with respect to FIG. 42), a reaction vessel buffer area 702, a reaction vessel waste bin, and a reaction vessel waste level tracker. Reaction vessel waste system 700 preferably has quantity to accept waste from up to eight continuous hours of operation. A user of the device can remove and empty the waste bin 706 without interrupting the operation of the device. Reaction vessel waste bin 704, e.g., located in solid waste compartment 64 of device 10 (see FIG. 2) is easily accessible and fitted with biohazard bags for the collection of waste. The components of the reaction vessel waste system are accessible for easy cleaning. Furthermore, there is a monitoring system that monitors the waste system and determines the presence of a biohazard waste bag and monitors the level of waste, alerting the user when the waste requires emptying.

RV waste chute 670 is designed to catch the RVs dumped by the detector robot 74 as described above. A wide, sloping design (e.g., 30 degrees or more on all surfaces) ensures all RVs and liquid (contained within the RVs) are directed into the RV waste bin 704. RV and liquid are not allowed to block or pool in chute 670. Since the RV waste chute 670 will be interacting with waste (both RVs and their liquid), periodic cleaning of the chute is recommended. Chute is easily removed and cleaned by detaching it from its interface 708 with RV buffer area 702. In this embodiment, lower end of chute 760 fits within an opening 710 on upper end of RV buffer 702.

RV buffer 702 is designed to catch and hold RVs and their liquid waste whenever the RV waste bin 704 is extended or pulled out of the instrument chassis for waste removal. RV buffer 702 includes a main body 703 that interfaces with RV waste chute 670, and a trap door 712. Trap door 712 is located towards the bottom end of RV waste chute 760 and is hingeably attached at two connection points 714 to body 703 such that door 712 can move from a closed (i.e., blocking the passage of RVs and fluid to waste bin 704) to an open position as shown. One skilled in the art will recognize that other door or door attachment mechanisms may be used without departing from the scope of this invention.

In this embodiment, RV buffer 702 has the capacity to store approximately 1 hour worth of RV and liquid waste (e.g., approximately 100 RVs and approximately 2 ml of fluid). RV waste bin 704 holds trap door 712 in the open position as shown under normal operation. However, when RV waste bin 704 is extended (opened) for waste removal, trap door 714 moves to the closed position blocking passage of disposed RVs. RV buffer 702 preferably does not use any motors to move into position, rather door 712 moves between open and closed positions by either gravity or contact with waste bin 704. Optionally, a buffer door latch or stop 716 limits forward travel of door 712 when in closed position. In other embodiments, buffer 702 employs spring mechanisms or the like to control door position.

RV buffer 702 preferably includes an optical sensor located in the waste chute or RV buffer area 702 to determine if trap door 712 is in an open or closed state, and to communicate the state to the user through the host PC 40 or some other indicator such as a visual (e.g., LED indicator) or audio indicator.

RV waste bin 704 is a pullout drawer, incorporating a handle 706 and slides 718, capable of extending beyond the instrument footprint and is preferably is configured to accept standard biohazard bags, e.g., bags measuring approximately 14"×19". A biohazard bag is secured within the RV waste bin 704, for example by spring clips, to prevent the bag from tearing when the bin is opened or closed. A bag detection sensor monitors the presence of the bag. In one embodiment, bag detection sensors are a conductive spring loaded contact switch system that is opened by the presence of any plastic biohazard bag. Removal of the bag trips the conductive sensor, causing software in host PC to determine no bag is present. In such embodiment, bag detection sensors are two-wire connections to a moving cable attached to the RV waste drawer.

Computer software, e.g., in host 40, also monitors RV waste bin 704 level by incrementing the number of RVs in the waste each time a RV is transferred to waste 700 by detector robot 74. The level is reset to zero every time a bag change is detected. To provide accurate tracking of waste level, the bag detection sensors are activated as a background task during power up and continue until the instrument is powered down. The sensors are required to remain active when RV waste bin 704 is extended out on the drawer slides 718, as this is the time when the user will remove the waste bag. The sensor cable, to allow the drawer, is coiled to prevent tangling when the drawer is open or closed.

5.3.11 Cleaning Station Design

Three types of clean stations are used. All cleaning stations are designed to effectively clean the probe (inside and out) and minimize the consumables 12 used.

The Specimen and Reagent Probe Clean Stations are two-stage type clean stations. First, all contaminated waste is disposed of directly down the waste tubing cleans the probe. Then, the probe moves over and down into a well where liquid from the probe cleans interior and exterior of the probe.

The Detector transfer probe clean station is similar to the Specimen Probe and Reagent Probe Clean station except the Clean Station is a single stage type clean. The probe interior and exterior is cleaned by wash liquid supplied by the probe, however the probe is not moved from a dirty waste disposal position to a clean probe position. The detector probe clean station is aligned physically in the x-y axis using slots in the clean station. The probe insertion depth is a software controlled variable.

The Wash Probe Clean Stations clean the probes by filling the clean station with wash liquid, then using the probes to drain the stations. In these stations, only a wash liquid supply is required. The liquid is drained only via the probes. The initial wash liquid supply cleans the outside of the probe and the draining via the probes cleans the interior. The probes are aligned physically in the horizontal axis (combination of x-y axes) using slots in the clean stations for positioning. The rotational alignment and probe insertion depth are software-controlled variables.

5.3.12 System Fluidics 5.3.12.1 Overview of System Fluidics

FIGS. 45-48 show a fluidics system 800 according to an embodiment of the present invention. FIG. 45 shows a number of fluid and waste storage bottles, including buffer supply 802, sheath supply 804, DI water 806, and waste 808. Fluidics system 800 generally supplies buffers, including sheath, wash, and deionized water for use in detection, cleaning, and sample movement. For example, the system provides for the addition of liquids and disposal of waste without interruption of operation. Furthermore, the system also accurately aspirates and dispenses samples and reagents of various quantities. Additionally, the system accurately dispenses and aspirates wash buffer from reaction vessels, cleans the outside of all probes, and cleans the inside of all reagent and specimen probes. FIGS. 45 and 46A and 46B are a block diagram and a detailed schematic diagram, respectively showing fluidics system 800 and the various related components and sensors described herein, many of which preferably, although not necessarily receive power from and communicate through fluidics circuit board 810.

Internal bulk reagent and waste reservoirs as shown if FIG. 45 contain enough capacity on board the device to allow all specimens currently in a process to be completed, should external supplies be exhausted.

Fluidics control system provides a wash buffer, sheath fluid for the detector and deionized water for cleaning probes. The fluidics control system incorporates at least three precision syringe pumps for specimen and reagent aspiration and dispense, and an FMI positive displacement dispensing pump for bead washing.

In one embodiment, the fluidics system includes a number of sub-subsystems, each of which are discussed in more detail below.

5.3.12.2 Details of Subsystems of System Fluidics

DI Water Subsystem #1

The DI Water Subsystem stores and delivers DI water to the other sub-systems. DI water is used to clean various probes, flush valves and components and perform periodic maintenance. Additionally, as an added option DI Water Subsystem can be directly plumbed into the instrument.

The DI Water Subsystem includes a Bulk DI Water Supply (e.g., 5 Liter Capacity), a customer accessible container with liquid level monitoring. The Bulk DI Water Supply has the capacity to supply the instrument with DI for an eight-hour continuous run. The liquid level sensing is used to notify the customer, via a software interface, when additional DI is required. This container is not pressurized or under a vacuum.

A DI Water Intake Pump pumps DI from the Bulk DI Water Supply to the Internal DI Water Supply. The pump is activated when the DI level in the Internal DI Water Supply falls below a specific level. A self-priming diaphragm pump is used in this capacity.

A DI Water Intake Check Valve prevents DI water from traveling from the Internal DI Water Supply to the Bulk DI Water Supply. The check valve (1.5 psi cracking pressure) is required because the Internal DI Water Supply bottle is pressurized.

An internal DI Water Supply such as a 1 Liter Capacity pressurized internal DI reservoir with liquid level monitoring. The low pressure provides the motive force to drive the DI water to the various pumps and clean station. The Internal DI Water Supply capacity is maintained to provide for the completion of all in-process assays should the Bulk DI Water Supply be exhausted or removed. A current minimum is 550 ml. An example of a DI water supply 850 is shown in FIG. 48B.

DI Selector Valve—Provides either DI water or Wash Buffer to the Fluid Supply Manifold depending on the valve position.

Fluid Supply Manifold—Provides either DI water or Wash Buffer to the various pumps and clean stations contained within the other sub-systems. The DI Selector Valve controls the supply of fluids (either DI or Wash Buffer) to the Fluid Supply Manifold.

Tubing and Fittings—Various small diameter tubing and fittings used to connect the components.

The DI Water Supply preferably has a number of sensors, for example six sensors. A thermistor type sensor is used in all DI Water sensing situations due to the non-conductive nature of DI Water. Thermistors are semiconductors that will change resistance with a change in temperature. As the DI Water covers or uncovers the thermistor, the resistance of the thermistor changes. In both the Bulk and Internal DI Water, three thermistors are used to correctly sense DI Water liquid levels.

Bulk DI Water Supply Cap Sensor—Monitors the ambient temperature and provides a reference point for the software to identify changes in liquid levels at the low and high liquid level sensors.

Bulk DI Water Supply Low Liquid Level Sensor—Monitors the low liquid level within the Bulk DI Water Supply. When tripped, this sensor causes the software interface to notify the customer that additional Bulk DI Water is required.

Bulk DI Water Supply High Liquid Level Sensor—Monitors the high liquid level within the Bulk DI Water Supply. When tripped, this sensor causes the software interface to notify the customer that Bulk DI Water is full.

Internal DI Water Supply Cap 826 Sensor—Monitors the ambient temperature and provides a reference point for the software to identify changes in liquid levels at the low and high liquid level sensors.

Internal DI Water Reservoir Low Liquid Level Sensor 822—Monitors the low liquid level within the Internal DI Water Reservoir. When tripped, this sensor causes the Internal DI Reservoir to be filled from the Bulk DI Water Supply via the DI Intake pump (provided bulk DI water is present).

Internal DI Water Reservoir High Liquid Level Sensor 824—Monitors the high liquid level within the Internal DI Water Reservoir. When tripped, this sensor stops the filling of the Internal DI Reservoir.

Wash Buffer Subsystem #2

The Wash Buffer Subsystem stores and delivers Wash Buffer to the other sub-systems. Wash Buffer is used as a hydraulic fluid, bead washing and re-suspension, probe cleaning fluid and specimen diluent. The Wash Buffer Subsystem includes the following components.

A Bulk Wash Buffer Supply—10 Liter Capacity—A customer accessible container with liquid level monitoring. The Bulk Wash Buffer Supply has the capacity to supply the instrument with Wash Buffer for an eight-hour continuous run. The liquid level sensing is used to notify the customer, via a software interface, when additional Wash Buffer is required. This container is not pressurized or under a vacuum.

A Wash Buffer Intake Pump—Pumps Wash from the Bulk Wash Buffer Supply to the Internal Wash Buffer Supply. The pump is activated when the Wash Buffer in the Internal Wash Buffer Supply falls below a specific level. A self-priming diaphragm pump is used in this capacity.

A Wash Buffer Intake Check Valve—Prevents Wash Buffer from traveling from the Internal Wash Buffer Supply to the Bulk Wash Buffer Supply. The check valve (1.5 psi cracking pressure) is required because the Internal Wash Buffer Supply bottle is pressurized.

An Internal Wash Buffer Supply—1 Liter Capacity—A pressurized internal Wash Buffer reservoir with liquid level monitoring. The pressure provides the motive force to drive the Wash Buffer to the various pumps and clean station. The Internal Wash Buffer Supply capacity is always maintained to provide for the completion of all in-process assays should the Bulk Wash Buffer Supply be exhausted or removed. An example of a current minimum is 550 ml, as shown in the example internal wash buffer supply 830 of FIG. 48A.

A DI Selector Valve—Provides either DI water or Wash Buffer to the Fluid Supply Manifold depending on the valve position.

A Fluid Supply Manifold—Provides either DI water or Wash Buffer to the various pumps and clean stations contained within the other sub-systems. The DI Selector Valve controls the supply of fluids (either DI or Wash Buffer) to the Fluid Supply Manifold.

Tubing and Fittings—Various small diameter tubing and fittings used to connect the components.

In a preferred embodiment, Wash Buffer Supply has four sensors 832, 834, 836, 838, which are preferably conductive sensors. In one embodiment, the sensors are stainless steel probes with a voltage applied to them. Wash Buffer completes a circuit between the probe and a common probe to trip the sensor. The common probe is also a stainless steel probe.

- Bulk Wash Buffer Supply Low Liquid Level Sensor—Monitors the low liquid level within the Bulk Wash Buffer Supply. When tripped, this sensor causes the software interface to notify the customer that additional Wash Buffer is required.
- Bulk Wash Buffer Supply High Liquid Level Sensor—Monitors the high liquid level within the Bulk Wash Buffer Supply.
- Internal Wash Buffer Reservoir Low Liquid Level Sensor 834—Monitors the low liquid level within the Internal Wash Buffer Reservoir. When tripped, this sensor causes the Internal Wash Buffer Reservoir to be filled from the Bulk Wash Buffer Supply (provided Wash Buffer is present). The sensor is currently set to trip when the internal capacity falls below 550 ml.
- Internal Wash Buffer Supply High Liquid Level Sensor 836—Monitors the high liquid level within the Internal Wash Buffer Reservoir. When tripped, this sensor stops the filling of the Internal Wash Buffer Reservoir.

Sheath Subsystem #3

The Sheath Subsystem stores and delivers sheath to the Detector Module. Sheath is supplied to the Detector Module in both a precision metered flow and a non-pressurized flow.

The Sheath Subsystem includes of the following components;

- Bulk Sheath Supply—5 Liter Capacity—A customer accessible container with liquid level monitoring. The Bulk Sheath Supply has the capacity to supply the instrument with Sheath for an eight-hour continuous run. The liquid level sensing is used to notify the customer, via a software interface, when additional Sheath is required. This container is not pressurized or under a vacuum.
- Sheath Intake Pump—Pumps Sheath from the Bulk Sheath Supply to the Internal Sheath Supply. The pump is activated when the Sheath level in the Internal Sheath Supply falls below a specific level. A self-priming diaphragm pump is used in this capacity.
- Sheath Intake Check Valve—Prevents Sheath from traveling from the Internal Sheath Supply to the Bulk Sheath Supply. The check valve (1.5 psi cracking pressure) is required because the Internal Sheath Supply is pressurized.
- Internal Sheath Supply—1 Liter Capacity—An internal Sheath reservoir with liquid level monitoring. Either the Sheath Fluid Gear Pump or the Detector Module Syringe Pump draws the Sheath from the Internal Sheath Supply. The Internal Sheath Supply capacity is always maintained to provide for the completion of all in-process assays should the Bulk Sheath Supply be exhausted or removed. The current minimum is 550 ml.
- Detector Module Sheath Fluid Gear Pump—Provides Sheath from the Internal Sheath Supply at a precise flow rate (90 uL/sec+5%) to the Detector Module Cuvette. The importance of the flow rate to the success of this technology requires the use of an extremely high quality pump.
- Syringe Pump Filter (1 μm)—Filters the Sheath prior to use by the Detector Module Syringe Pump.
- Tubing and Fittings—Various small diameter tubing and fittings used to connect the components.

The Sheath Supply has five sensors. Conductive sensors are used in Sheath. The sensors are simple stainless steel probes with a voltage applied to them. Sheath completes a circuit between the probe and a common probe to trip the sensor. The common probe is also a stainless steel probe.

- Bulk Sheath Supply Low Liquid Level Sensor—Monitors the low liquid level within the Bulk Sheath Supply. When tripped, this sensor causes the software interface to notify the customer that additional Sheath is required.
- Bulk Sheath Supply High Liquid Level Sensor—Monitors the high liquid level within the Bulk Sheath Supply. o Internal Sheath Reservoir Low Liquid Level Sensor—Monitors the low liquid level within the Internal Sheath Reservoir. When tripped, this sensor causes the Internal Sheath Reservoir to be filled from the Bulk Sheath Supply (provided Sheath is present).
- Internal Sheath Supply Mid Liquid Level Sensor—Monitors the mid liquid level within the Internal Sheath Reservoir. This sensor ensures enough Sheath fluid is present within the reservoir to complete processing of all aspirated samples in the instrument. When tripped, this sensor stops the filling of the Internal Wash Buffer Reservoir.
- Internal Sheath Supply High Liquid Level Sensor—Monitors the high liquid level within the Internal Sheath Reservoir. When tripped, this sensor stops the filling of the Internal Sheath Reservoir.

Wash, Separate and Re-Suspend Subsystem #4

The Wash, Separate and Re-Suspend System, aspirates liquid from RVs, disposes of aspirated waste, cleans Wash Probes, dispenses Wash Buffer to RVs. The Wash, Separate & Re-Suspend Subsystem consists of the following components;

- Wash Dispense Pump (FMI type)—Pumps accurately metered volumes of Wash Buffer to the Wash Dispense Probe. The amount of liquid pumped is dependent on the washing and re-suspension requirements for each individual assay.
- Wash Dispense Probe—Dispenses the Wash Buffer provided by the Wash Dispense Pump into the RV.
- Wash Probes—Aspirates liquid from RVs in the Separation Carousel. The Wash Probe Robot lowers the four Wash Probes into the RVs. The Wash Probes are positioned (aligned) to provide a consistent liquid aspiration in any RV position. The depth of probe insertion is optimized to remove liquid and retain bead (in the bead patch).
- Wash & Separate Waste Container—Collects all liquid waste aspirated through the Wash Probes. This container serves as a temporary storage for liquid waste being moved from the Wash Probes to the Internal Waste Containers.
- Wash Waste Valve—Allows liquid waste to be drawn from temporary storage (Wash & Separate Waste Container) to Waste Management System.
- Wash & Separate Clean Valve—Allows DI Water to flow into the Wash Probe Clean Station.
- Wash Probe Clean Station—Presents four individual clean stations (as a group) to the Wash Probes. The clean station is fitted with liquid level sensing to identify blockages in the Wash Probes. If liquid remains in one of the clean stations after aspiration, then the probe must be blocked.
- Tubing and Fittings—Various small diameter tubing and fittings used to connect the components. The Wash, Separate & Re-Suspend System has two sensors. Both of these sensors are conductive sensors that use liquid to trip the sensor.
- Wash Probe Clean Station Liquid Level Sensor—Monitors the liquid within the Wash Probe clean station. Since each probe has its own clean station (well), the sensor monitor the liquid within the well. If liquid remains in any of the wells after cleaning, the sensor is tripped. This presence of liquid indicates the blockage of one or more of the Wash Probe. The customer is notified of this and directed to take corrective action.

Wash Separate Waste Reservoir Sensor—Monitors the liquid waste level within the Wash Separate Waste Container. The sensor is mounted in the top of the container and is tripped when liquid fills the container. Under normal operation, liquid does not remain in the container.

Reagent Transfer Subsystem #5

The Reagent Transfer Subsystem aspirates and dispenses reagents as well as cleaning the Reagent Probe. The Reagent Robot physically transfers reagents from the Reagent Carousel to RVs on the Incubator Carousel. The Reagent Transfer Subsystem includes the following components:

Reagent Syringe Pump—A highly accurate 2.5 ml cavro syringe pump used to aspirate and dispense reagent and push DI Water through the Reagent Probe for cleaning Reagent Probe—Aspirates and dispenses reagents.

Reagent Clean Station—A fixed mounted clean station for the Reagent Probe. DI Water is pumped into the clean station when the Reagent Clean Valve is opened.

Reagent Clean Valve—Allows DI Water to flow into Reagent Clean Station. o Reagent Waste Valve—Allows liquid waste to flow from the clean station to the Waste Management System.

Tubing and Fittings—Various small diameter tubing and fittings used to connect the components. The Reagent Transfer System has two sensors.

Reagent Probe Blockage Detection Unit—Monitors the vacuum and pressure used to aspirate and dispense reagent. If the Reagent Probe becomes blocked the vacuum or pressure will increase, tripping the sensor. The customer is notified of this and directed to take corrective action, such as cleaning or replacing the probe.

Reagent Probe Liquid Level Sensor—Detects when the Reagent Probe comes in contact with reagents. The change in capacitance is determines liquid contact. The software ensures the probe is inserted far enough for reagent aspiration, and calculates of reagent supplies remaining within the reagent pack uses this liquid level sensing.

Specimen Transfer Subsystem #6

The Specimen Transfer Subsystem aspirates, moves and dispenses specimen samples into RVs on the Incubator Carousel. Additionally, it cleans the Specimen Probe and disposes of the waste. The Specimen Transfer includes the following components.

Specimen Syringe Pumps—Two highly accurate cavro syringe type pumps used to aspirate sample from sample tubes and dispense into RVs. The 2.5 ml pump is used exclusively for cleaning of the probe while the 250 µl pump is used for sample aspiration and dispense.

Specimen Clean Syringe Pump o Blockage Detection Fitting—A sensor designed to determine if the Specimen Probe is blocked. It is located on the tubing between the Specimen Probe and Specimen Aspirate Syringe Pump.

Specimen Probe—Aspirates and dispenses sample. o Specimen Probe Clean Station—A fixed mounted clean station for the Specimen Probe. DI Water is pumped into the clean station when the Specimen Probe Clean Valve is opened.

Specimen Probe Clean Valve—Allows DI Water to flow into the Specimen Probe Clean Station.

Specimen Waste Valve—Allows liquid waste to flow from the clean station to the Waste Management System.

Tubing and Fittings—Various small diameter tubing and fittings used to connect the components.

The Specimen Transfer System preferably has two sensors, including a Specimen Probe Blockage Detection Unit that monitors the vacuum and pressure used to aspirate and dispense specimen. If the Specimen Probe becomes blocked the vacuum or pressure will increase, tripping the sensor. The customer is notified of this and directed to take corrective action, such as cleaning or replacing the probe. A Specimen Probe Liquid Level Sensor can be used to detect when the Specimen Probe comes in contact with specimen. The change in capacitance is determines liquid contact. The software ensures the probe is inserted far enough for reagent aspiration.

Detector Module Fluid Transfer Subsystem #7

The Detector Module Fluid Transfer Subsystem removes Detector Module waste and cleans the probe. The Detector Module Fluid Transfer Subsystem includes the following components:

Detector Module Clean Station—A vertical moving clean station for cleaning the Detector Module Probe.

Detector Module Clean Valve—Allows DI Water to flow into the Detector Module Clean Station. DI Water is pumped into the clean station when the Detector Module Clean Valve is opened.

Detector Module Probe Waste Valve—Allows liquid waste to flow from the clean station to the Waste Management System.

Detector Module Probe—A fixed mounted probe through which processed samples are drawn into the Detector Module.

Tubing and Fittings—Various small diameter tubing and fittings used to connect the components.

The Detector Module Fluid Transfer System contains a single sensor relating to the Fluidics.

Detector Clean Station Overflow Sensor—A conductive sensor, located in the top of the Clean Station, that monitors the clean station overfill for liquid. This sensor is designed to monitor the clean station or its tubing and trigger an error when they become blocked.

Waste Management Subsystem #8

The Waste Management System removes and stores waste from the other sub-systems. The customer disposes of stored waste. Additionally, as an option the Waste Management System can be directly plumbed into an existing waste disposal system. The Waste Management System includes of the following components;

Two General Purpose Waste Container—A general temporary waste collection containers (each 1 liter capacity). Typically, liquid waste from the clean stations, drains and clean station overflow is collected here, and then transferred to the Internal Waste Containers.

General Purpose Waste Valve—Allows liquid waste to flow from the General Purpose Waste Container to the General Purpose Manifold.

General Purpose Manifold—Acts as a five-function manifold to processes a wide variety of liquids (waste, Wash Buffer, and DI Water) to various components of the Fluidics System. Each function is independent of all other functions (within the manifold) and are described in the following:

Function 1; Collects waste from the General Purpose Waste Container and Wash & Separate Waste Container and delivers it to the Waste Delivery Manifold.

Function 2; Processes Wash Buffer from the Internal Wash Buffer Reservoir to the Fluid Supply Manifold. The DI Selector Valve controls the flow of Wash Buffer.

Function 3; Provides a path for regulated low vacuum to be monitored on the Fluidics Control Board and supply vacuum to the Wash & Separate Waste Container.

Function 4; Processes DI Water from the Internal DI Water Reservoir to the Fluid Supply Manifold (controlled by the DI Selector Valve) and Wash Probe Clean Station (controlled by the Wash & Separate Clean Valve).

Function 5; Processes liquid waste from Detector Module Clean Station, Reagent Probe Clean Station, and Specimen Probe Clean Station to the Waste Delivery Manifold.

Waste Delivery Manifold—Acts as a four-function manifold to process liquid waste and deliver vacuum and pressure to components requiring them. Each function is independent of the other functions (within the manifold) and are described below.

Function 1; Collects liquid waste from General Purpose Manifold and delivers is to the Internal Waste Containers.

Function 2; Provides a path for unregulated pressure and vacuum to enter the Waste Management System. The Pressure/Vacuum Selector Valve determines if pressure or vacuum is supplied. Upon exit of the manifold the Waste Changeover Valve determines the destination of the pressure or vacuum.

Function 3; Provides a path for a regulated high vacuum to be monitored on the Fluidics Control Board and supply vacuum to the Internal Waste Reservoirs.

Function 4; Provides a path for a regulated pressure to be monitored on the Fluidics Control Board, pressurize the Internal Wash Buffer and DI Water Reservoirs and pressurize the Internal Waste Container.

Waste Changeover Valve—Selects which output (waste and vacuum or pressure) from the Waste Delivery Manifold is delivered to the Bottle Selector Waste Manifold. Selecting waste and vacuum output, draws waste to the Internal Waste Containers (from the various sub-assemblies). While selecting pressure output, pushes waste from the Internal Waste Container to the Bulk Waste Container.

Bottle Selector Waste Manifold—Delivers the selected output (waste and vacuum or pressure) from the Waste Changeover Valve to the Internal Waste Containers. The Waste Changeover Valve determines the output delivery and the manifold simply delivers it to the desired location.

Internal Waste Containers (Qty—2)—Provide liquid waste storage with a holding capacity of eight hours of instrument operation. During normal operation, only one container is filled at a time. Each container has three liquid level sensors. A low level sensor indicates the container is present (the container will never empty below this level, so if the sensor registers liquid, a container must be present). A mid level sensor to ensure that all the samples in-process on the instrument can be completed. This is used to ensure all in-process samples can be completed without the removal of any waste. A high level sensor to determine when a container is full.

Purge Selector Valve—Determines which Internal Waste Container will be purged to the Bulk Waste Containers.

Purge On/Off Valve—Allows the Internal Waste Containers to be purged to the Bulk Waste Containers.

Bulk Waste Selector Valve—Determines which Bulk Waste Container waste is purged to from the Internal Waste Containers.

Bulk Waste Containers—10 liter capacity (Qty 2)—Provides bulk liquid waste storage. The customer is required to remove and empty the waste in these containers. Each container has a high liquid level sensor to determine when the container is full.

Tubing and Fittings—Various small diameter tubing and fittings used to connect the components. The Waste Management System has ten sensors. All sensors within the Waste Management System are conductive type.

GP Waste Container High Liquid Level Sensor—Monitors the high liquid level within the GP Waste Container. When tripped this sensor, initiates the removal of waste from the GP Waste Container.

GP Waste Container Low Liquid Level Sensor—Monitors the low liquid level within the GP Waste Container. When tripped, this sensor stops the removal of waste from the GP Waste Container.

Internal Waste Container 1 High Liquid Level Sensor—Monitors the high liquid level waste within the Internal Waste Container 1. When tripped, this sensor prevents additional waste from being added to the container (assumes the container is full).

Internal Waste Container 1 Mid Liquid Level Sensor—Monitors the mid liquid level waste within the Internal Waste Container 1. This sensor ensures the waste container contains adequate capacity to process all waste from samples currently being processed.

Internal Waste Container 1 Low Liquid Level Sensor—Monitors the low liquid level waste within the Internal Waste Container 1. Since a certain amount of liquid should always be present in the container, the tripping of this sensor indicates the bottle has been removed. When tripped, this sensor prevents additional waste from being added to the container.

Internal Waste Container 2 High Liquid Level Sensor—Monitors the high liquid level waste within the Internal Waste Container 2. When tripped, this sensor prevents additional waste from being added to the container (assumes the container is full).

Internal Waste Container 2 Mid Liquid Level Sensor—Monitors the mid liquid level waste within the Internal Waste Container 2. This sensor ensures the waste container contains adequate capacity to process all waste from samples currently being processed. o Internal Waste Container 2 Low Liquid Level Sensor—Monitors the low liquid level waste within the Internal Waste Container 2. Since a certain amount of liquid should always be present in the container, the tripping of this sensor indicates the bottle has been removed. When tripped, this sensor prevents additional waste from being added to the container.

Bulk Waste Container 1 High Liquid Level Sensor—Monitor the high liquid level waste within the Bulk Waste Container 1. When tripped, this sensor prevents additional waste from being added to the container (assumes container is full).

Bulk Waste Container 2 High Liquid Level Sensor—Monitor the high liquid level waste within the Bulk Waste Container 2. When tripped, this sensor prevents additional waste from being added to the container (assumes container is full).

Pressure Subsystem #9

The Pressure Subsystem creates, stores and delivers pressure to the other sub-systems. Pressure is used to transfer fluids by other sub-systems. The Pressure Subsystem includes the following components.

Pressure Pump—Supplies pressure to the Pressure Accumulator. The pressure Accumulator holds pressure until needed by the instrument. The Accumulator Pressure Sensor on the Fluidics Control Board monitors the pressure.

Pressure Regulator—Regulates the pressure supplied to the Waste Delivery Manifold.

Regulated Pressure Sensor—Monitors the regulated pressure on the Waste Delivery Manifold.

Accumulator Pressure Sensor—Monitors the pressure in the Pressure Accumulator.

Pressure/Vacuum Selector Valve—Determines if pressure or vacuum are delivered to the Waste Delivery Manifold Tubing and Fittings—Various small diameter tubing and fittings used to connect the components. The Pressure System has two sensors.

Accumulator Pressure Sensor—Monitors the pressure within the Pressure Accumulator. The pressure is measured at the accumulator. The sensor is located on the Fluidics Board.

Regulated Pressure Sensor—Monitors the regulated pressure used by the DI Water and Wash Buffer Supplies. The regulated pressure is measured at the Waste Delivery Manifold and only during instrument warm up to ensure the regulator is functioning properly. The sensor is located on the Fluidics Board.

Vacuum Subsystem #10

The Vacuum Subsystem creates, stores and delivers vacuum to the other sub-systems. Vacuum is used to transfer fluids by the other sub-systems. The Vacuum Subsystem includes of the following components;

Vacuum Pump—Supplies vacuum to the Vacuum Accumulator

Vacuum Accumulator—Holds vacuum until needed by the instrument. A liquid level sensor monitors the Vacuum Accumulator to prevent liquid from being draw in.

High Vacuum Regulator—Regulates the high vacuum supplied to the Waste Delivery Manifold.

Regulated High Vacuum Sensor—Monitors the high vacuum at the Waste Delivery Manifold.

Regulated Low Vacuum Sensor—Monitors the low vacuum at the General Purpose Manifold.

Accumulator Vacuum Sensor—Monitors the vacuum levels within the Vacuum Accumulator.

Tubing and Fittings—Various small diameter tubing and fittings used to connect the components. The Vacuum System has four sensors.

Accumulator Vacuum Sensor—Monitors the vacuum within the Vacuum Accumulator. The vacuum is measured at the accumulator. The sensor is located on the Fluidics Board.

Accumulator Liquid Level Sensor—Monitors the amount of liquid within the Vacuum Accumulator. The addition of liquid to the Vacuum Accumulator is the indication of a problem.

Regulated Low Vacuum Sensor—Monitors the low regulated vacuum used by the Wash Buffer Supply and the Wash, Separate & Re-Suspend System and only between washes during sample processing. The low regulated vacuum is measured at the General Purpose Manifold. The sensor is located on the Fluidics Board.

Regulated High Vacuum Sensor—Monitors the high-regulated vacuum used by the Waste Management System. The high-regulated vacuum is measured at the Waste Delivery Manifold and only during instrument warm up to ensure the regulator is functioning properly. The sensor is located on the Fluidics Board.

Fluidics PCB #11

Although the Fluidics PCB is technically part of the Electronics section, it is important to discuss some of its function here to understand the operation of the Fluidics system. The Fluidics PCB provides a central location for all control and sensor connections in the Fluidics system. This design minimizes the length of wiring required and increases serviceability of the Fluidics system. The Fluidics PCB has the five pressure and vacuum (3 pressure, 2 vacuum) sensors located on it. They are connected to the various other components by tubing. The placement of the sensors on the Fluidics Board allows the sensor size to be minimized while maximizing reliability.

The Fluidics System performs a large number of tasks in both serial and parallel. To understand the Fluidics System, it is helpful that the workings of the pressure and vacuum are understood. The pressure side and vacuum side work in tandem to perform the various tasks required of the fluidics system by the instrument. The fluidics system is controlled by the electronics and computer system of the instrument. It should be noted that during any task performed by the fluidics system, the electronics and computer system must control both the pressure and vacuum sides. Failure to do so will result in the fluidics system being unable to successfully complete its assigned task.

5.3.12.3 Internal Reservoir Sensing

The five internal reservoirs within the instrument allow replacement of the external bulk bottles without interruption of instrument operation. The electrical connection and liquid level sensing probes are the same or similar on four of them (Wash Buffer, Sheath, and two Waste).

The four reservoirs optionally are configured as shown in FIG. 48A and using the following configuration of liquid level sensing probes

TABLE 18

Examples of liquid level sensing probes.

| Reservoir | Probe #1 | Probe #2 | Probe #3 | Probe #4 | Fluid Pick Up Line |
|---|---|---|---|---|---|
| Sheath | 0 V Reference (55 ml Volume) | 550 ml Probe | 900 ml Probe | 55 ml Probe (Blanking Probe) | Yes. At bottom of bottle (55 ml) |
| Buffer | 0 V Reference (55 ml Volume) | 550 ml Probe | 900 ml Probe | 55 ml Probe (Blanking Probe) | Yes. At bottom of bottle (55 ml) |
| Waste (2) | 0 V Reference (55 ml Volume) | 550 ml Probe | 900 ml Probe | 55 ml Probe | Yes. At bottom of bottle (55 ml) |

The DI water reservoir liquid level sensing is configured as shown in FIG. 48A.

5.4 Host Computer System

Referring back to FIG. 1, host computer system 40 of the MAD system 10 preferably includes a processor, a user in, keyboard, trackball for data entry, touch screen, VGA high resolution monitor, printer, and software. The computer system preferably has a dual microprocessor, one gigabyte of RAM memory, two 40 gigabyte hard drives, and a dual asynchronous serial interface. The computer system is responsible for carrying out all of the necessary operations from instrument control to results evaluation, data storage, quality control, mainframe bidirectional interfacing, and operator assistance. The computer system is connected to the analyzer through two USB ports, while the printer is operated through a parallel port. The computer system has a LAN and a modem line connector.

The MAD system hardware and software provide complete control of the flow cytometer and performs real-time classification of the microspheres and analysis of the microsphere-based reactions simultaneously. The hardware includes a personal computer interface card that provides communication between the computer and the flow cytometer. The interface card has an on-board, high-speed digital signal processor that is capable of performing >30 million mathematical functions per second. The software is a WINDOWS2000/XP®-based 32-bit application that provides a "multiplexed mode" for automated multiplexed analysis, as well as a "data acquisition mode" for nonautomated gating and data acquisition. In addition, statistical analysis generated by the software is recorded to comma-separated-value (CSV) files that can be read by third-party spreadsheet programs.

The instrument control software is in excess of 100,000 lines of C++ code, running under the QNX multi-threaded real time operating system, and performs all instrument control, specimen process scheduling, and error handling operations. Furthermore, instrument code can be upgraded or changed from the host via the USB interface or over a network from a remote server.

Turning now to the software component of the MAD system, the host software includes instructions for operating and controlling the multiple robots incorporated in the device. Furthermore, the host software controls movement of samples, pipetting samples, pipetting reagents, flushing samples, analyzing samples, reporting data, and troubleshooting the device.

In one embodiment, the MAD system software is divided into the following blocks:

(A) RUN—execution and evaluation of testing;
(B) Quality Control—long term quality control;
(C) System Parameter—operational programming, e.g., test applications, mainframe interface configurations, and calculations mode; and
(D) System Functions—system tests and troubleshooting System operators spend the majority of their time in the RUN block. The RUN block is discussed below in some detail.

To begin a run the operator first enters the patient requisition information which includes the patient name/number and the test(s) or panel selections. Patient demographics may also be entered now or, for better time efficiency, after the run has begun. Several operator defined functions exist to allow for rapid requisition entries. After the sample requests are ordered, it is possible to segregate the samples or specific assays.

In addition to the flexible sample handling, options are also provided for the run's calibration curve and controls. For each run the operator may choose from: (1) a full calibration curve, (2) one or two point adjustment, or (3) no calibrator, using the stored curve. Calibrators are run in duplicate and samples are run singularly. As many as three controls may be run per assay panel.

Other important functions of the RUN block include loading status, run optimization, run status, documentation, data conclusion/archive, and system cleaning What follows is a brief overview of each of these modules. Loading status provides a printed summary of the requested run. This load list includes all bulk solutions, reagents, samples, cleaning solution, and RVs; it indicates their volumes required for the run, and provides the appropriate numbered position for each constituent on the reagent, sample, and incubator rotors.

One of the functions of the software is to calculate the appropriate pipetting sequences. This feature allows the assays of a specific run to be performed during the shortest possible time period and thus optimize the workload management.

The "Run" status allows the operator to determine at any time the system's progress in the run. It shows the individual procedural steps of pipetting, incubation, washing, and flow cytometric measurements for each assay in the run, including their start and end times.

5.5 Examples 5.5.1 General Method of Use of a MAD Instrument and System

In a preferred embodiment, a MAD instrument and system 10 allows for simultaneous detection of multiple analytes a single sample. Hence, the instrument makes possible a "multi-analyte detection system." The system is designed to simultaneously detect the presence of multiple different (up to approximately 25) antibodies in a test sample (e.g., a blood sample). This system utilizes the following basic steps:

1) A test sample to be analyzed for the presence of one or more "analytes" of interest is contacted with a population of magnetic beads. A bar code is used to identify the test sample. In such a system, the analytes are particular antibodies that may be present in the test sample. Different beads within the population exhibit different particular combinations of fluorescent dyes and "analyte detectors." In a current embodiment, the analyte detectors are particular antigens. Each analyte detector binds a particular analyte to be detected. Specifically, each magnetic bead is uniquely dyed with two distinct fluorescent dyes. Thus, in the current BioPlex 2200 system, each analyte detector antigen binds a particular analyte antibody. The dyes are preferably oil-soluble or hydrophobic and the dyes are incorporated into the bead rather than being attached to the bead's surface. Each dye can have any of ten (10) or more possible levels of fluorescent intensity, thus creating a family of up to one hundred (100) or more spectrally addressed (color coded) beads. Any particular magnetic bead is identified via a specific combination of fluorescent dyes (the combination is referred to collectively as a "classification dye") the bead exhibits. Each magnetic bead exhibiting a particular classification dye also exhibits a particular analyte detector (antigen). Thus, by detecting a particular classification dye of a magnetic bead, one also identifies the specific analyte detector (antigen) the magnetic bead exhibits. Generally, the test sample and magnetic beads are incubated for approximately 15 minutes at 37° C. inside the instrument reaction vessel.

2) After incubation, the magnetic beads are washed (generally three times) to remove unbound test sample material. Specifically, when the reaction vessel is ready to be washed, a magnetic field is applied that draws the magnetic beads to the wall of the reaction vessel, where they are maintained during washing. After each washing, the magnetic field is removed and the beads are resuspended. One skilled in the art will appreciate that the beads and/or magnets may incorporate various types of materials that either produce or respond to magnetic fields such that the beads are attracted to the side of a reaction vessel during washing.

3) After washing, the only antibodies remaining in the reaction vessel are those that had bound to antigens present on the now washed magnetic beads. The washed magnetic beads, some or all of which may have bound analytes (antibodies of interest) present in the test sample, are then contacted with a labeled reporter molecule that is a fluorescently labeled secondary antibody designed to bind to any antibody (e.g., any human antibody or any particular class of human antibody) left remaining in the reaction vessel. Thus, those magnetic beads that bound an antibody from the test sample will, in this step, also bind a labeled reporter molecule. Generally, the beads and the labeled reporter molecule are incubated in the reaction vessel for approximately 15 minutes at 37° C.

4) The magnetic beads are then washed again to remove any unbound labeled reporter molecules, as described in 2), above.

5) At this point, those antibodies from the test sample that had bound to the magnetic beads have been bound by a labeled reporter molecule. The reaction vessel containing the magnetic beads is introduced to the detector module 20. In this example, a suitable detector module includes flow cytometry mechanisms and at least two lasers. The two lasers are a red 635 nm classification laser and a green 532 nm reporter laser. The magnetic beads are then analyzed via flow cytometry involving a two laser system, in which one laser can detect and identify a classification dye and the second can detect the labeled reporter molecule. The identification of a particular classification dye passing through a particular flow cell indicates what analyte detector (antigen) the magnetic bead carries. If that bead is also determined to have bound a labeled reporter molecule, then the test sample contains the analyte (antibody) the particular magnetic bead is designed to detect. As all the magnetic beads are evaluated together via this two laser system, the presence of each of the multiple analytes (antibodies) is evaluated simultaneously. The results are read, collated and displayed and/or stored by a computer.

As pointed out above, the detector module in this example utilizes flow cytometry technology employing two lasers of different frequencies. One laser excites the fluorescent dye in the bead to identify the bead that just has passed through the flow cell by detecting the bead classification dye. The other laser excites the fluorescent dye bound to the labeled reporter molecule to indicate that an antibody from the test sample is bound to the magnetic particle.

In particular, the detector module in this example involves two solid-state lasers. First, a red diode classification laser excites fluorochromes embedded through the dyes of the bead. When the red diode classification laser illuminates a dyed bead, the bead's fluorescent signature identifies it as a particular member of one of the species of classification dyes (a qualitative analysis). Software correlates the bead species to the particular analyte detector (antigen) present on the magnetic bead. Second, a green reporter laser simultaneously excites a fluorescent dye bound to the labeled reporter molecule in the assay. The amount of green fluorescence is directly proportional to the amount of analyte (antibody) captured in the immunoassay (a quantitative analysis).

Digital signal processing algorithms, for example in the host computer or in the detector module, provide real-time data acquisition from thousands of beads per second. Using high speed digital signal processing, about 100,000 beads can be screened per minute and up to 25 different analytes (antibodies) can be assessed in seconds. Extrapolating the standard curve allows the quantitation of each analyte in the sample.

According to one embodiment, a MAD system essentially comprises two sub-systems, namely an assay processing sub-system (e.g., a sample processing module) and an analysis sub-system (e.g., a detector module). The assay processing sub-system includes, inter alia, the following hardware components: reaction vessels (RVs); RV handlers; an RV hopper; reagent kits; specimen and reagent handlers and probes; at least one bar-code reader; a specimen input area including a specimen rack positioned on a specimen rack tray; a look-ahead platform or pre-view area; a specimen robot; other robotics for transferring the samples and/or reagents; a reagent carousel; other carousels including sample racks; a work surface; an incubation wheel or carousel; at least one specimen aspiration probe; a washing mechanism, including a wash carousel and a wash aspiration robot; and a specimen cleaning station. Furthermore, the assay processing sub-system includes, inter alia, the following software components: software used to control and monitor processing, such as the maintenance sentry, instrument sentry, and sample sentry; a laboratory automation track system (LATS); a laboratory information system (LIS); quality control (QC) tools; remote connectivity management software; and user interfaces.

5.5.2 Serology IgG

In one example, serology infectious disease testing covers all areas of infectious disease, including sexually transmitted diseases, pediatric diseases, viral infections, parasitic infections and others. As an example, a system serology IgG reagent kit includes antigens for up to twelve or more specific infectious diseases. In this example, sixteen specific antigens are used for this purpose. Multiple antigens are used for specific disease association in order to increase assay specific reactivity, and to aid in the clinician diagnosis for staging of the specific disease. TABLE 19 provides of examples of the markers that may be included in a Serology IgG Reagent Kit.

TABLE 19

Serology IgG Reagent Kit Markers

| DISEASE | ANTIGEN 1 | ANTIGEN 2 | ANTI-GEN 3 | COATING |
| --- | --- | --- | --- | --- |
| Toxoplasmosis | T. gondii | None | None | Single |
| Rubella | Rubella | None | None | Single |
| Cytomegalovirus | CMV | None | None | Single |
| Herpes Simplex 1 | HSV-1 | None | None | Single |
| Herpes Simplex 2 | HSV-2 | None | None | Single |
| Epstein Barr Virus | VCA | EBNA-1 | EA-D | Individual |
| Measles | Measles | None | None | Single |
| Mumps | Mumps | None | None | Single |
| Varicella Zoster Virus | VZV | None | None | Single |
| Syphilis | T. pallidum r 15 | T. pallidum r 47 | None | Individual |
| Lyme | B. burgaorferi 31 | B. garinii | B. afzelli | Individual |
| Helicobacter Pylori | H. pylori 1 | H. pylori 2 | None | Co-Coat |

The first column identifies disease. The second, third, and fourth indicate what antigens are used to detect the disease. The last column identifies how the antigens are coated. Single indicates only one antigen. Individual indicates multiple antigens for same disease, however the listed antigens are coated onto separate beads for identification. Co-Coat indicates multiple antigens coated on the same bead.

Diseases with more than one antigen can be a powerful tool to acquire clinical diagnosis of a sample. For example, EBV infection uses three IgG antigens to identify the disease stage and progression. Offering all three antigens in one tube will give more consistent results, and will offer "possible" disease stage progression, based on an internal look-up table. Syphilis uses two specific recombinant proteins to give higher sensitivity and specificity for a syphilis infection, and may offer disease staging "ideas" to the clinician based on pattern. Lyme offers three distinct strains of Borrelia in order to increase sensitivity, increase market usability, and other potential diseases progression "ideas" based on patterns. *H. pylori* uses two specific proteins Referring to FIGS. 49-51, a method 900 according to the invention is illustrated utilizing the serology IgG assay panel as an example. Method 900 is shown in all three FIGS. 49-51, with the steps beginning at 920 of FIG. 49 continued in FIG. 50, and the steps shown in 930 of FIG. 900 continued in FIG. 51. It should, however, be appreciated that the sequence of steps or the combination of movements may be altered. The IgG assay panel of this example uses three reagents in the reagent packs—magnetic beads solution, sample diluent, and conjugate solution. Once a test run is completed and the instrument is in the idle phase, the MAD system automatically flushes at regular time intervals with wash buffer so as to prevent drying of the probes. The MAD system performs all of the assay steps without operator intervention. A single assay panel or multiple random-access assays can be performed with minimal operator time.

5.5.3 Serology IgM

Detection of IgM antibodies is often used to identify an early or acute infection and is helpful to fully understand the progression of an infection.

Serology IgM in some cases offers a few more challenges to antibody detection than IgG. Two main problems that can occur with IgM detection include IgG replacement and Rheumatoid Factor replacement. First, if a sample has both IgG and IgM antibodies to one antigen, the IgG antibody will always bind to the antigen first. The IgG and IgM antibodies compete for the same antigen, and IgG will almost always win, due to steric hindrances and higher affinity. This can lead to false negative results on a standard IgM assay. Second, Rheumatoid factor, a protein found in a large percent of the population, "mimics" IgM antibodies. Rheumatoid factor will bind to antigens non-specifically, leading to false positive results in the assay. A "capture method" immunoassay helps overcome these problems.

In this example, a capture method for IgM detection uses an IgM antibody coated to the solid phase. This IgM antibody will bind to a IgM in a sample. A conjugate, made up of the specific antigen for testing, is then added to the sample, and will bind to the complex. This then generates a signal that can be detected.

For a standard indirect IgM assay, an extra step is generally performed in order to remove all the IgG antibodies and all the Rheumatoid Factor from the sample. On manual or semi-automated assays, this can cause major delays and problems for programming.

The system 10 serology IgM reagent kit uses an indirect technique, with the absorption step included in the first incubation. The chemistry allowed within the multiplex format does not allow for "capture-like" tests to be developed. This serology IgM reagent kit has proven equivalence versus the capture methods where appropriate.

The serology IgM reagent kit offers essentially the same testing procedure and analyte package as Serology IgG described above, except that:

(a) EBV only offers VCA detection to IgM. Other markers are no value to determining disease stages and are not reimbursable.

(b) Syphilis still uses two distinct recombinant proteins, however the proteins used are *T. pallidum* 17 and *T. pallidum* r 47. Advantages are still present using two distinct antigens.

(c) *H. pylori*-only one antigen is used for detection. However, more may be used.

5.5.4 Autoimmune Systemic Reagent Kit

A MAD system 10 Autoimmune Systemic Reagent Kit offers antibody detection against antigens normally identified as systems autoimmune antigens. This indicates a response that is system-wide, throughout the whole body, and cannot be identified to one specific organ or organs. Disease specific panels affecting multiple organ systems will be used in future product launches. TABLE 20 includes a list of all the antigens present in a MAD System Autoimmune Reagent Kit according to one example.

TABLE 20

| Antigens in Autoimmune Reagent Kit |
|---|
| SSA |
| SSA 52 |
| SSB 48 |
| Sm BB |
| Sm |
| SM RNP |
| RNP 68 |
| RNP A |
| Ribosomal P |
| Nucleosome (DNP) |
| dsDNA (quantitative) |
| Centromere B |
| Sci-70 |
| Jo-1 |

Diseases associated with the above markers, including systemic lupus erythematosus, scleroderma, sjogrens synaroma polymyositis, mixed connective tissue disease (MCTD), and CREST, will not be discussed in detail herein, however they are know in the field.

Software on the M.A.D. system host computer 40 preferably allows the Autoimmune Systemic Reagent Kit to report results in many different methods. One standout feature with this embodiment is the incorporation of a medical decision device system. This system incorporates database in system memory 45 including results generated from known clinical disease samples. As new samples are tested on the system, the antibody response results for that sample are "compared" to the internal database. If the pattern of antibody response is similar to a known clinical disease, the system has the ability to report this correlation.

5.6 Functional Description of a MAD System

FIG. 52 is a block diagram providing a functional description of a MAD system 10, depicting interrelationships of the various functions as described herein which may be performed by the system.

As used throughout this specification MAD and BioPlex2200 are or will be used as trademarks covering this device, processes of this device, and/or any part thereof. The use of MAD and BioPlex2000 is intended to be used in a distinctive sense, not a generic description of the system or method being accomplished.

The foregoing descriptions of specific embodiments of the present invention are presented for purposes of illustration and description. For example, any methods described herein are merely examples intended to illustrate one way of performing the invention. They are not intended to be exhaustive or to limit the invention to the precise forms disclosed. Obviously many modifications and variations are possible in view of the above teachings. Also, any graphs and FIGS. described herein are not drawn to scale. The embodiments were chosen and described in order to best explain the principles of the invention and its practical applications, to thereby enable others skilled in the art to best utilize the invention and various embodiments with various modifications as are suited to the particular use contemplated. Furthermore, the order of steps in the method is not necessarily intended to occur in the sequence laid out. It is intended that the scope of the invention be defined by the following claims and their equivalents.

What we claim is:

1. A reagent storage assembly, comprising:
   an insulated cooler having an inner chamber and a cooling system for maintaining a temperature range within the inner chamber;
   a lead screw centrally located within the inner chamber;
   a reagent carousel configured to hold a plurality of reagent packs, wherein the reagent carousel is removably held within the inner chamber by lead screw;
   a rotational drive configured to rotate said reagent carousel;
   a sun gear assembly comprising a sun gear and planetary gears having gear heads, wherein the sun gear contacts the planetary gears;
   an agitation drive comprising an agitation motor and a clutch, wherein the clutch couples the agitation motor to the lead screw to lift or lower the reagent carousel within the inner chamber or couples the agitation motor to the sun gear to rotate the sun gear and thereby agitate content of reagent bottles situated on top of the planetary gear heads when reagent packs containing reagent bottles are present in the reagent carousel when the reagent carousel is in a lowered position within the inner chamber, and
   a reagent pack piercer having a piercer arm and at least one piercer pin, wherein the piercer arm is coupled to the at least one piercer pin and the at least one piercer pin is adapted to pierce a seal on the reagent bottles when the reagent packs are held in said reagent carousel.

2. The reagent storage assembly of claim 1 further comprising a reagent pack lid opener having actuator pins adapted to open a hingable lid on a reagent pack when the reagent pack is present in said reagent carousel.

3. The reagent storage assembly of claim 1, wherein the planetary gear heads are configured to centralize the reagent bottles when situated on top of the planetary gear heads by positioning the planetary gear heads inside of a circumferential rib of the reagent bottle.

4. The reagent storage assembly of claim 1, further comprising a barcode reader configured to read barcodes on the outer end of the reagent packs when the reagent packs are held in the reagent carousel.

* * * * *